(12) United States Patent
Friedman et al.

(10) Patent No.: US 10,159,735 B2
(45) Date of Patent: Dec. 25, 2018

(54) PHOTOCLEAVABLE DRUG CONJUGATES

(71) Applicant: THE CURATORS OF THE UNIVERSITY OF MISSOURI, Columbia, MO (US)

(72) Inventors: Simon H. Friedman, Kansas City, MO (US); Piyush K. Jain, Kansas City, MO (US); Dipu Karunakaran, Kansas City, MO (US); Bhagyesh R. Sarode, Kansas City, MO (US)

(73) Assignee: The Curators of the University of Missouri, Columbia, MO (US)

(*) Notice: Subject to any disclaimer, the term of this patent is extended or adjusted under 35 U.S.C. 154(b) by 97 days.

(21) Appl. No.: 14/410,606

(22) PCT Filed: Jun. 21, 2013

(86) PCT No.: PCT/US2013/046989
§ 371 (c)(1),
(2) Date: Dec. 23, 2014

(87) PCT Pub. No.: WO2014/004278
PCT Pub. Date: Jan. 3, 2014

(65) Prior Publication Data
US 2015/0328314 A1   Nov. 19, 2015

Related U.S. Application Data

(60) Provisional application No. 61/664,221, filed on Jun. 26, 2012.

(51) Int. Cl.
| | |
|---|---|
| A61K 41/00 | (2006.01) |
| A61K 38/28 | (2006.01) |
| A61N 5/06 | (2006.01) |
| A61K 47/64 | (2017.01) |

(52) U.S. Cl.
CPC .......... *A61K 41/0042* (2013.01); *A61K 38/28* (2013.01); *A61K 47/645* (2017.08); *A61N 5/062* (2013.01); *A61N 2005/0645* (2013.01)

(58) Field of Classification Search
CPC ............... A61K 41/0042; A61K 38/28; A61K 47/48315; A61N 5/062; A61N 2005/0645
See application file for complete search history.

(56) References Cited

U.S. PATENT DOCUMENTS

| 5,430,175 | A | 7/1995 | Hess et al. |
| 5,474,978 | A * | 12/1995 | Bakaysa ................ A61K 38/28 514/6.1 |
| 5,482,719 | A | 1/1996 | Guillet et al. |
| 5,635,608 | A | 6/1997 | Haugland et al. |
| 5,872,243 | A | 2/1999 | Gee et al. |
| 5,888,829 | A | 3/1999 | Gee et al. |
| 6,043,065 | A | 3/2000 | Kao et al. |
| 6,099,864 | A | 8/2000 | Morrison et al. |
| 7,513,906 | B2 | 4/2009 | Passy et al. |
| 7,686,839 | B2 | 3/2010 | Parker |
| 7,991,464 | B2 | 8/2011 | Schmitt et al. |
| 2003/0216284 | A1* | 11/2003 | Fink ........................ A61K 41/00 514/1 |
| 2004/0166146 | A1 | 8/2004 | Holloway et al. |
| 2005/0256384 | A1 | 11/2005 | Walker et al. |
| 2008/0039907 | A1 | 2/2008 | Fiset |
| 2009/0030261 | A1 | 1/2009 | Whitmore |
| 2009/0042235 | A1* | 2/2009 | Hirota ...................... C07K 7/54 435/29 |
| 2009/0208561 | A1 | 8/2009 | Schmitt et al. |
| 2010/0028346 | A1 | 2/2010 | Lutz et al. |
| 2010/0105120 | A1 | 4/2010 | Zebala |
| 2010/0297250 | A1 | 11/2010 | Boons et al. |
| 2011/0027340 | A1 | 2/2011 | King |
| 2011/0165114 | A1* | 7/2011 | McCoy ................ A61K 9/0024 424/78.24 |
| 2013/0045522 | A1* | 2/2013 | Charles ............ A61K 47/48176 435/188 |

FOREIGN PATENT DOCUMENTS

| WO | WO 2009/038776 | 3/2009 | |
| WO | WO2009/038776 A1 * | 3/2009 | ............. A61K 51/00 |
| WO | WO 2011/075736 | 6/2011 | |

OTHER PUBLICATIONS

Shah et al., "Lght-activated RNA interference using double-stranded siRNA precursors modified using a remarkable regiospecificity of diazo-based photolabile groups," 2009, Nucleic Acids Research, 37(13):4508-4517.*

Ning et al., "Protein Modification by Strain-Promoted Alkyne-Nitrone Cycloaddition", 2010, Angew. Chem. Int. Ed., 49:3065-3068.*

Zhao et al., "o-Nitrobenzyl Alcohol Derivatives: Opportunities in Polymer and Materials Science", 2012, Macromolecules, 45:1723-1736.*

Furuta et al., "Brominated 7-hydroxycoumarin-4-ylmethyls: Photolabile protecting groups with biologically useful cross-sections for two photon photolysis," 1999, PNAS USA, 96:1193-1200.*

Kim, et al., "Photocleavage of o-nitrobenzyl ether derivatives for rapid biomedical release applications", *Bioorg. Med. Chem. Lett.* 16 (2006) pp. 4007-4010 (4 pgs).

(Continued)

*Primary Examiner* — Mina Haghighatian
*Assistant Examiner* — Erin E Hirt
(74) *Attorney, Agent, or Firm* — Stinson Leonard Street LLP

(57) ABSTRACT

Novel photocleavable drug conjugates for forming drug depots comprise drugs attached to photocleavable groups. In one embodiment, the drug is linked via photocleavable group(s) to a polymer chain to form a photocleavable drug-polymer conjugate that generally forms the depot matrix. In another embodiment, the drug is crosslinked via photocleavable group(s) to themselves to form a photocleavable drug conjugate that generally forms the depot.

16 Claims, 33 Drawing Sheets

(56) References Cited

OTHER PUBLICATIONS

Furuta, et al., "Brominated 7-hydroxycoumarin-4-ylmethyls: Photolabile protecting groups with biologically useful cross-sections for two photon photolysis", *Proc. Natl. Acad. Sci*, vol. 96, pp. 1193-1200, Feb. 1999 (8 pgs).

International Search Report and Written Opinion from corresponding PCT/US2013/46989 dated Nov. 21, 2013 (17 pgs).

Shah, et al., "Light-activated RNA interference using double-stranded siRNA presursors modified using a remarkable regiospecificity of diazo-based photolabile groups", *Nucleic Acids Research*, 2009, vol. 37, No. 13 pp. 4508-4517 (10 pgs).

Zhao, et al., "o'Nitrobenzyl Alcohol Derivatives: Opportunities in Polymer and Materials Science", *Macromolecules* 2012, Published Jan. 26, 2012, vol. 45, pp. 1723-1736 (14 pgs).

Ning, et al., "Protein Modification by Strain-Promoted Alkyne-Nitrone Cycloaddition", *Angew. Chem. Int. Ed.* 2010, vol. 49, pp. 3065-3068 (4 pgs).

Jain, et al., "Construction of a Photoactivated Insulin Depot", *Angew. Chem. Int. Ed.* 2012, Article first published online Dec. 3, 2012, vol. 51, pp. 1-6 (6 pgs).

Li et al., "Synthesis and evaluation of photolabile insulin prodrugs", *Bioorg. Med. Chem. Lett.* 15 (2005), pp. 3917-3920 (4 pgs).

Sinkel et al., "A Polymeric Drug Depot Based on 7-(2'-Methacryloyloxyethoxy)-4-methylcoumarin Copolymers for Photoinduced Release of 5-Fluorouracil Designed for the Treatment of Secondary Cataracts", *Macromol. Chem. Phys.* 2010, 211, pp. 1857-1867 (11 pgs).

Shi et al., "Photo-tunable protein release from biodegradable nanoparticles composed of cinnamic acid derivatives", *Journal of Controlled Release* 149 (2011) pp. 182-189 (8 pgs).

Alvarez-Lorenzo et al., "Light-sensitive Intelligent Drug Delivery Systems", *Photochemistry and Photobiology* (2009), 85, pp. 848-860 (13 pgs).

McCoy et al., "Light-Triggered Molecule-Scale Drug Dosing Devices", *J. Am. Chem. Soc.* 2007, vol. 129, pp. 9572-9573 (2 pgs).

McCoy et al., "Triggered drug delivery from biomaterials", *Expert Opin. Drug Deliv.* (2010), vol. 7 No. 5 (13 pgs).

Jin et al., "Biocompatible Drug Delivery System for Photo-Triggered Controlled Release of 5-Fluorouracil", *Biomacromolecules* 2011, vol. 12, pp. 2684-3691 (8 pgs).

Hartner, et al., "Dimeric Drug Depot Forms for Photo-Induced Drug Release", Proc. of SPIE, vol. 5323, (SPIE, Bellingham, WA, 2004) pp. 382-389 (8 pgs).

Kim, et al., "Two-Photon Absorption Induced Drug Delivery from Polymers for Medical Applications", Proc. of SPIE, vol. 5323, (SPIE, Bellingham, WA, 2004) pp. 327-334 (8 pgs).

\* cited by examiner

Approach A, "linear":

☐ = photocleavable linker

Approach B, "meshwork":

Sample schematic synthetic methods for Approach A ("linear")

A1 (sequential):   A2 (convergent):

☐ = photocleavable linker

PHOTOCLEAVABLE DRUG CONJUGATES

CROSS-REFERENCE TO RELATED APPLICATIONS

This application is based on and claims priority to U.S. Provisional Application Ser. No. 61/664,221 filed on Jun. 26, 2012, which is hereby incorporated herein by reference.

BACKGROUND OF THE INVENTION

There are many drugs, especially protein based drugs, that would benefit from controlled release in response to physiological signals. A prime example of this is insulin, as used by diabetics, which needs to be administered multiple times per day, in varying amounts, in response to changing blood sugar levels. The present invention is directed to novel photocleavable drug conjugates and drug delivery methods and systems which use such conjugates.

BRIEF SUMMARY OF THE INVENTION

The present invention is directed to novel compositions of matter and methods for drug delivery. In particular, the present invention is generally directed to a composition of matter which permits the toggling of the release of drugs inside the body by using an implantable, preferably injectable, light activated drug depot. Although insulin will be used to describe the drug delivery approach, it will be readily appreciated that the present invention can be applied to any molecule in which controlled and/or timed release is desired to maximize effectiveness. Such molecules include but are not limited to small molecule drugs, peptides, proteins, nucleic acids, and macromolecules.

In one aspect, the present invention is directed to a photocleavable drug-polymer conjugate. The photocleavable drug-polymer conjugate comprises a polymer chain linked via a photocleavable group to a drug molecule. The photocleavable drug-polymer conjugate is designed to function as a drug depot. The photocleavable drug-polymer conjugate is preferably formulated as a depot suitable for cutaneous, subcutaneous, or intramuscular implantation. Upon irradiation with light of a suitable wavelength, the photocleavable group is cleaved, thereby releasing the drug molecule from the polymer chain.

In another aspect, the present invention is directed to a photocleavable drug conjugate. In such an embodiment, the photocleavable drug conjugate does not comprise a polymer chain that functions as a backbone for drug loading. Instead, the drug molecule is crosslinked with the photocleavable group to other drug molecules. The photocleavable drug conjugate is designed to function as a drug depot. The photocleavable drug conjugate is preferably formulated as a depot suitable for cutaneous, subcutaneous, or intramuscular implantation. The preferred drug molecules are polymers having multiple functional groups suitable for crosslinking (for example, drug molecules containing one or more amine or carboxyl groups), such as therapeutic peptides, and the most preferred drug molecule is insulin. The preferred photocleavable group is a bifunctional or multifunctional photocleavable group such that photolysis may occur at two or more places in the linker. Upon irradiation with light of a suitable wavelength, the photocleavable group is cleaved, thereby releasing the drug molecule from the photocleavable drug conjugate.

In one aspect, the depot (whether comprising the photocleavable drug-polymer conjugate or the photocleavable drug conjugate) is located in the cutaneous region of the skin, for example, in the stratum germinativum and/or stratum spinosum of the epidermis. In another aspect, the depot is located in the dermis, for example in the papillary layer and/or the reticular layer. The location is preferably such that the tissue is sufficiently vascularized to permit distribution of the drug through the body. The location is also preferably such that the light is able to penetrate through the tissue to photorelease the drug from the conjugate.

In one aspect, the present invention overcomes the problem associated with conventional drug delivery whereby frequent injections of the drug, such as insulin, are needed. For example, a patient may require a total daily dose of insulin of about 1 to 100 IU per day (e.g., about 1, 2, 3, 4, 5, 6, 7, 8, 9, 10, 20, 30, 40, 50, 60, 70, 80, 90, 100 IU per day), and typically about 0.1 to 2 IU/kg/day (e.g., about 0.1, 0.2, 0.3, 0.4, 0.5, 0.6, 0.7, 0.8, 0.9, 1, 1.0, 1.1, 1.2, 1.3, 1.4, 1.5, 1.6, 1.7, 1.8, 1.9, 2 IU/kg/day). This may be a dose of about 1 to 4 mg of insulin per day. In the present invention, the depot may contain a supply of insulin that lasts for several days, weeks, or even months. It is contemplated that in one aspect, an entire two-month supply or more of insulin could be deposited in the drug depot in a single injection in a volume equivalent to a single dose of traditional insulin. This dramatically reduces the number of injections needed to control a patient's disease, that is, there may be as much as a 50-, 100-, or even 200-fold reduction in the injection number. In another aspect, the present invention overcomes the problem associated with conventional insulin use whereby there is significant variability of blood sugar levels. In the present invention, there is a potential for rapid (e.g., real time, minute-by-minute, or hour-by-hour) correction of blood sugar levels through the non-invasive and continuously variable release of insulin with light. In one aspect, native like, rock-level blood sugar levels of a non-diabetic could potentially be obtained.

In some aspects, the conjugates of the present invention may be synthesized using bioorthogonal coupling reactions, which may include, but are not limited to the chemistry found in Native Chemical Ligation ("NCL") and Expressed Protein Ligation ("EPL"), carbonyl ligations, Diels-Alder reactions, Pd- and Rh-catalyzed ligations, decarboxylative condensations, thioacid/azide ligations, maleimide/thiol pairs, aziridine ligations, the Staudinger ligation, and the Sharpless-Huisgen cycloaddition. These reactions are often cited as examples of "click chemistry," a term used in the art to refer to chemical reactions that are specific, high yielding, and tolerant of functional groups.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 2 illustrates the linear approach in an exemplary embodiment.

In FIG. 5B, an exemplary synthesis for linking a drug molecule, such as insulin, to a polymer chain which is a polypeptide or protein having an amine is shown. In this exemplary synthesis, the photocleavable group has a carboxyl which is reacted with an amine on a lysine residue on the polypeptide or protein. A diazo is formed on the photocleavable group, which is reacted with the carboxyl groups on the insulin. Linkage to three lysine residues are illustrated.

FIG. 19 summarizes the photorelease studies of an exemplary photocleavable drug-polymer conjugate. FIG. 19B shows the cumulative amount of insulin released as a function of the time of irradiation, while

DETAILED DESCRIPTION OF PREFERRED EMBODIMENT

Figure 1:
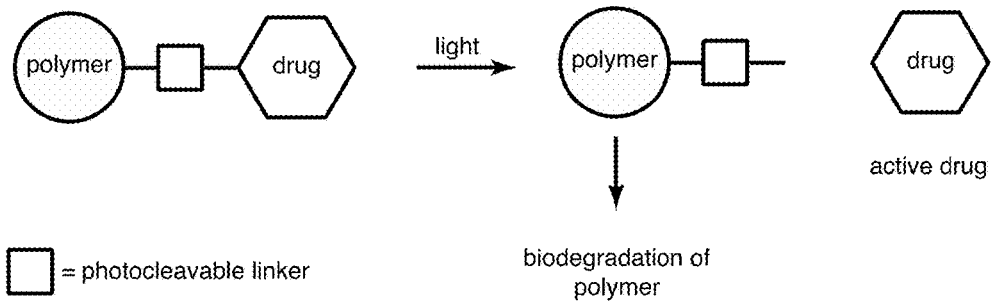
FIG. 1 illustrates a two drug delivery strategies in accordance with the present invention for allowing the controlled release of a drug with light. Approach A (or the "linear" approach) involves a photocleavable drug-polymer conjugate comprised of a drug molecule linked to an insoluble polymer chain with a photocleavable group serving as the linker. The insolubility of the polymer chain allows a drug depot comprising the of the photocleavable drug-polymer conjugate to remain at a site of implantation until irradiation takes place. At that point, the drug molecule is released from the conjugate and is absorbed into the system. The polymer can then biodegrade, clearing it from the depot site. In Approach B (or the "meshwork" approach), a drug molecule is linked to other drug molecules via a photocleavable linker. In such a fashion, the drug molecules create the bulk of the conjugate through the creation of a three dimensional meshwork. Upon photolysis, the drug molecule is released from the photocleavable drug conjugate.
Figure 1:
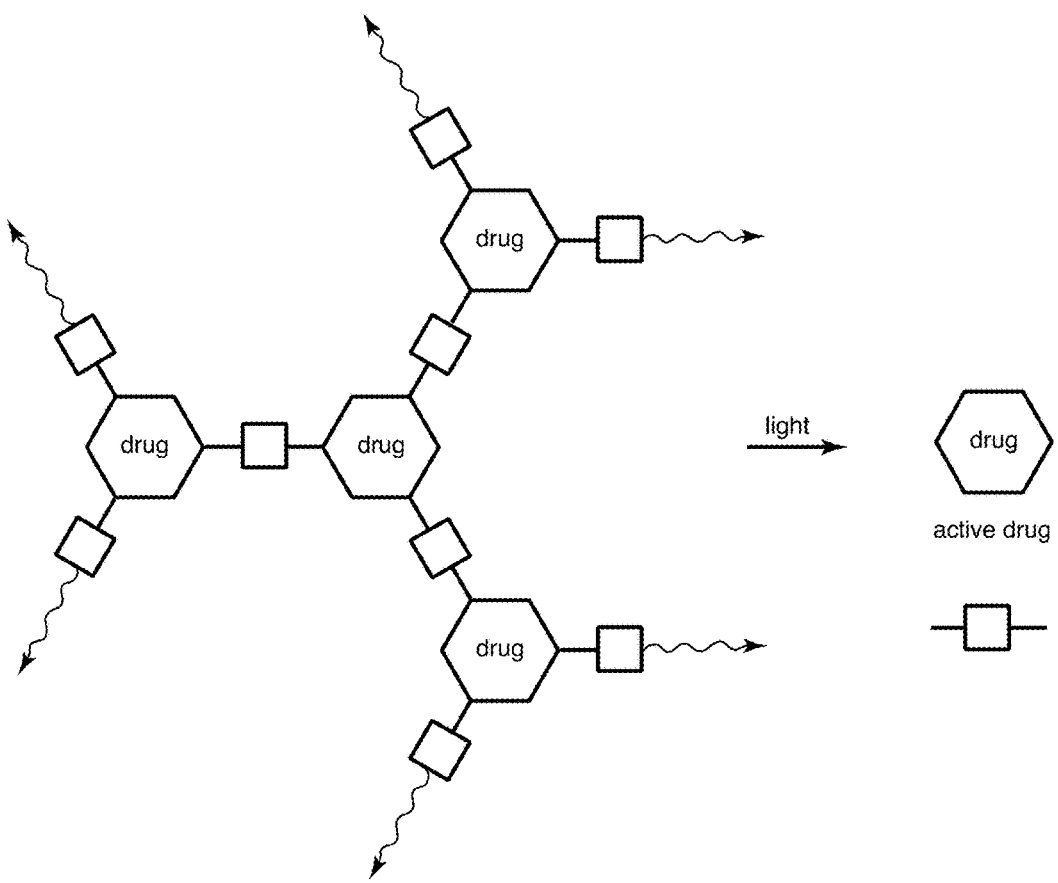

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the" include plural referents unless expressly and unequivocally limited to one referent. Thus, for example, reference to "a molecule" includes molecules.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The present invention is directed to two different, albeit related, approaches for allowing the controlled release of a drug with light. In the first approach (Approach A or the "linear" approach) involves a drug molecule linked to an insoluble polymer chain using a photocleavable linker. This approach is denominated as a "photocleavable drug-polymer conjugate." The insolubility of the polymer allows a depot of the polymer, photocleavable linker, and drug molecule to remain at a site of the injection until irradiation takes place. At that point, the drug is released from the conjugate and absorbed into the system. The polymer can then biodegrade, clearing it from the depot site.

In the second approach, (Approach B or the "meshwork" approach), the drug molecules are crosslinked to other drug molecules via photocleavable linkers. This approach is denominated as a "photocleavable drug conjugate." The drug molecules create the bulk of the conjugate through the creation of a three dimensional meshwork. Upon photolysis, the drug molecule is released from the conjugate.

Each of these two approaches will now be described in more detail.

Photocleavable Drug-Polymer Conjugates

In one aspect, the present invention is directed to a photocleavable drug-polymer conjugate. The photocleavable drug-polymer conjugate comprises a polymer chain linked via a photocleavable group to a drug molecule. The photocleavable drug-polymer conjugate can thus generally be described as:

Polymer-PC-Drug wherein Polymer is a polymer chain;

wherein PC is a photocleavable group; and wherein Drug is a drug molecule.

Multiple drug molecules may be loaded onto the polymer chain using the photocleavable group as a linker. Upon exposure to light of the appropriate wavelength, the drug molecule forming the conjugate is cleaved via photolysis, thereby releasing the drug from the conjugate. The desired drug release from the conjugate may also be modulated by controlling the intensity of the light exposure, duration of the light exposure, and the location of implantation.

The photocleavable drug-polymer conjugate is generally designed to function as a drug depot. The photocleavable drug-polymer conjugate is preferably formulated as a depot suitable for administration to sites beneath the skin of the patient, typically via cutaneous, subcutaneous, or intramuscular implantation. In general, the depot is an insoluble and solid or semi-solid (gel) use for delivery of drug to the body of a patient. The depot generally forms a mass to facilitate implantation and retention in a desired site of the patient. The depot can also be a liquid at room temperature that turns into a gel at body temperature, i.e., a thermosensitive gel.

The depot may have different sizes, shapes, and configurations. There are several factors that may be taken into consideration in determining the size, shape, and configuration of the depot. For example, both the size and shape may allow for ease in positioning the drug depot at the target tissue site that is selected as the implantation or injection site. In addition, the shape and size of the depot should be selected so as to minimize or prevent the drug depot from moving after implantation or injection. In various aspects, the drug depot may be shaped like a sphere, a cylinder such as a rod or fiber, a pellet, a flat surface such as a disc, film or sheet (e.g., ribbon-like) or the like. The drug depot may also have an amorphous or undefined shape. Flexibility may be a consideration so as to facilitate placement of the drug depot. The overall design of a suitable drug depot is well known to those skilled in the art. Exemplary sizes of the depot are about 0.05 to 60 mm in diameter (e.g., about 0.05, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, or 60 mm in diameter or some range therebetween).

There are a number of common locations within a patient that may be sites at which the drug depot may be implanted. For example, administration may be required in a patient's arms, shoulders, knees, hips, fingers, thumbs, neck, legs, abdomen, head, buttocks, feet, back, and/or spine.

The depot comprising the photocleavable drug-polymer conjugate of the present invention is generally implanted into the patient in need of delivery of the drug. The term "implantable" as utilized herein includes implantable through surgery, injection, or other suitable means. Typically, implantation is made cutaneously, subcutaneously, or intramuscularly using techniques generally known to those skilled in the art. In one aspect, the depot is located in the cutaneous region of the skin, for example, in the stratum germinativum and/or stratum spinosum of the epidermis. In another aspect, the depot is located in the dermis, for example in the papillary layer and/or the reticular layer. The patient may be implanted with a single depot or with an array of depots, e.g., such that smaller depots comprising the conjugate are implanted in a localized region.

The patient of the present invention is preferably an animal (for example, warm-blooded mammal) and may be either a human or a non-human animal. Exemplary non-human animals include but are not limited to non-human primates, rodents, farm animals (for example, cattle, horses, pigs, goats, and sheep) and pets (for example, dogs, cats, ferrets, and rodents). The patient is typically a mammal. The term "mammal" refers to organisms from the taxonomy class "mammalian," including but not limited to humans, chimpanzees, apes, orangutans, monkeys, rats, mice, cats, dogs, cows, horses, etc.

Figure 2A:
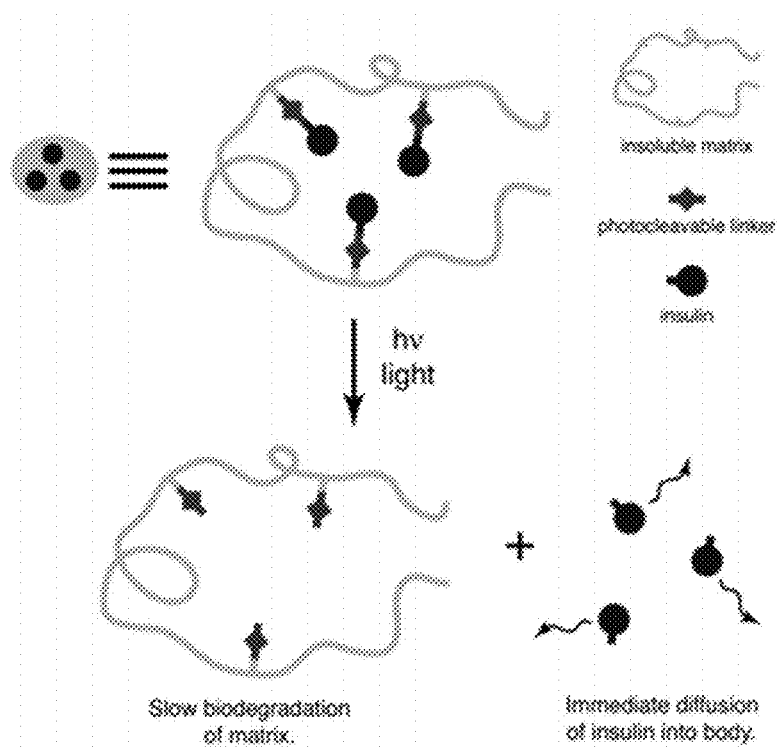
FIG. 2A shows insulin being linked to an insoluble, biocompatible, biodegradable, biosorbable polymer via a photocleavable group, and the effects of photolysis to release the insulin from the polymer chain.
Figure 2B:
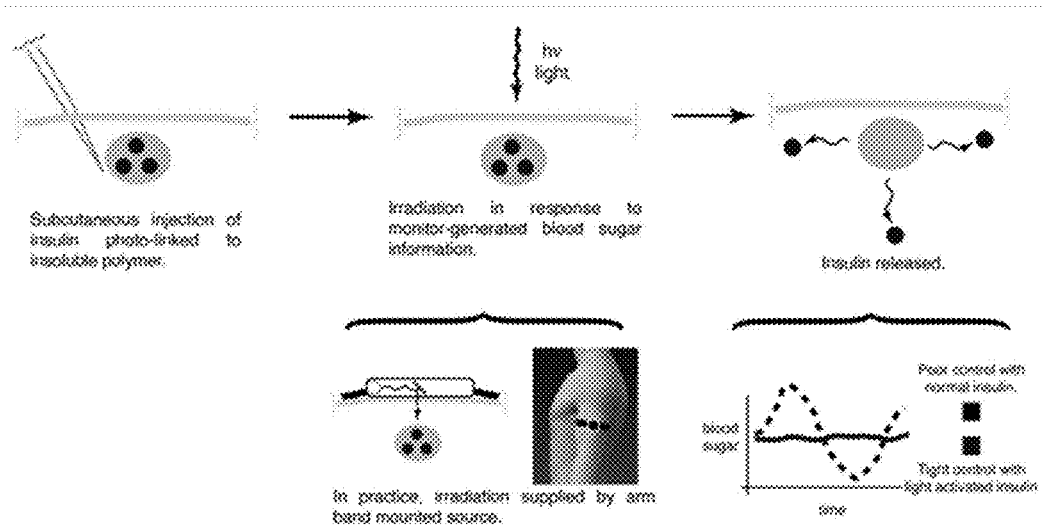
In FIG. 2B, the resulting photocleavable drug-polymer conjugate is injected cutaneously, subcutaneously, or intramuscularly in a manner similar to currently used with native insulin. In one aspect, the insulin in the conjugate forming the depot is released by transdermal irradiation in response to a physiological signal, for example, blood sugar information provided by the patient through traditional finger sticks or by one of the non-invasive monitoring methods known or being developed in the field.
Figure 3:
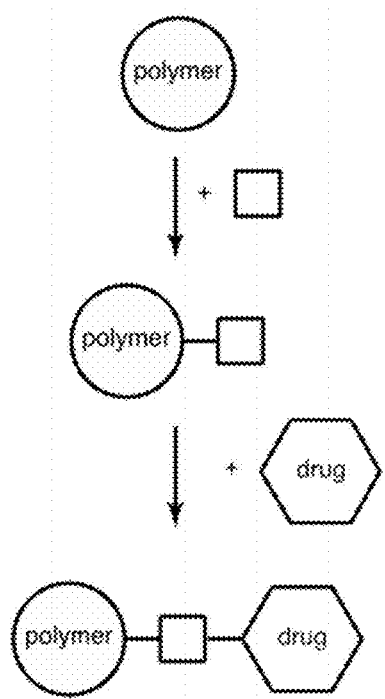
FIG. 3 schematically depicts two different approaches for synthesizing the linear or A conjugates shown in the overview of FIG. 1. The "sequential" or A1 approach involves the attachment of the photocleavable group to the polymer chain. The drug molecule is then attached to the photocleavable group. The link made between the drug molecule and the photocleavable group is such that upon photolysis, one drug molecule will be released. The drug molecule released may be in any active or prodrug form. The second method for making linear conjugates is a "convergent" method designated by A2 in FIG. 3. In this approach, the photocleavable group is attached to the drug molecule. This drug-photocleavable group precursor is then coupled with the polymer chain via a functional group on the polymer chain. The polymer may require multiple reactions to install the functional group that ultimately couples with the photocleavable group-drug conjugate. The advantage of the convergent A2 approach is that one can characterize the drug-photocleavable group precursor to ensure that the link has been made, which may be harder to do in the sequential A1 approach.
Figure 3:
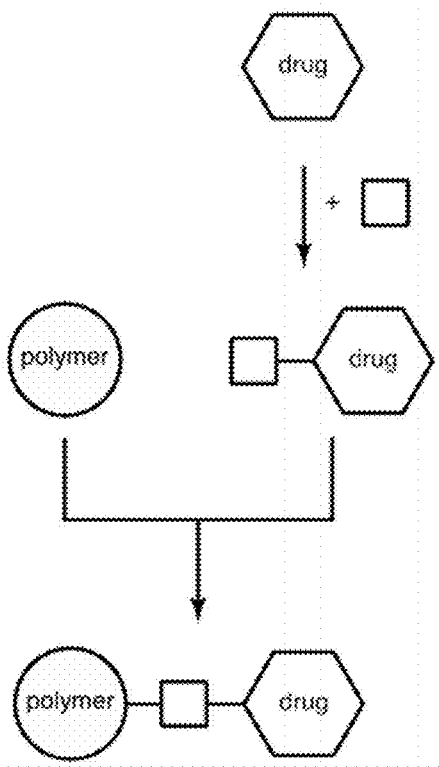

FIG. 2 illustrates one embodiment of the drug delivery system and method of the present invention. In this exemplary embodiment, the photocleavable drug-polymer conjugate comprises one or more insulin molecules(s) linked to a polymer chain via one or more photocleavable group(s). A drug depot comprising the photocleavable drug-polymer conjugate is implanted in a manner similar to currently used with native insulin. The depot generally takes the form of a matrix comprising the conjugate. The insulin in the depot is released by transdermal irradiation in response to a physiological signal, for example blood sugar information provided by the patient through traditional finger sticks or by one of the non-invasive monitoring methods being developed in the field.

The photocleavable drug-polymer conjugate of the present invention may provide immediate release of the drug, sustained release of the drug, or a combination thereof. For example, in general, immediate release of the drug may occur by irradiation of the photocleavable drug-polymer conjugate with appropriate light such that the drug is released from the photocleavable drug-polymer conjugate. This generally results into the introduction of the active drug into the body and that such that the drug is allowed to dissolve in or become absorbed at the location to which it is administered, with little or no delaying or prolonging of the dissolution or absorption of the drug. This concept is generally illustrated in FIG. 2.

As another example, once cleaved from the photocleavable drug-polymer conjugate, the drug may also undergo sustained release. In general, sustained release (also referred to as extended release or controlled release) encompasses ability of the photocleavable drug-polymer conjugate to continuously or continually release of the drug over a predetermined time period as a result of controlled irradiation with light. That is, the depot comprising photocleavable drug-polymer conjugate comprises a reservoir of drug molecules in which the release of the drug molecules from the conjugate may be photocontrolled over an extended period of time (e.g., days, weeks, or months).

Although the polymer forming the photocleavable drug-polymer conjugate is preferably biodegradable, the polymer is preferably such that degradation of the polymer is relatively minimal and slow over the lifetime of the depot. That is, unlike conventional depots in which the degradation of the polymer matrix forming the depot is often the primary mechanism which controls release of the drug over an extended period of time, the polymer forming the photocleavable drug-polymer conjugate is not generally the primary mechanism for controlled release. Instead, release of the drug is photocontrolled by exposing the depot to light of a suitable wavelength such that desired amount of the drug is cleaved from the conjugate and released from the depot.

The components of the photocleavable drug-polymer conjugate will now be described in more detail. In addition, the drug delivery methods and systems using the photocleavable drug-polymer conjugate will be further described.

Polymer Forming the Depot Matrix

The photocleavable drug-polymer conjugate comprises a polymer which typically forms a solid or semi solid matrix. The polymer is typically insoluble in order to limit dispersal at the site of implantation. The polymer generally functions as a backbone for attachment of the drug molecule(s) via the photocleavable group(s). The polymer is preferably biocompatible, biodegradable, and bioresorbable.

In one aspect, the polymer forming the matrix is preferably biocompatible. As used herein the term "biocompatible" means that the polymer (and thus the depot) will not cause substantial tissue irritation or necrosis at the target tissue site. Preferably, the polymer is approved for use in the body by the Food and Drug Administration.

In another aspect, the polymer forming the matrix is preferably biodegradable. As used herein, the term biodegradable generally refers to a base polymer that breaks down into oligomeric and/or monomeric units over a period of time, typically over days, weeks, or even months, when implanted or injected into the body of a mammal. Typically, the term "biodegradable" includes that all or parts of the drug depot will degrade over time by the action of enzymes, by hydrolytic action and/or by other similar mechanisms in the human body. "Biodegradable" generally means that the depot can break down or degrade within the body to non-toxic components after or while the drug has been or is being released.

In still another aspect, the polymer forming the matrix is preferably bioresorbable. As used here, the term bioresorbable refers to a polymer whose degradative products are metabolized in vivo or excreted from the body via natural pathways. In general, by "bioabsorbable," it is meant that the depot will be broken down and absorbed within the human body, for example, by a cell or tissue.

The polymer forming the matrix has a synthetic "handle," i.e., a reactive group or functionality that will allow it to be joined to a photocleavable group. It will be appreciated that there are a wide variety of possible functionalities that are possible in this regard. Exemplary reactive groups include, but are not limited to hydroxyl, amine, carboxyl, (such as carboxylic acid, amide, carboxylic halide, carboxylic acid ester or carboxylic acid anhydride, and the carboxyl group may be activated, as is well known in the art, to facilitate coupling), vinylsulfone, alkyne, azide, maleimide, isothiocyanate, isocyanate, imidate, alpha-halo-amide, Michael acceptor, hydrazide, oxyamine, thiol, hydrazine, or a combination thereof. The handle may be located within the polymer chain (including as a side chain extending from the primary chain) and/or at the terminal end of the polymer chain. High loading of the drug molecules onto the polymer chain may be achieved when the reactive groups are located along the polymer chain.

In one aspect, the polymer forming the matrix has a carboxylic acid functionality. In such a case, the polymer can be linked to the photocleavable group via an amine on the photocleavable group. That is, the polymer forming the matrix is linked to the photocleavable linker via an amide bond.

In one aspect, the polymer forming the matrix has an amine functionality. In such a case, the polymer can be linked to the photocleavable group via a carboxylic acid on the photocleavable group. That is, the polymer forming the matrix is linked to the photocleavable linker via an amide bond.

In another aspect, the polymer forming the matrix has an azide functionality. In such a case, the polymer can be linked to the photocleavable group via an alkyne on the photocleavable group. That is, the polymer forming the matrix is linked to the photocleavable linker via a triazole bridge.

In still another aspect, the polymer forming the matrix has an alkyne functionality. In such a case, the polymer can be linked to the photocleavable group via an azide on the photocleavable group. That is, the polymer forming the matrix is linked to the photocleavable linker via a triazole bridge.

It will be appreciated that one or more photocleavable groups may be linked to the polymer chain. For example, in the case of chitosan, the polymer comprises a chain of glycosamine molecules such that multiple amine functionalities on the polymer may be each linked to a photocleavable group. In turn, this provides for high loading of the drug molecules in such photocleavable drug-polymer conjugates.

Examples of suitable polymers include but are not limited to poly (alpha-hydroxy acids), poly (lactide-co-glycolide) ("PLGA"), polylactide ("PLA"), polyglycolide ("PG"), polyethylene glycol ("PEG"), conjugates of poly (alpha-hydroxy acids), polyorthoesters ("POE"), polyaspirins, polyphosphagenes, dendrimers, proteins, peptides, polysaccharides, collagen, starch, hyaluronic acid, chitosan, gelatin, alginates, albumin, and fibrin. Exemplary polymers are described in King, U.S. Patent Application No. 2011/0027340, which is incorporated by reference. Further, it will be appreciated that naturally occurring or synthetic polypeptides in either the L or D form (or a combination thereof) may be used as the polymer, especially those containing large numbers of acidic (e.g., aspartic acid, glutamic acid) or basic side chains (e.g., lysine). For example, homopolypeptides of poly-L-lysine, poly-D-lysine, poly-L-ornithine, poly-L-glutamic acid, poly-D-glutamic acid, poly-D,L-glutamic acid, and poly-L-aspartic acid are commercially available from Alamanda Polymers (Huntsville, Ala.). Exemplary peptides are about 20, 50, 100, 200, 400, 600, or 800 amino acids in length or some range therebetween.

In one aspect, the polymer is from the linear polyester family, such as polylactic acid, polyglycolic acid, or polycaprolactone and their associated copolymers, e.g., poly (lactide-co-glycolide) at all lactide to glycolide ratios, and both L-lactide or D,L lactide. Polymers such as polyorthoester, polyanhydride, polydioxanone, and polyhydroxybutyrate may also be employed.

In some aspects, the polymer forming the polymer matrix comprises about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 65%, 60%, 55%, 50%, 45%, 40%, 35%, 30%, 25%, 20%, 15%, 10%, 5%, 4%, 3%, 2%, 1% or some range therebetween based on the total weight of the depot and the remainder is active and/or inactive pharmaceutical ingredients.

Photocleavable Group

The photocleavable drug-polymer conjugate of the present invention comprises a photocleavable group. In general, the polymer forming the matrix of the depot is linked to one or more photocleavable groups, which are in turned linked to one or more drug molecules.

In one aspect, the photocleavable groups have at least two synthetic "handles" or reactive groups. The first reactive group allows linking of the photocleavable group to the polymer chain. The second reactive group allows linking of the photocleavable group to the drug molecule (such as insulin). The former handle is preferably stable and the latter handle is preferably amenable to photolysis such that the drug (e.g., insulin) cargo is released from the photocleavable drug-polymer conjugate upon exposure to light of the appropriate wavelength.

As discussed above, it will be appreciated that one or more photocleavable groups may be linked to the polymer chain. For example, in the case of chitosan, the polymer comprises a chain of glycosamine molecules such that multiple amine functionalities on the polymer chain may be each linked to a photocleavable group. As a result, multiple drug molecules may be loaded onto the polymer chain via the multiple photocleavable groups. For example, several insulin molecules may be loaded onto a single polymer chain of chitosan via several photocleavable groups. That is, the photocleavable drug-polymer conjugate comprises a single polymer chain linked to multiple photocleavable groups which are in turn linked to multiple drug molecules. In general, the drug depot may comprise a matrix of one or more of these photocleavable drug-polymer conjugates.

Alternatively, or in addition thereto, a single drug molecule may be loaded onto the polymer chain via multiple photocleavable groups. For example, in the case of chitosan, the polymer comprises a chain of glycosamine molecules such that multiple amine functionalities on the polymer chain may be each linked to a photocleavable group. As a result, a single drug molecule may be linked to the polymer chain via one or more of the photocleavable groups. For example, a single insulin molecule has several carboxyl-containing residues (e.g., Asp, Glu) and the multiple carboxyl functionalities could each be linked to a different photocleavable groups attached to the same chitosan polymer chain. That is, the photocleavable drug-polymer conjugate comprises a single polymer chain linked to multiple photocleavable groups such that a plurality (that is, two or more) of these photocleavable groups are linked to the same drug molecule. In general, the drug depot may comprise a matrix of one or more of these photocleavable drug-polymer conjugates.

Alternatively, or in addition thereto, a single drug molecule may be loaded onto multiple polymer chains via photocleavable groups. For example, in the case of chitosan, the polymer matrix comprises multiple polymer chains such that each polymer chain comprises a string of glycosamine molecules such that multiple amine functionalities on the chitosan polymer may be each linked to a photocleavable group. As a result, a single molecule of the drug may be linked to the multiple polymer chains within the matrix via one or more of the photocleavable groups attached to different polymer chains. For example, a single insulin molecule has several carboxyl functionalities (e.g., Asp, Glu) and one or more of these multiple carboxyl functionalities could each be linked to photocleavable groups attached to different chitosan polymer chains forming the matrix. That is, in one aspect, the photocleavable drug-polymer conjugate comprises a first polymer chain linked to one or more photocleavable group(s) which are in turn linked to one or more drug molecules, and some or all of those same drug molecules are also linked to a second polymer chain via other photocleavable crosslinking group(s). In general, the drug depot may comprise a matrix of one or more of these photocleavable drug-polymer conjugates.

In one aspect, the photocleavable group has a carboxylic acid functionality. In such a case, the polymer may be linked to the photocleavable group via an amine on the polymer forming the matrix. That is, the polymer forming the matrix may be linked to the photocleavable linker via an amide bond.

In one aspect, the photocleavable group has an amine functionality. In such a case, the polymer may be linked to the photocleavable group via a carboxylic acid on the polymer forming the matrix. That is, the polymer forming the matrix may be linked to the photocleavable linker via an amide bond.

In another aspect, the photocleavable group has an azide functionality. In such a case, the polymer may be linked to the photocleavable group via an alkyne on the polymer. That is, the polymer forming the matrix may be linked to the photocleavable linker via a triazole bridge.

In still another aspect, the photocleavable group has an alkyne functionality. In such a case, the polymer may be linked to the photocleavable group via an azide on the polymer. That is, the polymer forming the matrix may be linked to the photocleavable linker via a triazole bridge.

In another aspect, the photocleavable group has a diazo functionality. In such a case, the drug molecule (such as insulin) may be linked to the photocleavable group via a carboxylic acid functional group on the drug molecule. That is, the drug molecule may be linked to the photocleavable linker via an ester bond.

In another aspect, the photocleavable group has an N-hydroxy succinamide ("NHS") ester functionality. The drug molecule may be linked to the photocleavable group via an amine on the drug molecule. That is, the drug molecule may be linked to the photocleavable linker via a carbamate/urethane bond.

In another aspect, the photocleavable group has an imidazole functionality. The drug molecule may be linked to the photocleavable group via an amine on the drug molecule. That is, the drug molecule may be linked to the photocleavable linker via a carbamate bond.

In general, the photocleavable group should also have minimal toxicity. The photochemical properties of the photocleavable groups include any agent which may be linked to the drug molecule and which, upon exposure to light, releases the drug in functional form (or a suitable prodrug form). In general, groups capable of longer wavelength photolysis will show more efficient cleavage at deeper levels.

Exemplary photocleavable groups are generally described and reviewed in Pelliccioli et al., *Photoremovable protecting groups: reaction mechanisms and applications,* Photochem. Photobiol. Sci. 1 441-458 (2002); Goeldner and Givens, Dynamic Studies in Biology, Wiley-VCH, Weinheim (2005); Marriott, Methods in Enzymology, Vol. 291, Academic Press, San Diego (1998); Morrison, Bioorganic Photochemistry, Vol. 2, Wiley, New York (1993); Adams and Tsien, Annu. Rev. Physiol. 55 755-784 (1993); Mayer et al., *Biologically Active Molecules with a "Light Switch,"* Angew. Chem. Int. Ed. 45 4900-4921 (2006); Pettit et al., Neuron 19 465-471 (1997); Furuta et al., *Brominated 7-hydroxycoumarin-4-ylmethyls: Photolabile protecting groups with biologically useful cross-sections for two photon photolysis,* Proc. Natl. Acad. Sci. USA 96 1193-1200 (1999); and U.S. Pat. Nos. 5,430,175; 5,635,608; 5,872,243; 5,888,829; 6,043,065; and Zebala, U.S. Patent Application No. 2010/0105120, the disclosures of which are incorporated by reference herein.

The photocleavable group may generally be described as a chromophore. Examples of chromophores which are photoresponsive to such wavelengths include, but are not limited to, acridines, nitroaromatics, and arylsulfonamides. The efficiency and wavelength at which the chromophore becomes photoactivated and thus releases the drug will vary depending on the particular functional group(s) attached to the chromophore. For example, when using nitroaromatics, such as derivatives of o-nitrobenzylic compounds, the absorption wavelength can be significantly lengthened by addition of methoxy groups.

In one aspect, the photocleavable group is a nitro-aromatic compound. Exemplary photocleavable groups having an ortho-nitro aromatic core scaffold include, but are not limited to, ortho-nitro benzyl ("ONB"), 1-(2-nitrophenyl)ethyl ("NPE"), alpha-carboxy-2-nitrobenzyl ("CNB"), 4,5-dimethoxy-2-nitrobenzyl ("DMNB"), 1-(4,5-dimethoxy-2-nitrophenyl)ethyl ("DMNPE"), 5-carboxymethoxy-2-nitrobenzyl ("CMNB") and ((5-carboxymethoxy-2-nitrobenzyl)oxy)carbonyl ("CMNCBZ") photolabile cores. It will be appreciated that the substituents on the aromatic core are selected to tailor the wavelength of absorption, with electron donating groups (e.g., methoxy) generally leading to longer wavelength absorption. For example, nitrobenzyl ("NB") and nitrophenylethyl ("NPE") are modified by addition of two methoxy residues into 4,5-dimethoxy-2-nitrobenzyl and 1-(4,5-dimethoxy-2-nitrophenyl)ethyl, respectively, thereby increasing the absorption wavelength range to 340-360 nm.

Further, other ortho-nitro aromatic core scaffolds include those that trap nitroso byproducts in a hetero Diels Alder reaction as generally discussed in Zebala, U.S. patent application No. 2010/0105120 and Pirrung et al., J. Org. Chem. 68:1138 (2003). The nitrodibenzofurane ("NDBF") chromophore offers an extinction coefficient significantly higher in the near UV region but it also has a very high quantum yield for the deprotection reaction and it is suitable for two-photon activation (Momotake et al., *The nitrodibenzofuran chromophore: a new caging group for ultra-efficient photolysis in living cells*, Nat. Methods 3 35-40 (2006)). The NPP group is an alternative introduced by Pfleiderer et al. that yields a less harmful nitrostyryl species (Walbert et al., *Photolabile Protecting Groups for Nucleosides: Mechanistic Studies of the 2-(2-Nitrophenyl)ethyl Group*, Helv. Chim. Acta 84 1601-1611 (2001)).

In an exemplary aspect involving UV light, the photocleavable group is selected from the group consisting of alpha-carboxy-2-nitrobenzyl (CNB, 260 nm), 1-(2-nitrophenyl)ethyl (NPE, 260 nm), 4,5-dimethoxy-2-nitrobenzyl (DMNB, 355 nm), 1-(4,5-dimethoxy-2-nitrophenyl)ethyl (DMNPE, 355 nm), (4,5-dimethoxy-2-nitrobenzoxy)carbonyl (NVOC, 355 nm), 5-carboxymethoxy-2-nitrobenzyl (CMNB, 320 nm), ((5-carboxymethoxy-2-nitrobenzyl)oxy) carbonyl (CMNCBZ, 320 nm), desoxybenzoinyl (desyl, 360 nm), and anthraquino-2-ylmethoxycarbonyl (AQMOC, 350 nm).

Other suitable photocleavable groups are based on the coumarin system, such as BHC (Furuta and Iwamura, Methods Enzymol. 291 50-63 (1998); Furuta et al., Proc. Natl. Acad. Sci. USA 96 1193-1200 (1999); Suzuki et al., Org. Lett. 5:4867 (2003); U.S. Pat. No. 6,472,541, the disclosure of which is incorporated by reference herein). The DMACM linkage photocleaves in nanoseconds (Hagen et al., *[7-(Dialkylamino)coumarin-4-yl]methyl-Caged Compounds as Ultrafast and Effective Long-Wavelength Phototriggers of 8-Bromo-Substituted Cyclic Nucleotides*, Chem Bio Chem 4 434-442 (2003)) and is cleaved by visible light (U.S. patent application Ser. No. 11/402,715 the disclosure of which is incorporated by reference herein). Coumarin-based photolabile linkages are also available for linking to aldehydes and ketones (Lu et al., *Bhc-diol as a photolabile protecting group for aldehydes and ketones*, Org. Lett. 5 2119-2122 (2003)). Closely related analogues, such as BHQ, are also suitable (Fedoryak et al., *Brominated hydroxyquinoline as a photolabile protecting group with sensitivity to multiphoton excitation*, Org. Lett. 4 3419-3422 (2002)). Another suitable photocleavable group comprises the pHP group (Park and Givens, J. Am. Chem. Soc. 119:2453 (1997), Givens et al., *New Phototriggers 9: p-Hydroxyphenacyl as a C-Terminal Photoremovable Protecting Group for Oligopeptides*, J. Am. Chem. Soc. 122 2687-2697 (2000); Zhang et al., J. Am. Chem. Soc. 121 5625-5632, (1999); Conrad et al., J. Am. Chem. Soc. 122 9346-9347 (2000); Conrad et al., Org. Lett. 2 1545-1547 (2000)). A ketoprofen derived photolabile linkage is also suitable (Lukeman et al., *Carbanion-Mediated Photocages: Rapid and Efficient Photorelease with Aqueous Compatibility*, J. Am. Chem. Soc. 127 7698-7699 (2005)).

As discussed above, a photocleavable group is one whose covalent attachment to a drug molecule is reversed (cleaved) by exposure to light of an appropriate wavelength. In one aspect, release of the drug molecule occurs when the conjugate is subjected to ultraviolet light. For example, photorelease of the drug molecule may occur at a wavelength ranging from about 200 to 380 nm (the exact wavelength or wavelength range will depend on the specific photocleavable group used, and could be, for example, 200, 210, 220, 230, 240, 250, 260, 270, 280, 290, 300, 310, 320, 330, 340, 350, 360, 370, or 380 or some range therebetween). In another aspect, release of the drug molecule occurs when the conjugate is subjected to visible light. For example, photorelease of the drug molecule may occur at a wavelength ranging from about 380 to 780 nm (the exact wavelength or wavelength range will depend on the specific photocleavable group used, and could be, for example, 380, 400, 450, 500, 550, 600, 650, 700, 750, or 780, or some range therebetween). In still another aspect, release of the drug molecule occurs when the conjugate is subjected to infrared light. For example, photorelease of the drug molecule may occur at a wavelength ranging from about 780 to 1200 nm (the exact wavelength or wavelength range will depend on the specific photocleavable group used, and could be for example, 780, 800, 850, 900, 950, 1000, 1050, 1100, 1150, or 1200, or some range therebetween). In general, longer wavelengths are preferred because they provide for greater tissue penetration and generally exhibit less toxicity. To avoid premature photorelease of the drug molecule, the depot may be shielded from background/ambient light using any suitable device, such as a patch, bandage, band, and the like.

In one aspect, the photocleavable group may be a diazoazide. For example, the photocleavable functional group may be defined according to:

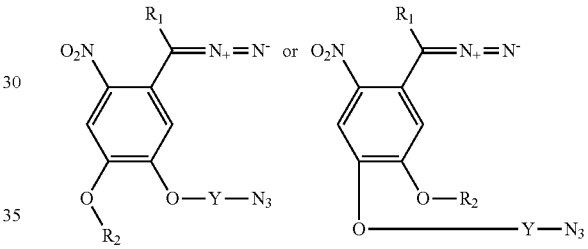

wherein $R_1$ is H or alkyl (preferably a $C_1$-$C_6$ alkyl); $R_2$ is H or alkyl (preferably a $C_1$-$C_6$ alkyl) and Y is a linker chain (preferably a linker chain comprising about 1 to 100 atoms). The linker may comprise C, N, O, S, and/or P atoms, and may comprise 5, 10, 15, 20, 25, 30, 35, 40, 45, 50, 55, 60, 65, 70, 75, 80, 85, 90, 95, or 100 atoms. Exemplary linkers include alkyl or polyether groups.

In another aspect, the photocleavable group may be a diazo-alkyne. For example, the photocleavable functional group may be defined according to:

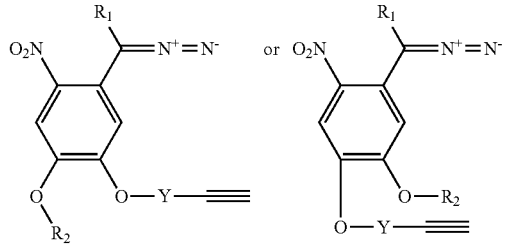

wherein $R_1$ is H or alkyl (preferably a $C_1$-$C_6$ alkyl); $R_2$ is H or alkyl (preferably a $C_1$-$C_6$ alkyl); and Y is a linker chain (preferably a linker chain comprising about 1 to 100 atoms). The linker may comprise C, N, O, S, and/or P atoms, and may comprise 5, 10, 15, 20, 25, 30, 35, 40, 45, 50, 55, 60, 65, 70, 75, 80, 85, 90, 95, or 100 atoms. Exemplary linkers include alkyl or polyether groups.

Drug

The photocleavable drug-polymer conjugate of the present invention comprises a one or more drug molecules. In general, the term "drug" as used herein refers to any substance that alters the physiology of a patient. The term "drug" may be used interchangeably herein or in the art with the terms "biologically active agent," "therapeutic agent," and "active pharmaceutical ingredient" or prodrug thereof as known in the art. Thus, the "drug" that is photoreleased from the conjugate may be a drug, drug precursor or modified drug that is not fully active or available until converted in vivo to its therapeutically active or available form. The drug may include small molecule compounds, peptides, proteins, or any other medicament or medicine used in the treatment or prevention of a disease or condition. Representative non-limiting classes of drugs useful in the present invention include those falling into the following therapeutic categories: ACE-inhibitors; anti-anginal drugs; anti-arrhythmias; anti-asthmatics; anti-cholesterolemics; anti-convulsants; anti-depressants; anti-diarrhea preparations; anti-histamines; anti-hypertensive drugs; anti-infectives; anti-inflammatory agents; anti-lipid agents; anti-manics; anti-nauseants; anti-stroke agents; anti-thyroid preparations; anti-tumor drugs; anti-tussives; anti-uricemic drugs; anti-viral agents; acne drugs; alkaloids; amino acid preparations; anabolic drugs; analgesics; anesthetics; angiogenesis inhibitors; antacids; anti-arthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migraine treatments; mineral supplements; mucolytics; narcotics; neuroleptics; neuromuscular drugs; NSAIDS; nutritional additives; peripheral vasodilators; polypeptides; prostaglandins; psychotropics; renin inhibitors; respiratory stimulants; steroids; stimulants; sympatholytics; thyroid preparations; tranquilizers; uterine relaxants; vaginal preparations; vasoconstrictors; vasodilators; vertigo agents; vitamins; and wound healing agents.

The preferred drugs molecules used in the present invention are those which are very potent such that they require relatively small amounts for the desired therapeutic effect but also need the blood levels to be carefully controlled. The preferred drugs are also those which benefit from good control of release.

In one aspect, the drug molecule is a therapeutic peptide or protein, such as those described in Bossard et al., U.S. patent application No. 2011/0166063 and Ekwuribe, U.S. Pat. No. 6,858,580, which are both incorporated by reference. Preferred therapeutic peptides and proteins are selected from the group consisting of insulin; glucagon; calcitonin; gastrin; parathyroid hormones; angiotensin; growth hormones; secretin; luteotropic hormones (prolactin); thyrotropic hormones; melanocyte-stimulating hormones; thyroid-stimulating hormones (thyrotropin); luteinizing-hormone-stimulating hormones; vasopressin; oxytocin; protirelin; peptide hormones such as corticotropin; growth-hormone-stimulating factor (somatostatin); G-CSG, erythropoietin; EGF; physiologically active proteins, such as interferons and interleukins; superoxide dismutase and derivatives thereof; enzymes such as urokinases and lysozymes; and analogues or derivatives thereof. In another aspect, the therapeutic peptide or protein is selected from the group consisting of human growth hormone, bovine growth hormone, growth hormone-releasing hormone, an interferon, interleukin-1, interleukin-II, insulin, calcitonin, erythropoietin, atrial natriuretic factor, an antigen, a monoclonal antibody, somatostatin, adrenocorticotropin, gonadotropin releasing hormone, oxytocin, vasopressin, analogues, or derivatives thereof In another aspect, the drug molecule is an anti-diabetic agent already in the clinical practice or in the pipeline of development. The anti-diabetic drug molecules are broadly categorized herein as insulin/insulin analogs and non-insulin anti-diabetic drugs. The non-insulin anti-diabetic drugs may include, but not limited to, insulin sensitizers, such as biguanides (e.g., metformin, buformin, phenformin, and the like), thiazolidinedione (TZDs; e.g., pioglitazone, rivoglitazone, rosiglitazone, troglitazone, and the like), and dual peroxisome proliferator-activated receptor agonists (e.g., aleglitazar, muraglitazar, tesaglitazar, and the like). The non-insulin anti-diabetic drugs may also include, but not limited to, secretagogues, such as sulfonylureas (e.g., carbutamide, chlorpropamide, gliclazide, tolbutamide, tolazamide, glipizide, glibenclamide, gliquidone, glyclopyramide, glimepiride, and the like), meglitinides (e.g., nateglinide, repaglinide, mitiglinide, and the like), GLP-1 analogs (e.g., exenatide, liraglutide, albiglutide, taspoglutide, and the like), and dipeptidyl peptidase 4 inhibitors (e.g., alogliptin, linagliptin, saxagliptin, sitagliptin, vildagliptin, and the like). Further, the non-insulin anti-diabetic drugs may include, but not limited to, alpha-glucosidase inhibitors (e.g., acarbose, miglitol, voglibose, and the like), amylin analog (e.g., pramlintide and the like), SGLT2 inhibitors (e.g., dapagliflozin, remogliflozin, sergliflozin, and the like), benfluorex, and tolrestat.

In a preferred aspect, the drug molecule is insulin. As used herein, the term insulin embraces analogues or derivatives thereof. Exemplary insulin compounds are described in Foger et al., U.S. Published Patent No. 2011/0144010, which is incorporated by reference.

In another aspect, the drug is insulin (or an analog or derivative thereof) in its hexameric form, typically in the presence of zinc.

In an exemplary aspect, the carboxyl functionalities found on insulin are able to form a photolabile bond with a photocleavable group having a DMNPE group. Upon photolysis, the carboxyl functionality is released from the DMNPE, generating native insulin. It will be appreciated that amine or other functional groups on insulin be used to form a photolabile bond with the photocleavable group.

Additional Considerations

The photocleavable drug-polymer conjugate of the present invention may be modified in various ways. For example, one or more linkers may be used to vary the distance between polymer chain and photocleavable group. Likewise, one or more linkers may be used to vary the distance between photocleavable group and the drug molecule. The linker length may be 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, or 50 atoms (e.g., carbons) long. The linker may be comprised of carbon, nitrogen, oxygen, sulfur, and phosphorous atoms. For example, the linker may be an alkyl or contain ether, ester, and/or amines groups. In addition, the polymer chain may be crosslinked to stabilize the polymer itself.

Depot Formulations

The photocleavable drug-polymer conjugate of the present invention is formulated into a depot. It will be appreciated to those skilled in the art that the depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, the depot may comprise sterile preservative free material.

In one aspect, the drug depot includes one or more viscosity enhancing agents, such as, for example, hydroxypropyl cellulose, hydroxypropyl methyl cellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate ("PMMA"), methylmethacrylate ("MMA"), gelatin, polyvinyl alcohols, propylene glycol; PEG 200, PEG 300, PEG 400, PEG 500, PEG 600, PEG 700, PEG 800, PEG 900, PEG 1000, PEG 1450, PEG 3350, PEG 4500, PEG 8000, or combinations thereof.

Drug Delivery

The depot comprising the photocleavable drug-polymer conjugate is typically administered to the target site of the patient using a "cannula" or "needle" that can be a part of a drug delivery device, e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. The cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. The cannula or needle may also be non-coring and have a sheath covering it to avoid unwanted needle sticks. The dimensions of the hollow cannula or needle, among other things, will depend on the site for implantation.

Once implanted into the patient, the depot comprising the photocleavable drug-polymer conjugate provides for immediate and/or controlled release of the drug using light activation. Further, in the present invention, there is a potential for rapid (e.g., real time or even minute by minute) correction of blood sugar levels through the non-invasive and continuously variable release of insulin with light. In one aspect, native like, rock-level blood sugar levels of a non-diabetic could potentially be obtained.

In one aspect, irradiation is accomplished by a light source located external to the patient. The external light source may be possibly worn like an band, patch, or bandage over the depot site. The irradiation to promote photorelease of the drug can be provided by a variety of sources including, but not limited to light emitting diodes (LEDs), lasers, and even incandescent, fluorescent, or ultraviolet bulbs. Various phototherapy devices are known in the art and could be readily adapted for use in the present invention. For example, there are many commercially phototherapy devices uses for the treatment of psoriasis, wound repair, and other skin diseases (such as those manufactured by TheraLight, Inc.) which could be modified for use in the present invention. Other exemplary phototherapy devices include, but are not limited to those described in Passy et al., U.S. Pat. No. 7,513,906; Parker et al., U.S. Pat. No. 7,686,839; Hubert et al., U.S. Pat. No. 7,878,203; Gertner et al. U.S. Published Application No. 2006/0206173; Lewis, U.S. Published Application No. 2008/0269849; Holloway et al. U.S. Published Application No. 2004/0166146; all of which are incorporated by reference.

The light-emitting device provides irradiation to the skin surface of the patient in the area overlying the depot sufficient penetrate the tissue overlying the conjugate. The light results in the photorelease of the desired amount of drug molecules from the conjugate. Broadly speaking, the light-emitting device thus provides for "transdermal" irradiation of the depot although the depot may be located cutaneously, subcutaneously, or intramuscularly, as generally described herein.

The light-emitting device may include a controller or computer programmed to irradiate the skin of the patient in a number of different ways. The irradiation may be provided at fixed or variable intervals. For example, for drugs requiring conventional twice per day ("BID") or three times per day ("TID") dosing, the light emitting device may be programmed to provide irradiation two or three times per day, respectively. Alternatively, the light emitting device may be coupled to a sensor which measures a variable dependent upon the drug concentration in the body and then provides feedback to the light emitting device to control the light irradiation. For example, in the case of insulin, the light emitting device may be coupled to a sensor which measures the amount of insulin in the blood stream or other parameter (most likely the blood glucose concentration). The light emitting device may be programmed to irradiate the skin of the patient in accordance with that feedback loop. In short, the amount of light generated from the light emitting device can be periodically or continually modulated depending on the desired outcome. Sensors and other devices for measuring the dependent variable of interest (such as blood glucose) are generally described in Jennewine, U.S. Published Application No. 2009/0054750; Hayter et al., U.S. Published Application No. 2009/0164239; Blomquist, U.S. Published Application No. 2008/0172031; Talbot et al., U.S. Published Application No. 2005/0065464; all of which are all incorporated by reference.

Combination or Multi-Drug Delivery

The depots of the present invention comprise one or more photocleavable drug-polymer conjugates. The photocleavable drug-polymer conjugate used in the depot may be comprised of different polymers types, different photocleavable group types, different drug molecule types, or a combination thereof. Thus, the depots of the present invention are well adapted to the administration of multiple drugs types.

In one aspect, the depot comprises a first photocleavable drug-polymer conjugate comprising a first polymer chain linked to a first photocleavable group which is in turn linked to a first drug molecule. The depot may also comprise a second photocleavable drug-polymer conjugate comprising a second polymer chain linked to a second photocleavable group which is in turn linked to a second drug molecule. The first and second polymer chains may be of the same or different type. The first and second photocleavable groups are of a different type, and the first and second drug molecules are of a different type. The excitation wavelength may be chosen so as to selectively excite and cleave the particular photocleavable groups. As a result, independent control of the release of the first drug and the second drug from the depot may be achieved.

As an example of the foregoing, the depot may comprise a first photocleavable drug-polymer conjugate comprising chitosan polymers linked to insulin via a NDBF group. The depot may also comprise a second photocleavable drug-polymer conjugate comprising chitosan polymers linked to glipizide via a NPE group. The depot may be irradiated with two different wavelengths (e.g., one that cleaves NDBF and another wavelength that cleaves NPE) either simultaneously or sequentially in order to control the release of the two drug types.

In another aspect, the depot comprises a photocleavable drug-polymer conjugate comprising a polymer chain having a first photocleavable group linked to a first drug molecule and the same polymer chain having a second photocleavable group linked to a second drug molecule. The first and second photocleavable groups are of a different type, and the first and second drug molecules are of a different type. The excitation wavelength may be chosen so as to selectively excite the particular photocleavable groups. As a result, independent control of the release of the first drug and the second drug from the depot may be achieved.

As an example of the foregoing, the depot may comprise a photocleavable drug-polymer conjugate comprising a chitosan polymer chain linked to insulin via a NDBF group and glipizide linked to the same chitosan polymer chain via a NPE group. The depot may be irradiated with two different wavelengths (e.g., one that cleaves NDBF and another that cleaves NPE) either simultaneously or sequentially in order to control the release of the two drugs.

From the foregoing, it is contemplated that it is possible to photoreleasably attach multiple different drug molecule types and/or different photocleavable group types to the polymer chain(s), and then independently control the photorelease of the drugs by selecting the excitation wavelength to match the corresponding photocleavable groups.

Photocleavable Drug Conjugates

In another broad aspect, the present invention is directed to a photocleavable drug conjugate. The photocleavable drug conjugate does not comprise a polymer chain. Instead, the drug molecules are crosslinked with the photocleavable groups. The photocleavable drug conjugate is preferably designed to function as a drug depot. The photocleavable drug conjugate is formulated as a depot suitable for cutaneous, subcutaneous, or intramuscular implantation. Suitable drugs and photocleavable groups for forming the photocleavable drug conjugate are discussed above. The preferred drugs molecules are polymers having multiple amine, carboxyl, and/or thiol groups, such as therapeutic peptides, and the most preferred drug is insulin. In one aspect, the drug is insulin (or an analog or derivative thereof) in its hexameric form, typically in the presence of zinc.

As generally illustrated in FIG. 1B, the light activated system is formed by crosslinking insulin with photocleavable groups which also generally function as crosslinkers. One major advantage of the approach shown in FIG. 1B is that the depot is likely mostly insulin, and not polymer carrier, thus likely increasing the total aggregate duration of action of a given depot. Typically, the ratio of drug to the photocleavable crosslinker is about 95:5, 90:10, 80:20, 70:30, 60:40, 50:50, 40:60, 30:70, 20:80, 10:90, or 5:95 or some range therebetween. In addition, in this embodiment, there is no need for biodegradation of a polymer after the depot releases its drug cargo.

Crosslinking may be achieved by using photocleavable groups that are capable of crosslinking insulin or additional linkers may be added to facilitate crosslinking (such as alkyne platform linkers). For example, in one aspect, the photocleavable groups in this embodiment have at least two synthetic "handles" or reactive functional groups that permit crosslinking of the drug molecules. At least one of the handles (preferably both) are amenable to photolysis such that the drug (e.g., insulin) cargo is released from the photocleavable drug conjugate upon exposure to light.

In one aspect, the photocleavable group used for crosslinking in this embodiment may be a bifunctional or multifunctional photocleavable group such that photolysis occurs at two or more places in the linker. In some aspects, the photocleavable group may be constructed as a dimer, trimer, or other -mer such that the "mer" units forming the photocleavable group are each photocleavable.

In one aspect, the photocleavable group may be a diazo-multimer. For example, the photocleavable functional group may be defined according to:

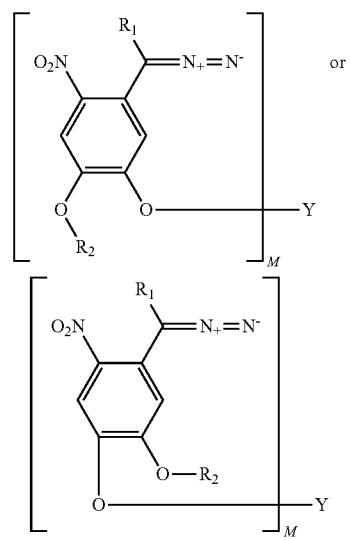

wherein $R_1$ is H or alkyl (preferably a $C_1$-$C_6$ alkyl); $R_2$ is H or alkyl (preferably a $C_1$-$C_6$ alkyl); and Y is a linker chain (preferably a linker chain comprising about 1 to 100 atoms); and M is an integer (preferably 2, 3, 4, or 5). The linker may comprise C, N, O, S, and/or P atoms, and may comprise 5, 10, 15, 20, 25, 30, 35, 40, 45, 50, 55, 60, 65, 70, 75, 80, 85, 90, 95, or 100 atoms. Exemplary linkers include alkyl or polyether groups.

In another aspect, the photocleavable group may be a carbonate-multimer. For example, the photocleavable functional group may be defined according to:

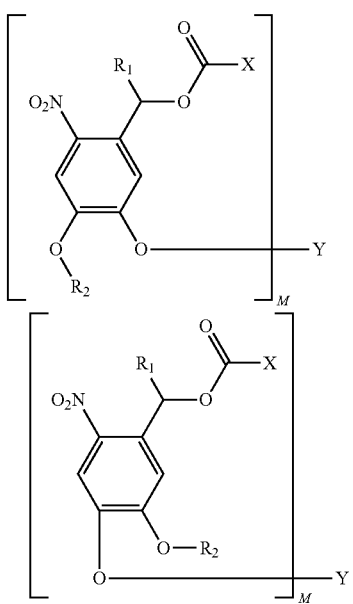

wherein $R_1$ is H or alkyl (preferably a $C_1$-$C_6$ alkyl); $R_2$ is H or alkyl (preferably a $C_1$-$C_6$ alkyl); X is a leaving group (such as N-hydroxyl succinimide); Y is a linker chain (preferably a linker chain comprising about 1 to 100 atoms); and M is an integer (preferably 2, 3, 4, or 5). The linker may comprise C, N, O, S, and/or P atoms, and may comprise 5, 10, 15, 20, 25, 30, 35, 40, 45, 50, 55, 60, 65, 70, 75, 80, 85, 90, 95, or 100 atoms. Exemplary linkers include alkyl or polyether groups.

The drug molecule has at least two reactive functional groups that are suitable for crosslinking. It will be appreciated that while the crosslinking strategy may used with some small molecule drugs (or prodrugs) having reactive functional groups, this embodiment is particularly well suited for crosslinking of peptides, proteins, nucleic acids, and other macromolecules. Peptides having about 10 to 500 amino acid residues (e.g., about 10, 20, 30, 40, 50, 60, 70, 80, 90, 100, 150, 200, 250, 300, 350, 400, 450, or 500 residues or some range therebetween) are most preferred.

As with the prior embodiment, the photocleavable drug conjugate of this embodiment of present invention is formulated into a depot. It will be appreciated to those skilled in the art that the depot may optionally contain inactive materials, such as those discussed herein, for example, one or more viscosity enhancing agents. Further, the depot may be delivered to the target site of the patient as generally described above for the prior embodiment. Irradiation of the depot may also be achieved as generally described herein.

Once implanted into the patient, the depot comprising the photocleavable drug conjugate provides for release of the drug from the conjugate using light activation. Because the drug molecules (such as insulin) are crosslinked, photolysis may result in the release of a smaller aggregate or "island" of the photocleavable drug conjugate. For example, if the depot comprises a photocleavable drug conjugate having 100 photocleavable crosslinked insulin molecules, photolysis may result in cleavage such that a smaller aggregate comprising 2 to 10 (e.g., 2, 3, 4, 5, 6, 7, 8, 9, or 10 ) photolabile crosslinked insulin molecules are formed. In many instances, this aggregate will still have a therapeutic effect. In addition, or alternatively, the aggregate may bio-degrade to release individual insulin molecules upon absorption by and/or distribution into the body.

Other Crosslinking Groups

In one aspect, the photocleavable drug conjugate comprises photocleavable groups which may also be cleaved using other mechanisms. Preferably, the linker is cleaved under mild conditions, i.e., conditions within a cell under which the activity of the drug is not affected. Examples of suitable cleavable linkers include disulfide linkers, acid labile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Peptidase labile linkers can be used to cleave certain peptides inside or outside cells. Photolysis may result the release of a smaller aggregate of the crosslinked drug conjugate. In turn, these smaller aggregates may form even smaller aggregates or individual drug molecules as generally described herein.

For example, the photocleavable group may comprise a carbamate linkage to the drug molecule. The carbamate can be both photolyzed to release the drug and can also be cleaved by esterases to produce native insulin. If an aggregate of crosslinked drug molecules is photocleaved and released from the main portion of the drug depot, the drug molecules in this smaller aggregate may still be released by esterases within the body as the aggregate is absorbed by and/or distributed therein. However, in general, this esterase action will be limited when the carbamate link resides within the main depot since there will be limited access to esterases at the depot site.

The present invention will now be described with reference to the following examples. It should be appreciated that these examples are for the purposes of illustrating aspects of the present invention, and do not limit the scope of the invention as defined by the claims.

EXAMPLE 1

Linear, Sequential (A1)

Figure 4:
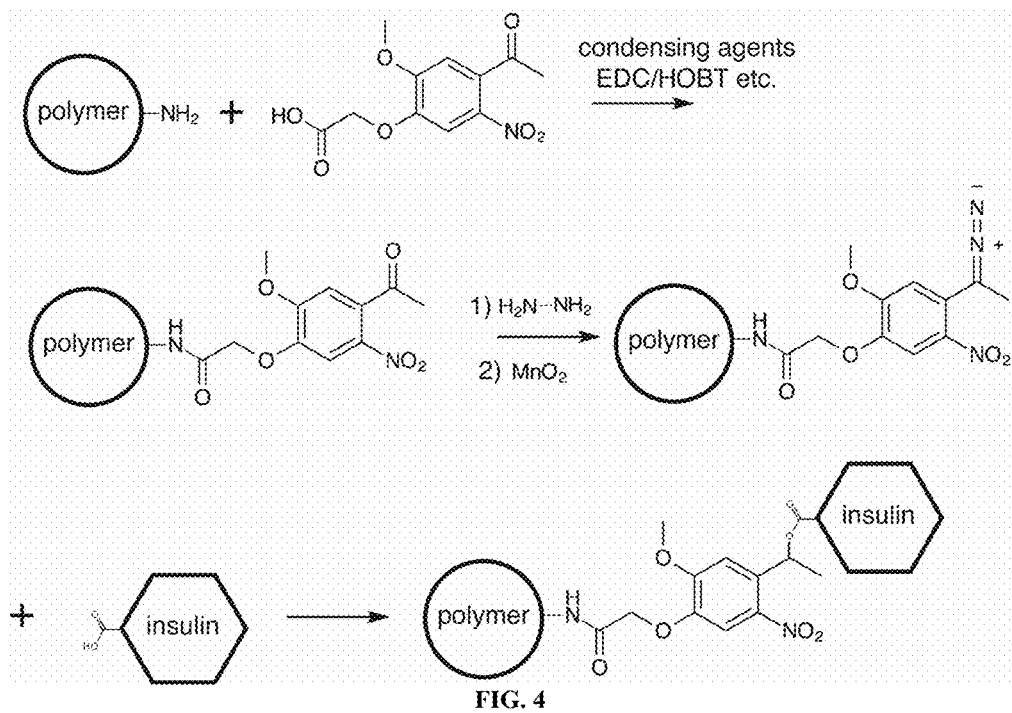
FIG. 4 shows an exemplary linear sequential synthesis approach for the preparation of an exemplary photocleavable drug-polymer conjugate. An insoluble polymer (shown as an enlarged circle) is linked to a photocleavable group using a condensation reaction. A ketone functionality on the photocleavable group is converted to a diazo group in two steps. In the first step, ketone is converted into hydrazone using hydrazine and then the hydrazone is converted into diazo under oxidation conditions, for example, using manganese dioxide ("MnO$_2$"). Carboxyl groups on the drug, such as those on insulin, react with the diazo groups to form the final photocleavable drug-polymer conjugate.

In this example (FIG. 4), a photocleavable group is attached to an insoluble polymer via an amide bond with an amino group on the polymer. The photocleavable group is modeled after dimethoxynitrophenylethyl ("DMNPE") group. This reaction is effected by a condensing agent, such as 1-ethyl-3-dimethylaminopropylcarbodiimide ("EDC"). The polymer can naturally have an amino group (for example in the case of chitosan), or can have an amino group grafted onto it (for example in the case of a poly-glutamic acid resin). Once the link has been made with the resin, the next step is to convert the ketone functionality into a hydrazone functionality. This can be effected with hydrazine and catalyzed with acid.

Alternatively, other hydrazides can be used, for example 2,4,6 -triisopropylbenzenesulphonohydrazide. The resulting hydrazone is converted to the diazo under oxidation conditions, for example by using triethylamine or potassium hydroxide in the case of the 2,4,6 -triisopropylbenzenesulphonohydrazide product. As another example, peroxy acetic acid, tetramethyl guanidine and iodine as generally described by Adamson et al., *Amino-acids and peptides. Part II. A new method for preparing diazodiphenylmethane* and related compounds, J. Chem. Soc, Perkin Trans 1 2030-2033 (1975) may be employed.

An exemplary reaction involves the conversion of 4,5-dimethoxy-2-nitroacetophenone hydrazone to 1-(4,5-Dimethoxy-2-nitrophenyl) diazoethane. More specifically, to 163 nmoles (1.95 μL of 83.60 mM stock in NMP) of 4,5 -dimethoxy-2-nitroacetophenone hydrazone, added 49 nmoles iodine (1.24 μL of 39.40 mM iodine stock in NMP), 8μmoles of 1,1,3,3 -tetramethylguanidine (1.02 μL) and 2.5μmoles of peracetic acid (0.86 μL of 39% peracetic acid solution) in the order indicated. The solution was shaken for 30 minutes and then dried.

The diazo group can then react with different functional groups on the drug. In the case of the drug insulin, a likely reactive group is one of the carboxyl groups on its surface. Carboxyl groups react readily with diazo groups to form the final ester linked conjugate. Upon photolysis, the bond between the carboxyl oxygen on the insulin and the polymer bound photocleavable group is broken, releasing active insulin.

For simplicity, a single drug molecule of insulin is shown being linked to the polymer via the photocleavable group. However, it will be appreciated that the reaction may occur along the polymer chain (either within the chain or at the terminal ends) such that the polymer chain is loaded with several drug molecules of insulin using the scheme.

It will be further appreciated to one skilled in the art that this synthesis scheme could be readily applied to any polymer chain having an amine functionality (or a functionality that could be converted through one or more steps) to an amine functionality. Likewise, this synthesis scheme could be readily applied to any drug molecule having a carboxyl functionality (or a functionality that could be converted through one or more steps) to a carboxyl functionality.

EXAMPLE 2

Linear, Sequential (A1)

Figure 5A:
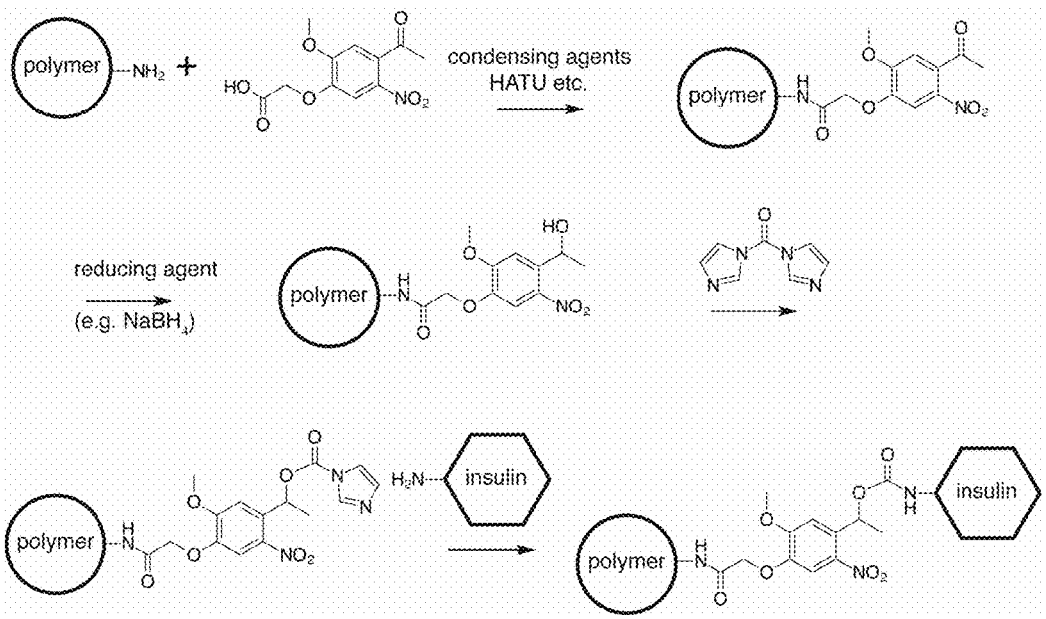
FIG. 5A shows an exemplary linear sequential synthesis approach for the preparation of an exemplary photocleavable drug-polymer conjugate. An insoluble polymer (shown as an enlarged circle) is linked to a photocleavable group using a condensation reaction. A ketone functionality on the photocleavable group is converted to an alcohol. After the reduction, carbonyldiimidazole is used to form a carbamate between the photocleavable group and the drug. That is, amino groups on the drug, such as those on insulin, react with the imidazole groups to form the final photocleavable drug-polymer conjugate.
Figure 5B:
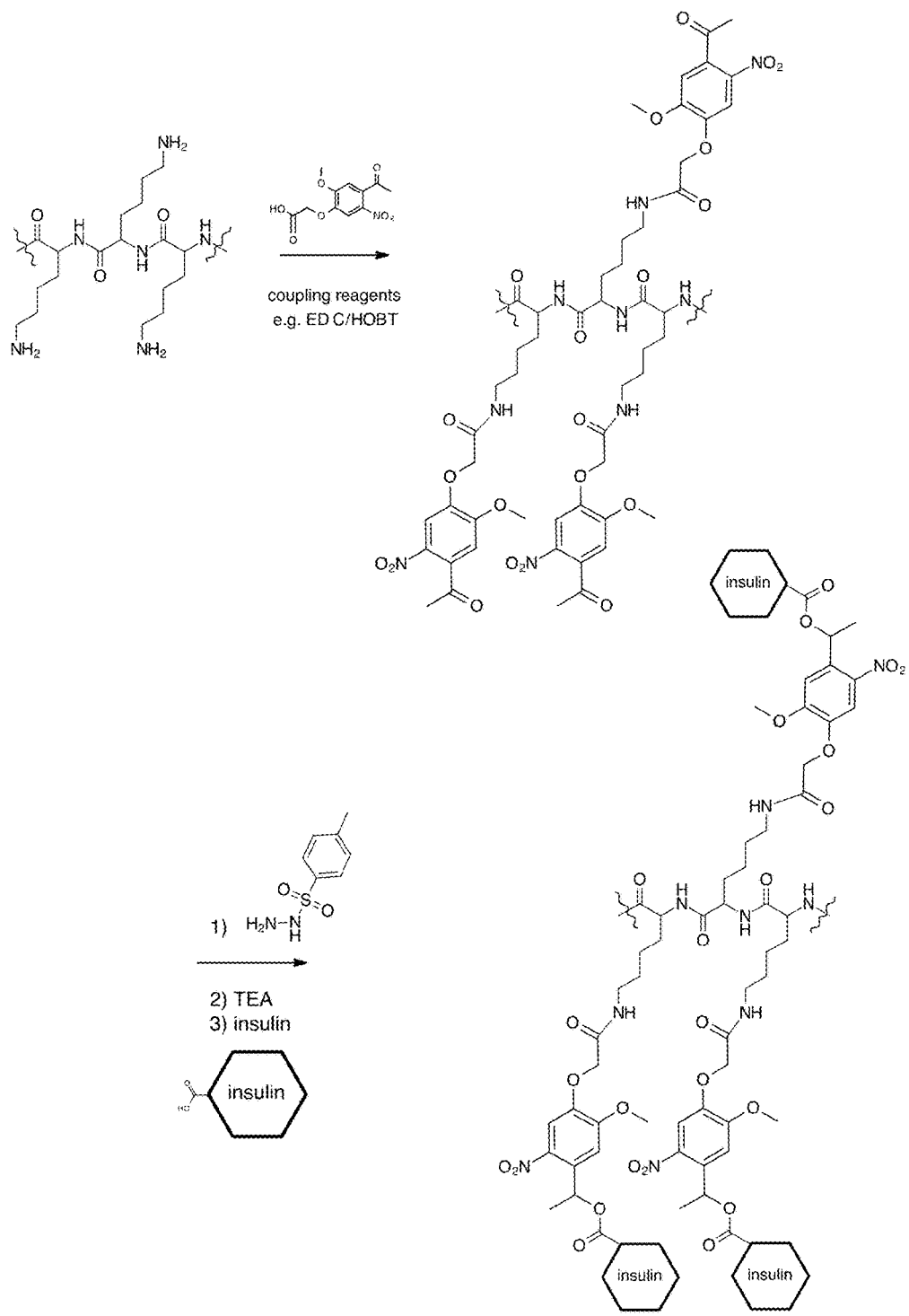
FIG. 5B provides another exemplary linear sequential synthesis approach.

In this example (FIG. 5), the polymer is (poly)lysine. Three consecutive lysine residues are illustrated. The photocleavable group is attached to the amine in the (poly)lysine via an amide bond. This reaction is effected by a coupling agent, such as EDC. The resultant ketone is converted to a hydrazone via the tosyl-hydrazide depicted. This hydrazone is converted to the diazo via treatment with triethyl amine ("TEA") or other base. The resin-bound diazo group can then react with functionalities on the insulin. In the example depicted, this functionality is a carboxyl group on an insulin. Upon photolysis of the final conjugate, the native insulin is released.

EXAMPLE 2A

Linear, Sequential (A1)

In this example (FIG. 5A), a photocleavable group is attached to an insoluble polymer via an amide bond with an amino group on the polymer. The photocleavable group is modeled after DMNPE. This reaction is effected by a condensing agent, such as EDC. The polymer can naturally have an amino group (for example in the case of chitosan), or can have an amino group grafted onto it (for example in the case of a poly-glutamic acid resin). Once the link has been made with the resin, the insulin is linked to the photocleavable resin by reaction of an amine on the insulin with a resin bound activated carbamate linkage. That is, a ketone functionality on the photocleavable group is converted to an alcohol. After the reduction, carbonyldiimidazole is used to form a carbamate between the photocleavable group and the drug. Amino groups on the drug, such as those on insulin, react with the imidazole groups to form the final photocleavable drug-polymer conjugate. In this case, the final material upon photolysis will also release native insulin.

EXAMPLE 3

Linear, Convergent (A2)

Figure 6A:
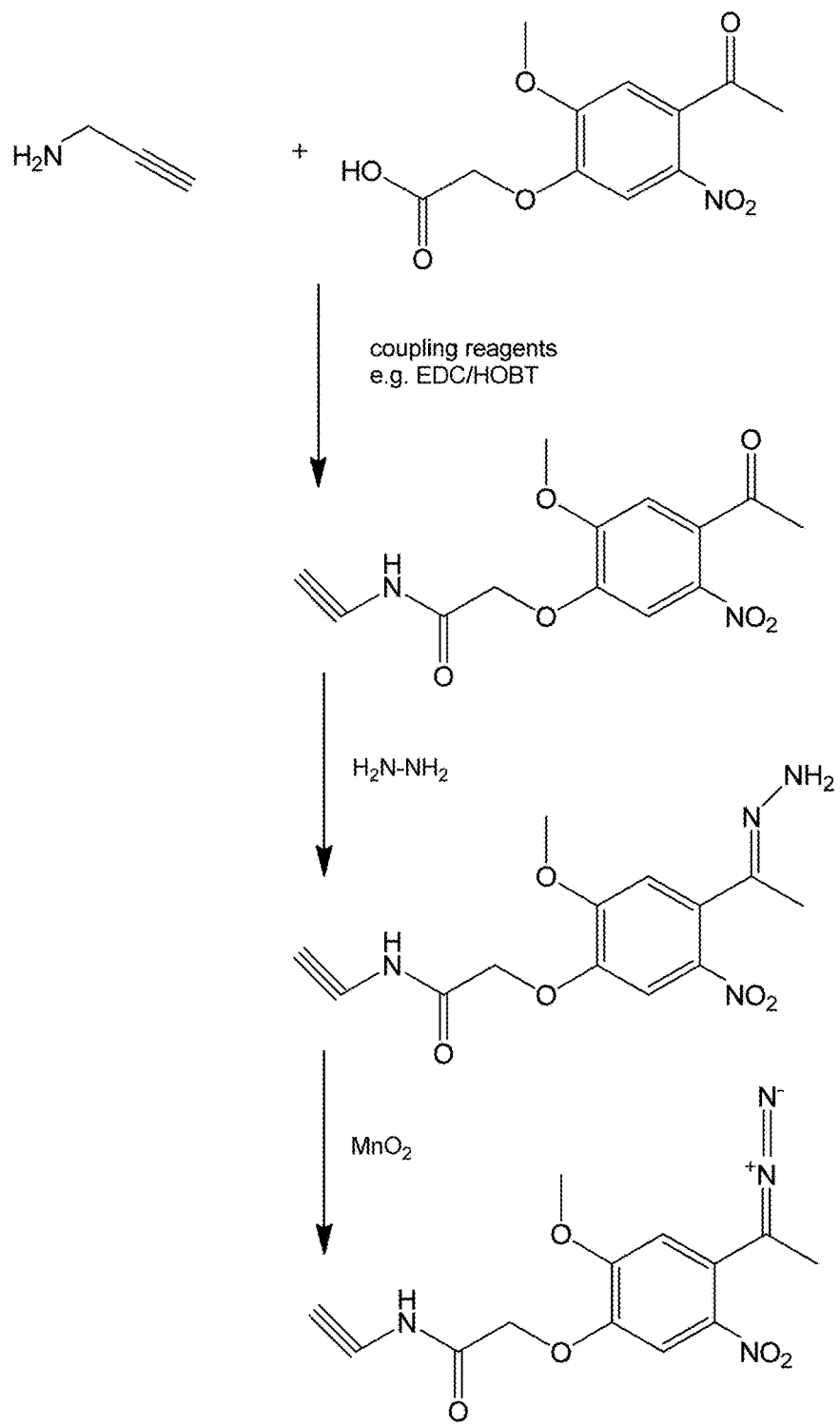
FIG. 6 illustrates an exemplary synthesis for preparation of another exemplary photocleavable drug-polymer conjugate using a linear convergent approach. In this example, the photocleavable group is a nitro aromatic containing both an alkyne and a diazo functionality, and is prepared according to the scheme shown in FIG. 6A. The diazo group reacts with the carboxy groups on the drug molecule (such as insulin), and the alkyne reacts with an azide on the polymer chain as shown in FIG. 6B.

In this, example, a linear convergent synthesis of a final conjugate is employed. As shown in FIG. 6A, DMNPE carboxylic acid is condensed with an alkyne, such as propargyl amine, using standard coupling reagents such as EDC/HOBT. The ketone group is then converted into the hydrazone using hydrazine. The hydrazone is then converted to the diazo through oxidation. The resultant diazo compound can then be reacted with functional groups on the insulin or other drug.

Figure 6B:
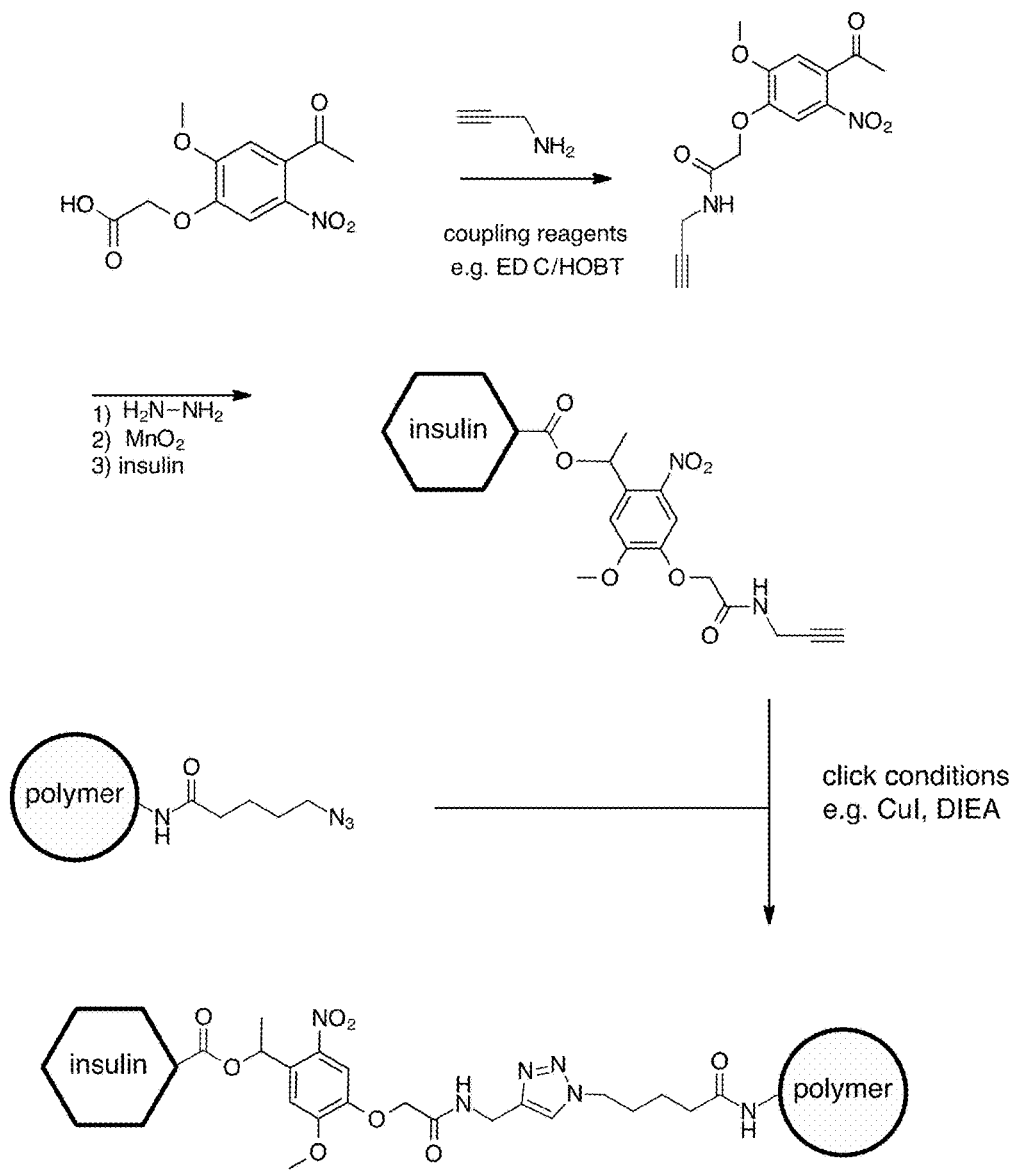

In parallel, as shown in FIG. 6B, an azide group is installed onto a polymer. This azide can then be reacted with the insulin-PC alkyne functionality, to make a triazole linkage. This is a so-called "click" reaction and can be effected with a variety of reagents including CuI and di-isopropyl ethylamine ("DIEA") or other combinations of reagents. The final conjugate upon photolysis will yield the active and native insulin molecule.

It will be appreciated that in this example, the photocleavable group comprises a diazo-alkyne. More broadly, the photocleavable group may be defined according to:

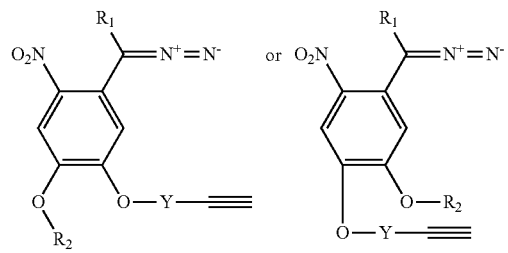

wherein $R_1$ is H or alkyl (preferably a $C_1$-$C_6$ alkyl); $R_2$ is H or alkyl (preferably a $C_1$-$C_6$ alkyl); Y is a linker chain (preferably a linker chain comprising about 1 to 100 atoms). The linker may comprise C, N, O, S, and/or P atoms, and may comprise 5, 10, 15, 20, 25, 30, 35, 40, 45, 50, 55, 60, 65, 70, 75, 80, 85, 90, 95, or 100 atoms. Exemplary linkers include alkyl or polyether groups.

EXAMPLE 4

Linear, Convergent (A2)

Figure 7:
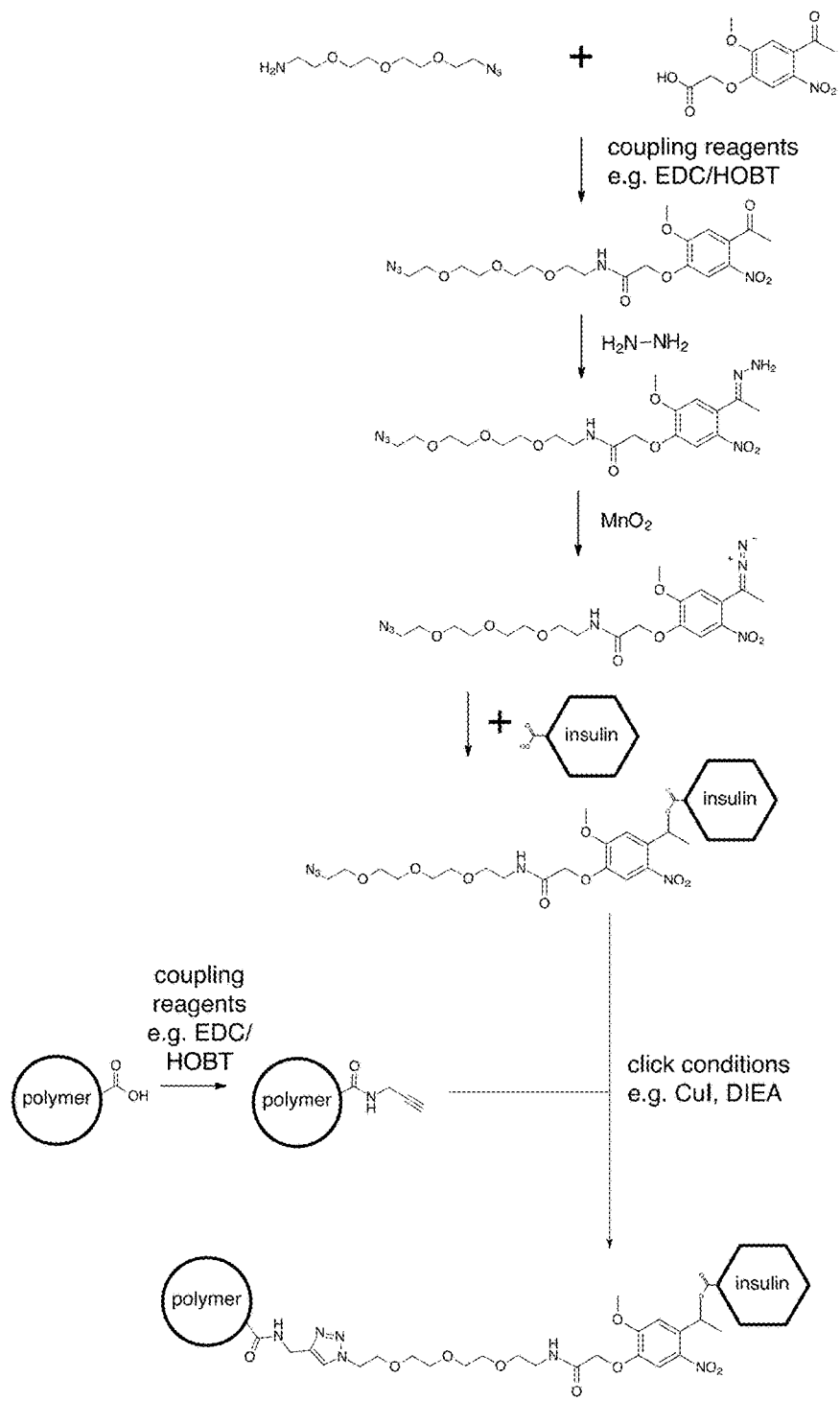
FIG. 7 illustrates an exemplary synthesis for preparation of another exemplary photocleavable drug-polymer conjugate using a linear convergent approach. In this example, the photocleavable group contains both an azide and a diazo functionality. The drug molecule (such as insulin) is linked to the photocleavable group via the diazo functionality and the carboxylic acid functional group on the drug molecule. That is, the drug molecule is linked to the photocleavable linker via an ester bond. The photocleavable group is linked via the azide to an alkyne on the polymer chain using triazole bridging.

In this example (FIG. 7), a convergent approach is again taken, using a triazole link, formed under "click" conditions to make the final link of drug with polymer. In this case, an azide is installed into the DMNPE like photocleavable group using standard coupling agents such as EDC. The ketone in the resultant molecule is converted to the hydrazone with hydrazine, which is then converted to the diazo under oxidation conditions. This diazo group then reacts with insulin to make the indicated conjugate ("insulin azide"). In parallel, a carboxyl group on the polymer is converted into an alkyne, by, for example, reacting with propargyl amine. The resultant modified polymer is then reacted with the insulin azide using the previously mentioned click conditions. The final conjugate, upon photolysis, will yield active insulin.

It will be appreciated that in this example, the photocleavable group comprises a diazo-azide. More broadly, the photocleavable group may be defined according to:

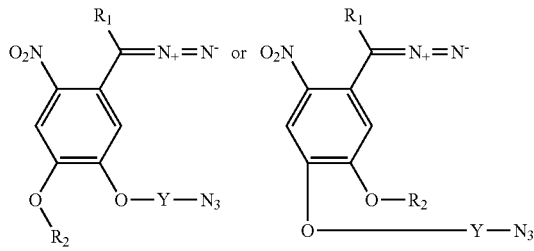

wherein $R_1$ is H or alkyl (preferably a $C_1$-$C_6$ alkyl); $R_2$ is H or alkyl (preferably a $C_1$-$C_6$ alkyl); Y is a linker chain (preferably a linker chain comprising about 1 to 100 atoms); and M is an integer (preferably 2, 3, 4, or 5). The linker may comprise C, N, O, S, and/or P atoms, and may comprise 5, 10, 15, 20, 25, 30, 35, 40, 45, 50, 55, 60, 65, 70, 75, 80, 85, 90, 95, or 100 atoms. Exemplary linkers include alkyl or polyether groups.

EXAMPLE 5

Linear, Convergent (A2)

Figure 8:
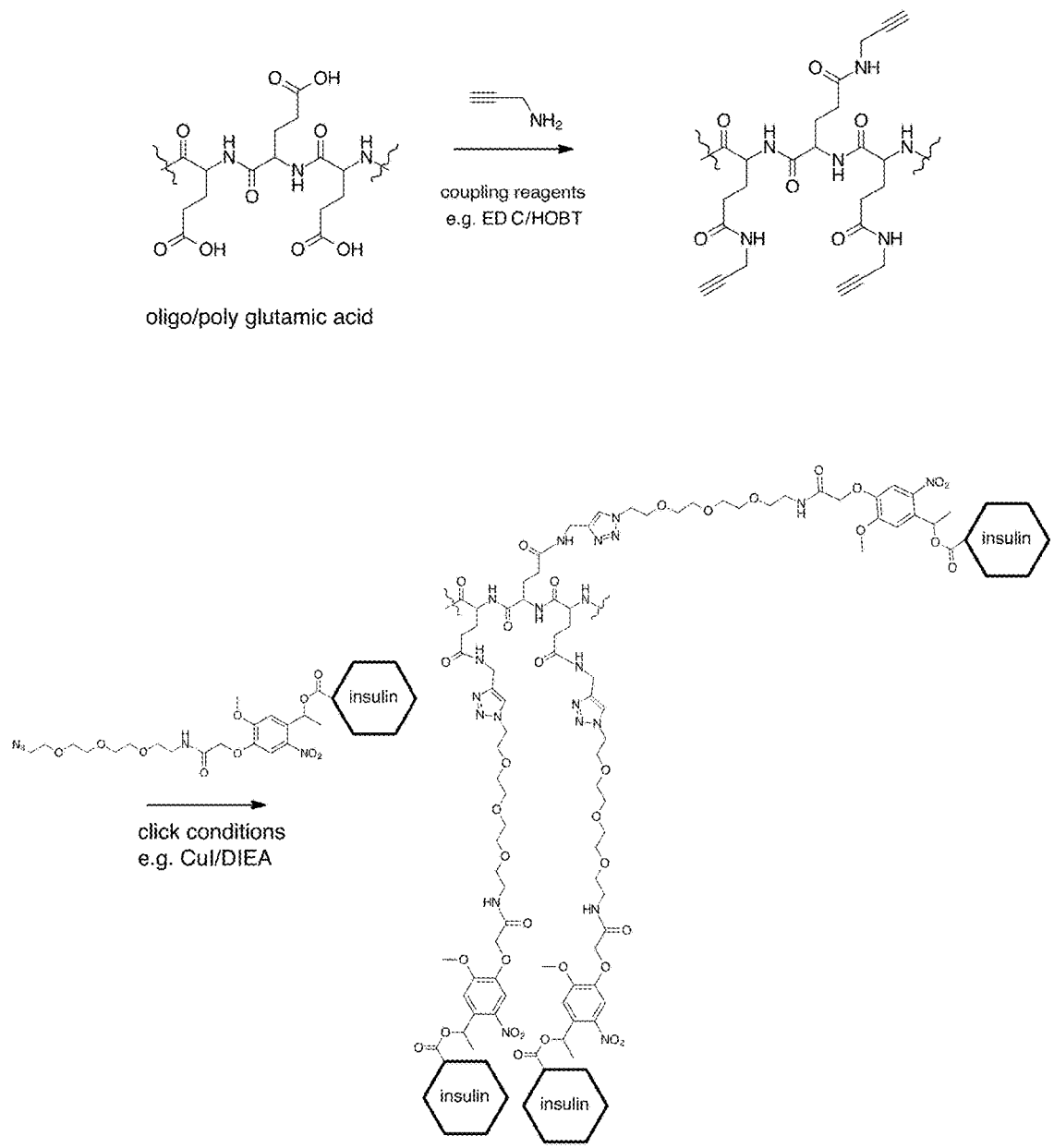
FIG. 8 provides an exemplary synthesis for linking a drug molecule, such as insulin, to a polymer chain which is a polypeptide or protein having acidic residues via a photocleavable group. In this exemplary synthesis, the photocleavable group has an azide and is reacted with an alkyne derived from an acidic residue on the polypeptide or protein to form a triazole bridge. Linkage to glutamic acid residues are illustrated.

In this example (FIG. 8), an oligo or poly glutamic acid species is coupled to propargyl amine, using standard coupling agents such as EDC and N-hydroxybenzotriazole ("HOBT"). The resultant polymer, which should have low aqueous solubility, will be coupled to "insulin azide" (e.g., described and depicted in Example 4). This will be accomplished using "click" conditions, for example CuI and DIEA.

EXAMPLE 6

Meshwork (B)

Figure 9A:
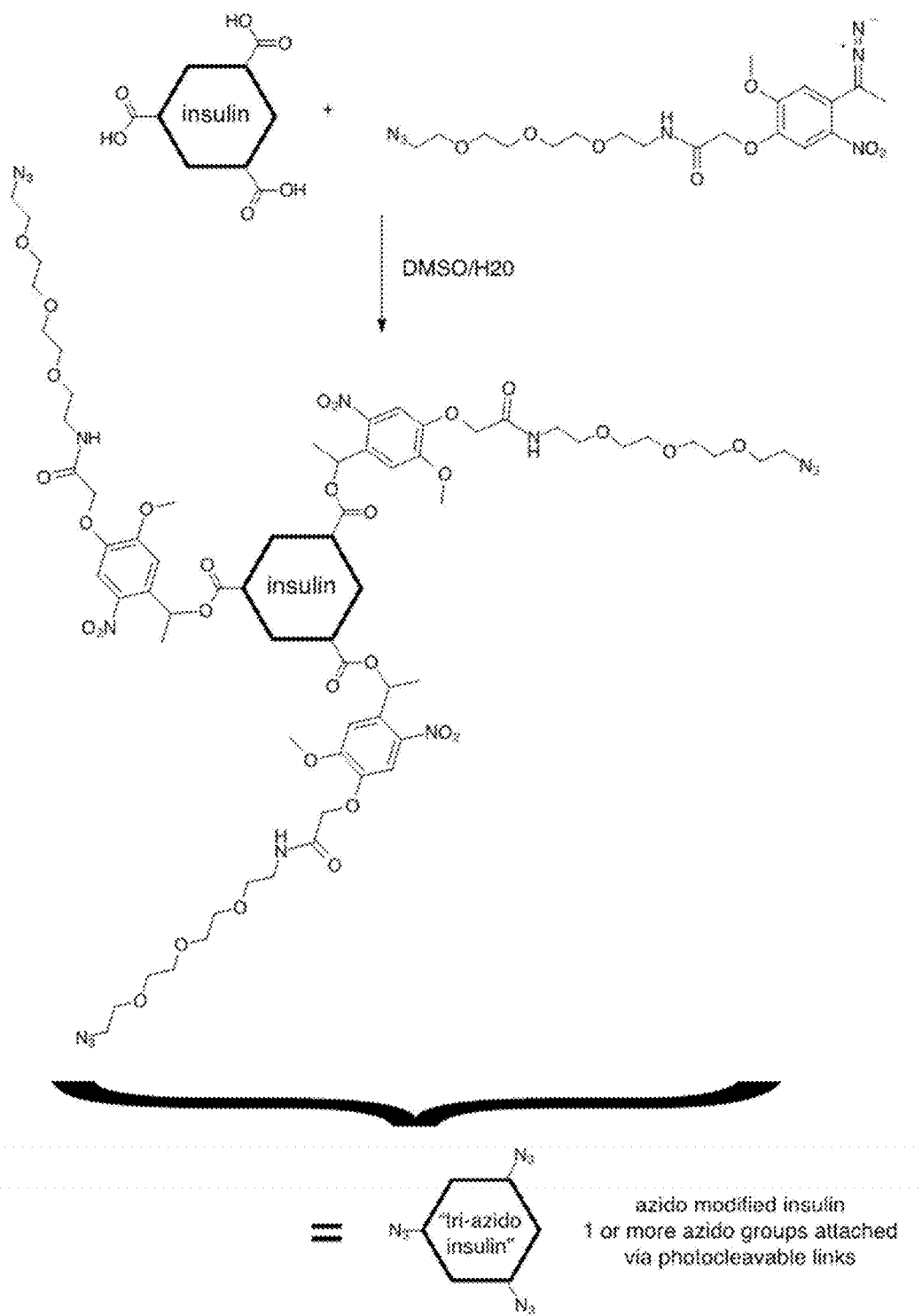
FIG. 9A and FIG. 9B illustrate an exemplary synthesis scheme for forming a photocleavable drug conjugate for forming the meshwork-type of depot. Insulin is modified with one or more azido groups attached via photocleavable groups. An alkyne platform is used to crosslink the insulin molecules together.

Synthesis of the photocleavable drug conjugate in this example occurs in two phases. In the first phase (FIG. 9A), multiple carboxyl groups on insulin are modified with a DMNPE-like photocleavable group that is terminated in an azide (the ultimate partner in performing the final coupling). While FIG. 9A shows three carboxyl groups reacting, there can be anywhere from 1 to 4 or more depending on reaction conditions. Having three or more will allow for more efficient creation of the meshwork. Upon reaction of the diazo functionality on the DMNPE-like molecule, "tri-azido insulin" as depicted will be formed and isolated.

Figure 9B:
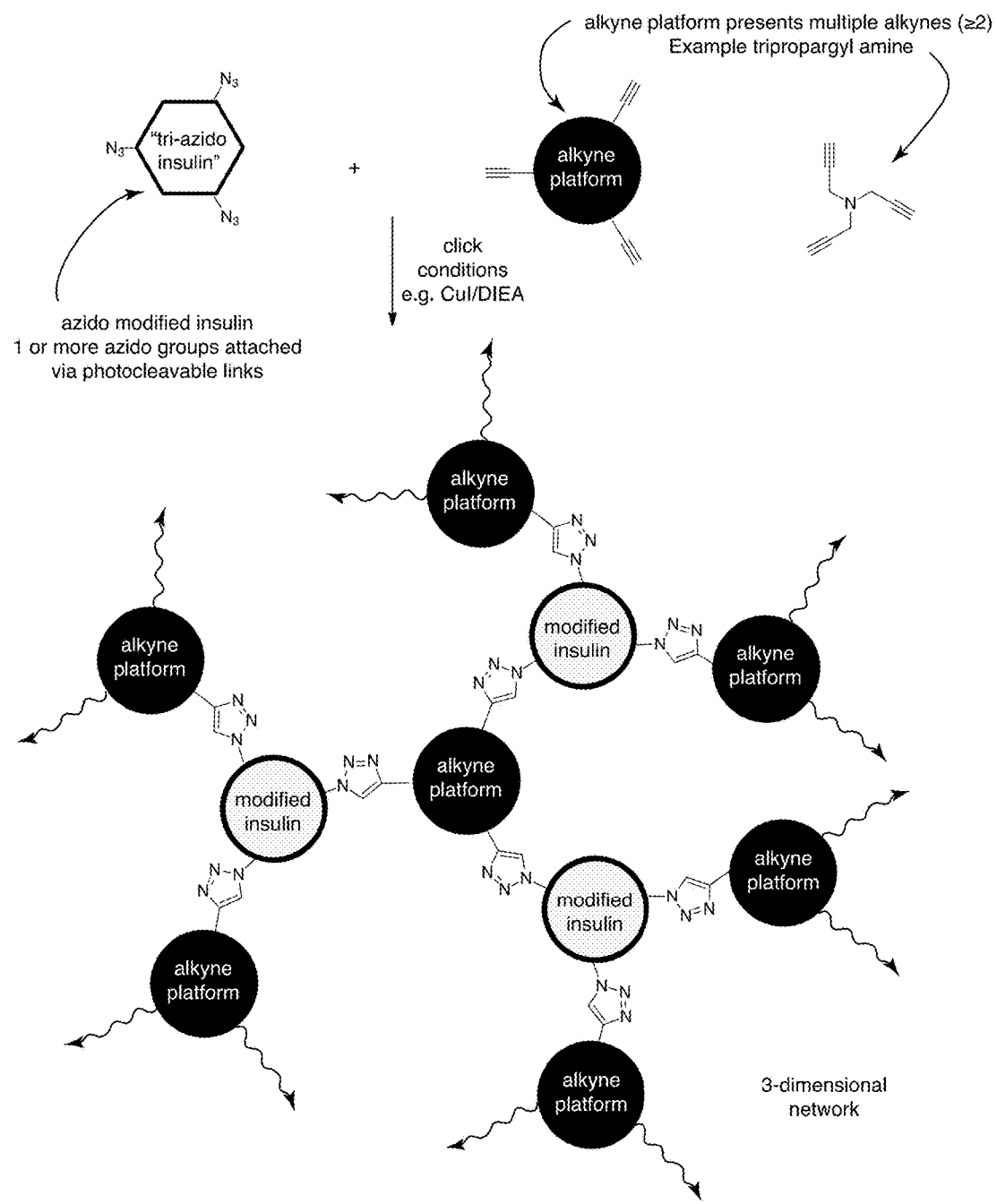

In phase two of the meshwork synthesis (FIG. 9B), the tri-azido insulin is reacted under click conditions with an alkyne presenting platform. This can present two or more alkynes (e.g., 2, 3, 4, 5, 6, 7, etc) to allow crosslinking to take place. An exemplary alkyne platform is shown, namely, the commercially available tripropargyl amine.

At the end of the reaction, a large meshwork of insulin will be formed, with minimal material except for insulin present. This will make this material particularly efficient with potentially 90% or more of the material being insulin. The overall molecular weight of the resultant material should be tunable depending on the relative amounts of insulin with differing numbers of azide groups attached. For example, the presence of an amount of insulin with a single azide group will tend to "cap" the growing polymer, as once it reacts with an alkyne, it can no longer further branch.

EXAMPLE 7

Meshwork (B)

Figure 10A:
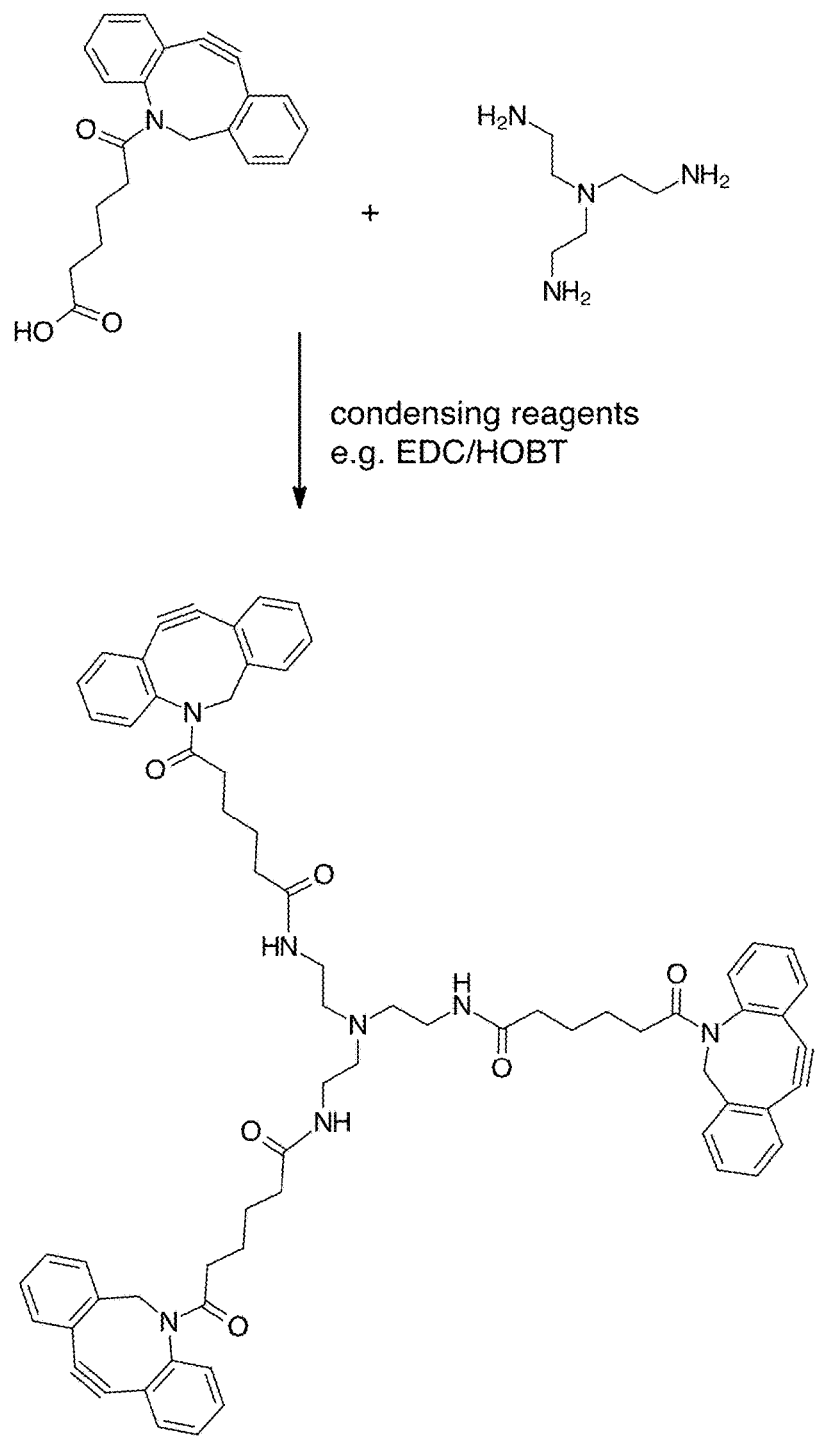
FIG. 10A and FIG. 10B illustrate another exemplary synthesis scheme for forming a photocleavable drug conjugate for forming the meshwork-type of depot. Insulin is modified with one or more azido groups (in this case a tri-azido insulin is shown) attached via photocleavable groups. A strained alkyne platform (e.g., a molecule containing two or more dibenzylcyclooctyne groups) is used to crosslink the insulin molecules together.
Figure 10B:
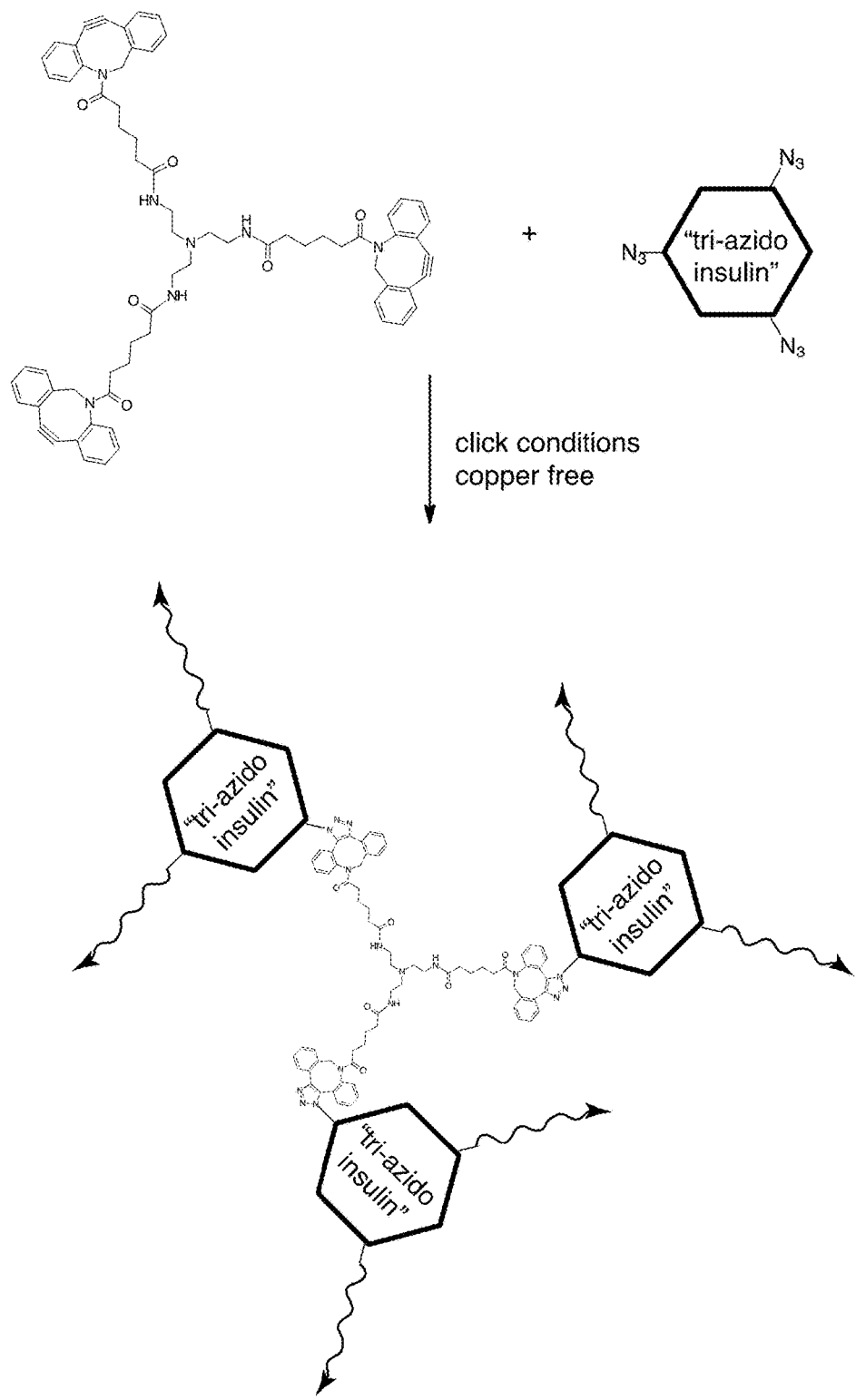

In this example, as shown in FIGS. 10A and 10B, the strained alkyne monomer dibenzylcyclooctynes ("DBCO") is condensed with the triamine tren, using standard condensing agents such as EDC/HOBT. The resulting molecule then presents three strained alkynes as the alkyne platform. These can then be reacted in a click fashion using the "tri-azido insulin" (i.e. insulin with photocleavable azides attached, synthesis previously depicted and described). Because both the insulin and the crosslinker have multiple sites of reactivity, a meshwork is the result. While "tri-azido insulin" has been shown, similarly insulin with only two azides will work. In order for a meshwork to be formed, as opposed to a linear polymer, one or both of the alkyne and azide presenting groups have to have at least three functional groups presented.

EXAMPLE 8

Meshwork (B)

In this example (FIG. 11B), the ultimate linkage that forms the meshwork involves a carbamate linkage. The carbamate is formed from amino groups donated by the insulin (e.g., the lysine side chain, and the N terminus on both insulin chains), and a photocleavable group having a carbonate ester. This ester can be formed from a DMNPE-like precursor and is at a minimum bifunctional (i.e., has at least two groups ready to react with insulin amines) although it can have more reactive sites. As depicted, the carbonate ester group is activated as the N-hydroxy succinimide (NHS) ester, which will readily react with the insulin amines. Once the crosslinks have formed a large meshwork will result. Photolysis will bring about the release of the native amino group of the insulin.

This linkage has a particular advantage potentially in that if a aggregate of the final material is released into the system via photolysis (i.e., containing more than one insulin molecule), the individual insulin molecules can still be liberated, through natural biochemical and chemical processes that cleave this carbamate bond to the resultant amine.

Figure 11A:
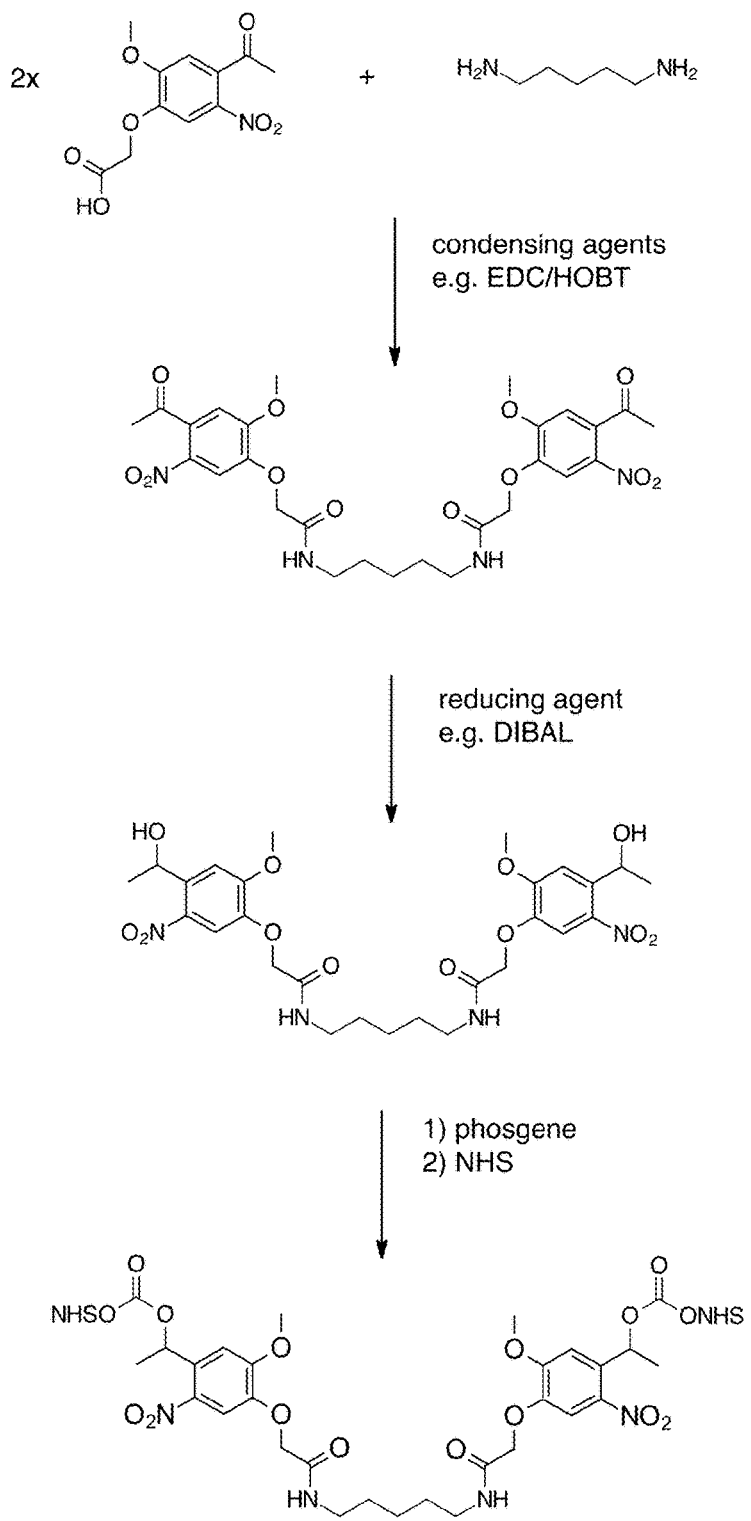
FIG. 11A and FIG. 11B provides an exemplary synthesis scheme for forming a photocleavable drug conjugate in which the drug (such as in insulin) and the photocleavable group is a crosslinker having two reactive groups. The bifunctional crosslinker forms a carbamate linkage with insulin. Release of the drug may occur using both photolysis or esterases. Synthesis of the crosslinker group is illustrated in FIG. 11A.
Figure 11B:
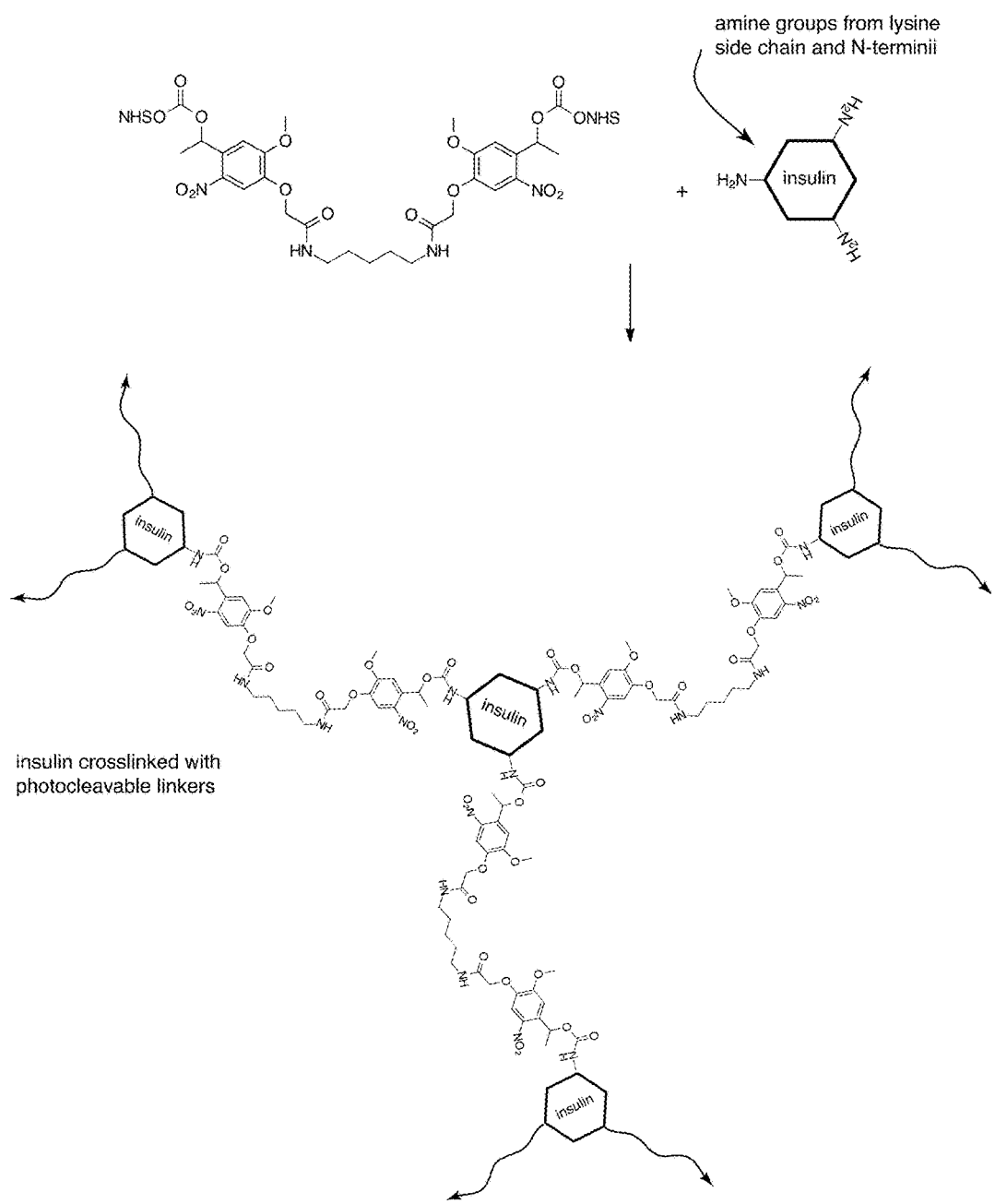

Synthesis of the linker is illustrated in FIG. 11A. In general, the precursor DMNPE "keto-acid" is condensed with a diamine, such as the di-amino pentane depicted. This is effected with condensing agents, such as EDC/HOBT. The resultant dimer is then reduced using a mild and selective reducing agent, such as DIBAL or sodium cyano borohydride. The resultant di-alcohol is then condensed with phosgene or a functional equivalent to make a chloroformate or related reactive intermediate. This is then reacted with N-hydroxy succinimide to make the final activated cross linker.

It will be appreciated that polyamines can yield corresponding multifunctional photocleavable linkers. Thus, in another aspect, the photocleavable group may be a carbonate-multimer. For example, the photocleavable functional group may be defined according to:

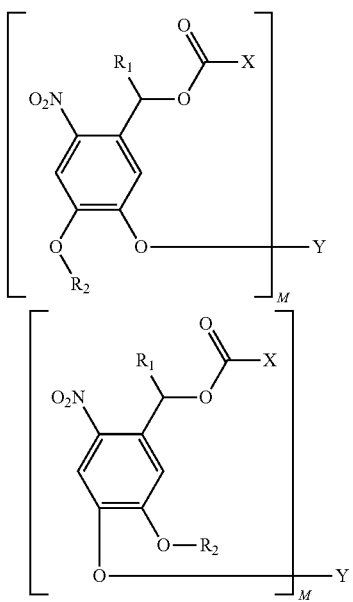

wherein $R_1$ is H or alkyl (preferably a $C_1$-$C_6$ alkyl); $R_2$ is H or alkyl (preferably a $C_1$-$C_6$ alkyl); X is a leaving group (such as N-hydroxyl succinimide); Y is a linker chain (preferably a linker chain comprising about 1 to 100 atoms); and M is an integer (preferably 2, 3, 4, or 5). The linker may comprise C, N, O, S, and/or P atoms, and may comprise 5, 10, 15, 20, 25, 30, 35, 40, 45, 50, 55, 60, 65, 70, 75, 80, 85, 90, 95, or 100 atoms. Exemplary linkers include alkyl or polyether groups.

EXAMPLE 9

Meshwork (B)

The meshwork (also referred to as a macropolymer) examples schematically shown in FIG. 1, 9A, 9B, 10B, 11B with insulin (or "drug") are shown with three points of connection radiating from the drug/insulin. It will be appreciated to those skilled in the art that meshwork approach will also work with other numbers of connections radiating from the drug/insulin (for example 1, 2, 4 etc.). In this example, a "meshwork" approach in which insulin having two and one points of attachment is shown.

Figure 12A:
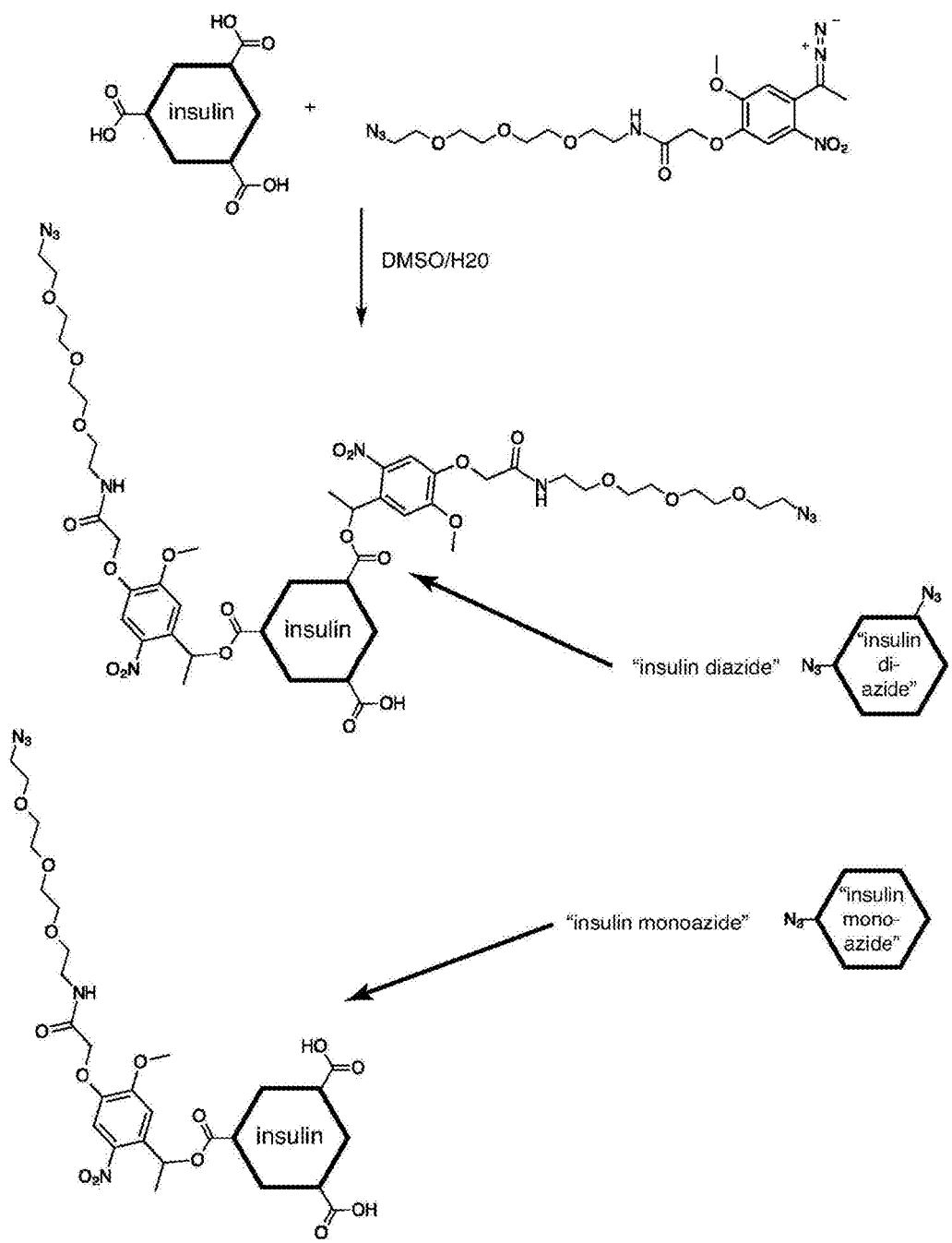
In FIG. 12A, insulin is modified with one or more azido groups (in this case a mono-azido insulin and di-azido insulin is shown) attached via photocleavable groups.
Figure 12B:
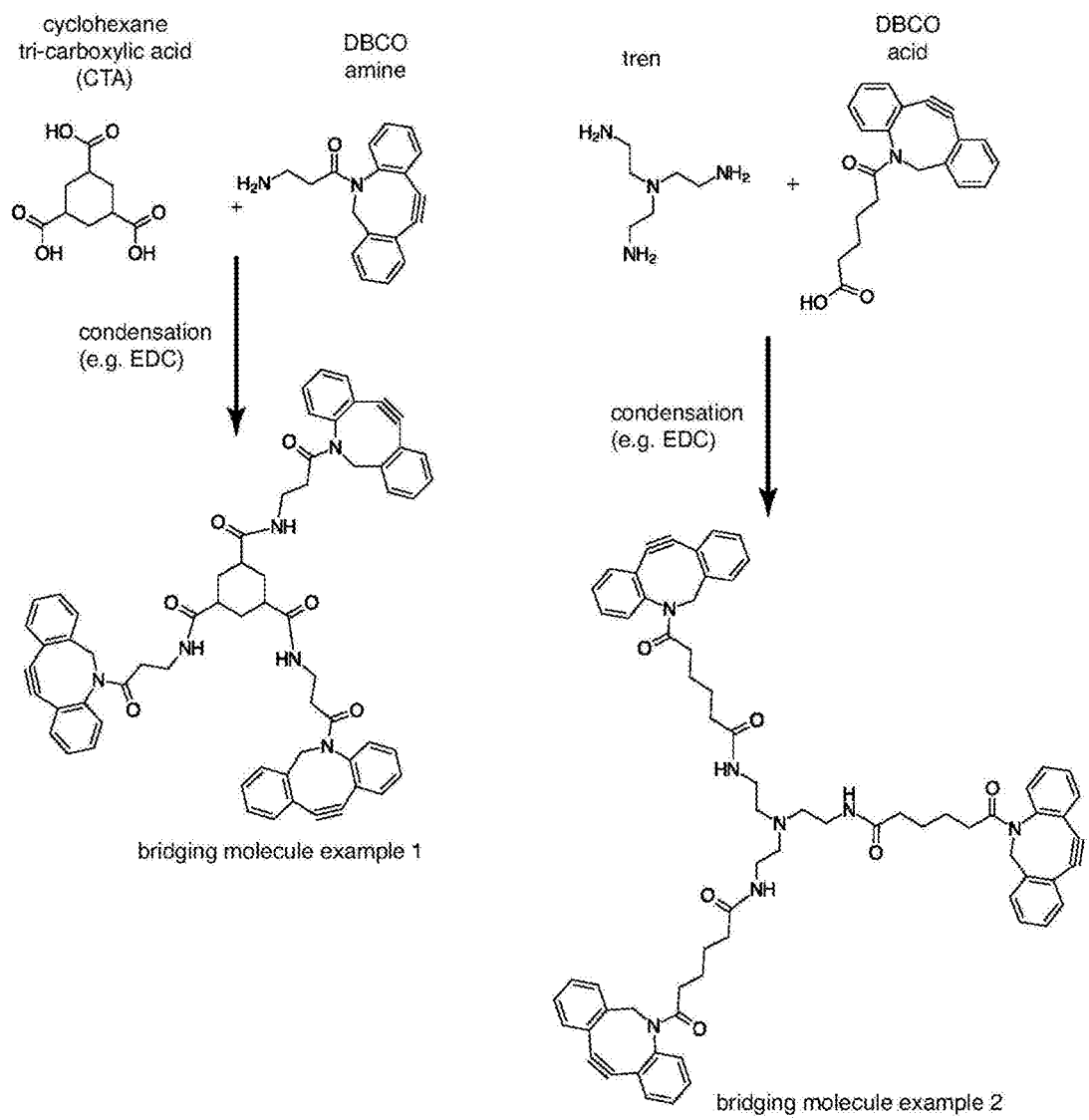
FIG. 12B shows the synthesis of an exemplary alkyne platform (the bridging molecule examples 1 and 2) which is used to crosslink the insulin molecules together, as illustrated in FIG. 12C.
Figure 12C:
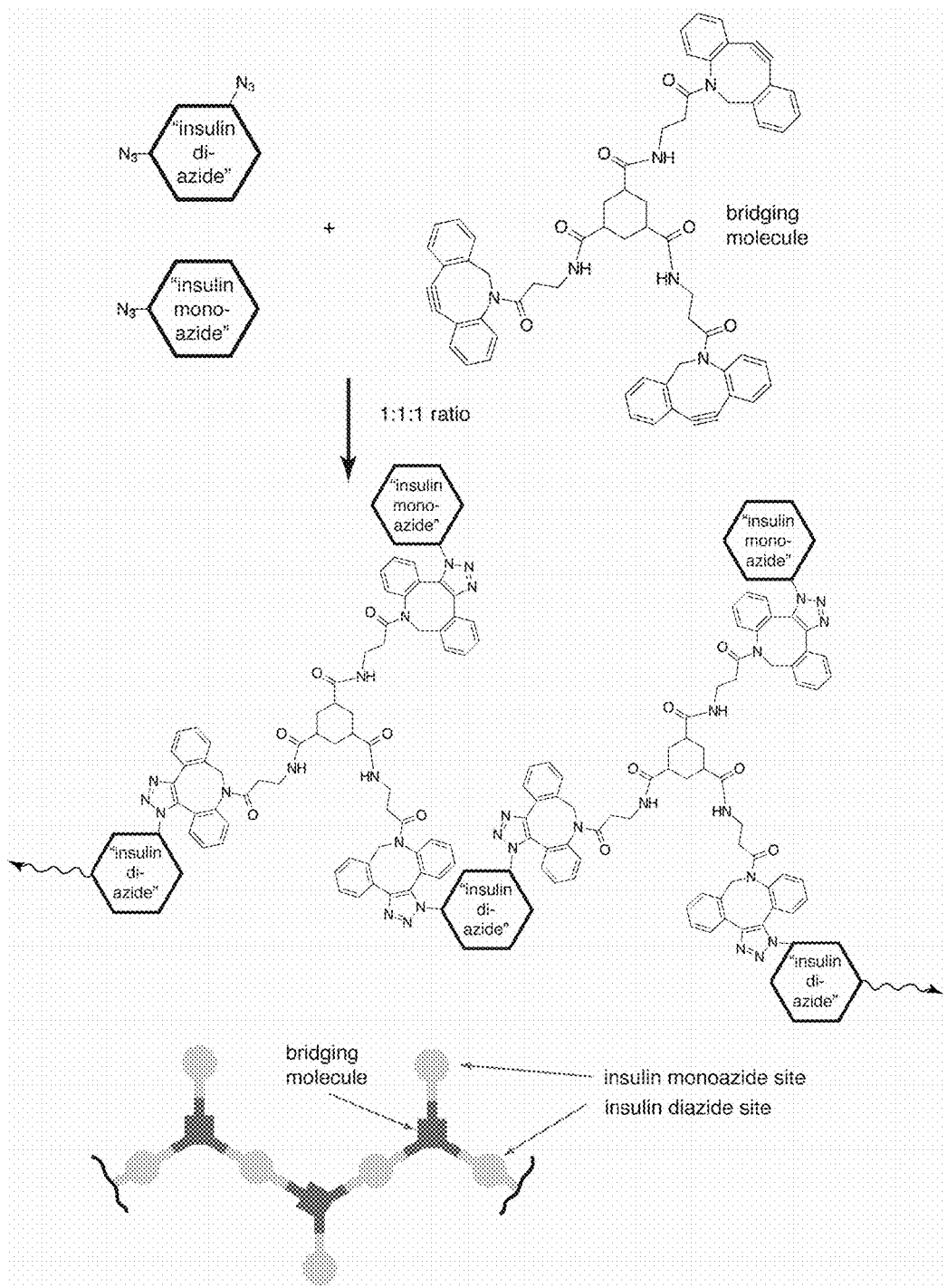
FIG. 12 illustrates another exemplary synthesis scheme for forming a photocleavable drug conjugate for forming the meshwork-type of depot.
FIG. 12D(a), FIG. 12D(b), FIG. 12E(a) and FIG. 12E(b) illustrate the HPLC and MS data for the first bridging molecule and second bridging molecules, respectively.
FIG. 12F shows the insulin polymerization products of the meshwork-type depot formed using bridging molecule example 1.

More specifically, in this example, insulin mono-azide and insulin di-azide were isolated after reaction of the appropriate diazo precursor with insulin (FIG. 12A). In parallel, a bridging molecule was synthesized. Each of the exemplary bridging molecules is has two or more (in this case three) alkyne groups. Two examples of a bridging molecule synthesis are shown in FIG. 12B. In the first example, cyclohexane carboxylic acid was reacted with a strained cyclo-octyne amine (DBCO amine) to form a three-armed bridging molecule. In the second example of bridging molecule synthesis, the amine tren was reacted with DBCO acid to make a similar three-armed bridging molecule. Either of these bridging molecules can then be reacted with equimolar amounts of the insulin mono-azide and di-azide, to make a polymer (FIG. 12C), which will yield insulin upon photolysis, and a small amount of bridging molecule. Of course, while this example uses a bridging molecule with three arms, it could have four or more arms. There are many possible variations on this bridging molecule, with arms of different lengths and different chemical constituents.

Materials

N,N-dimethylformamide, dimethyl sulfoxide, acetonitrile, methanol, trifluoroacetic acid, 1 N HCl, 1 N acetic acid were purchased from Fischer Scientific. Tris[2-(dimethylamino)ethyl]amine), 1,3,5 -cyclohexanetricarboxylic acid were purchased from Sigma Aldrich. DBCO acid and DBCO amine were purchased from Click Chemistry Tools. Hydroxybenzotriazole hydrate (Peptides International), 1-ethyl-3-(3'-dimethylaminopropyl)carbodiimide hydrochloride (Calbiochem)

Methods

Figure 12D:
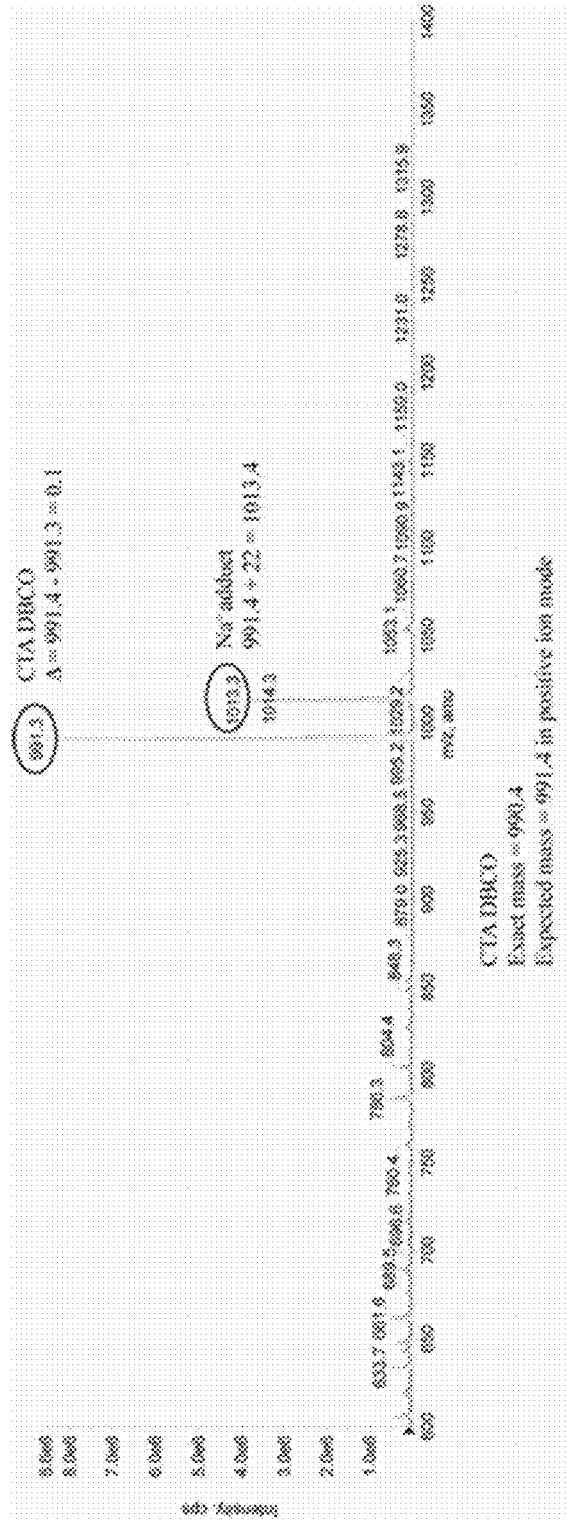
Figure 12D:
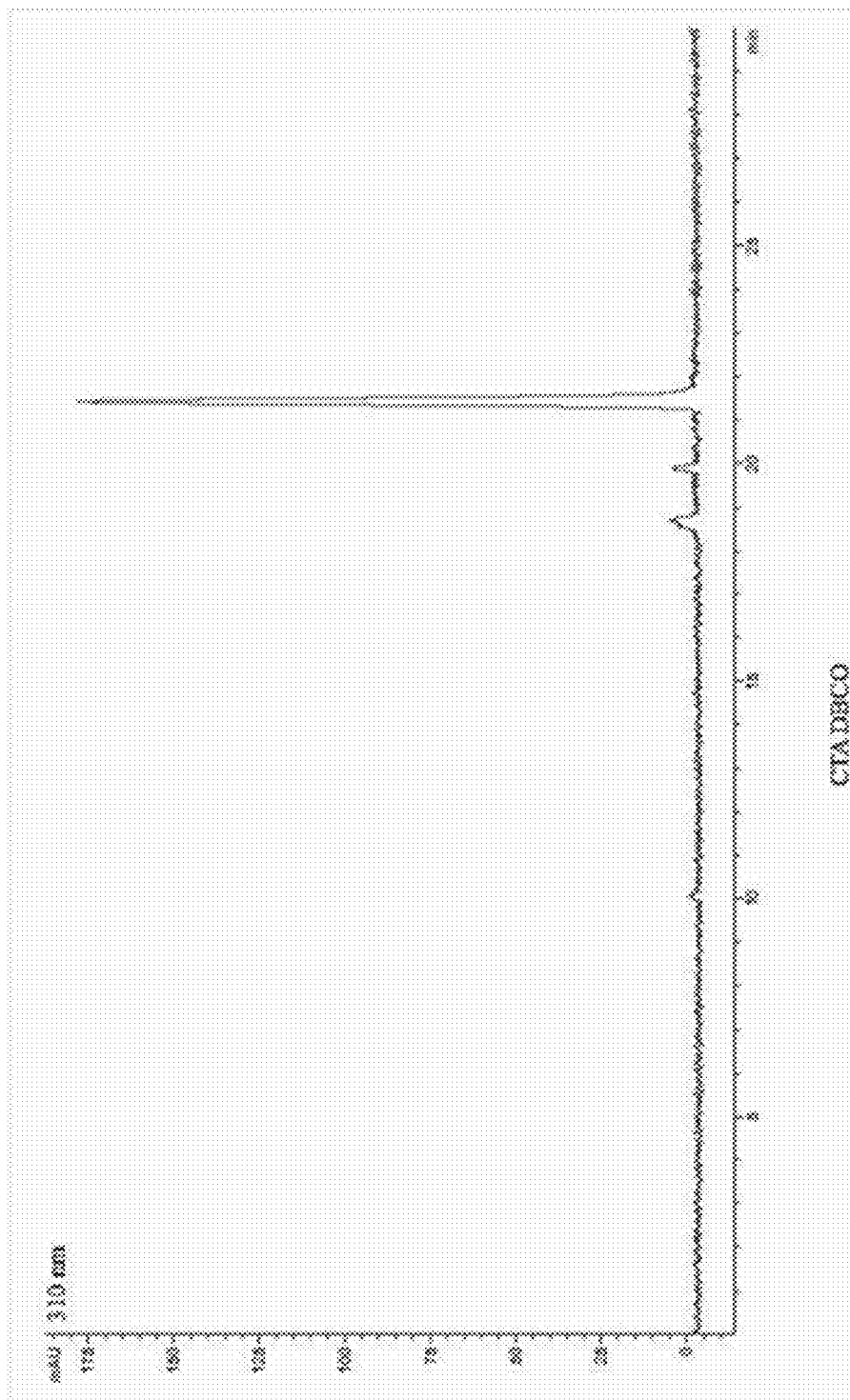

Compound 1: CTA DBCO Bridging molecule 1,3,5-Cyclohexanetricarboxylic acid (3.47 mg, 16.08 μmoles), 1-ethyl-3-(3'-dimethylaminopropyl)carbodiimide hydrochloride (14.1 mg, 73.55 μmoles) and hydroxybenzotriazole hydrate (11 mg, 71.89 μmoles) were added to a 140 μL solution of N,N-dimethylformamide (DMF). It was shaken until everything was dissolved. To this added DBCO amine (20.2 mg, 73.1 μ moles) and shaken for 24 hours. The desired product was purified by reversed phase HPLC (flow rate 2 mL/min, runtime 40 minutes), solvent A (0.1% trifluoroacetic acid (TFA) in water), solvent B (0.1% TFA in acetonitrile (ACN)), gradient 0% B to 100% B over 30 minutes, isocratic 100% B for next 10 minutes, C18 column with TMS endcapping (5 μm, 250×10 mm, Phenomenex): the crude reaction mixture was run multiple times and the fractions(or peak) at 34-35 minutes were collected, combined, dried and analyzed using HPLC and mass spectrometry. Yield 7.6 mg (48.1% yield), Purity (95%, HPLC). TLC (EtOAc/MeOH, 50:50 v/v): Rf=0.82; UV/vis (methanol) λmax (ελ): 310 nm (36000 M−1 cm−1), reversed phase HPLC (flow rate 1 mL/min, runtime 30 minutes), solvent A (0.1% TFA in water), solvent B (0.1% TFA in ACN), gradient 0% B to 100% B over 25 minutes, isocratic 100% B for 5 minutes, C18 with Hypersil column (5 μm, 250×4.6 mm, Agilent Microsorb): retention time (min) 21.41, ESI-MS (m/z): [MH]+ calculated for [$C_{63}H_{54}N_6O_6$], 991.4; found, 991.3. See FIGS. 12D(a) and 12D(b) for HPLC and MS.

Compound 2: Tren DBCO Bridging molecule

Figure 12E:
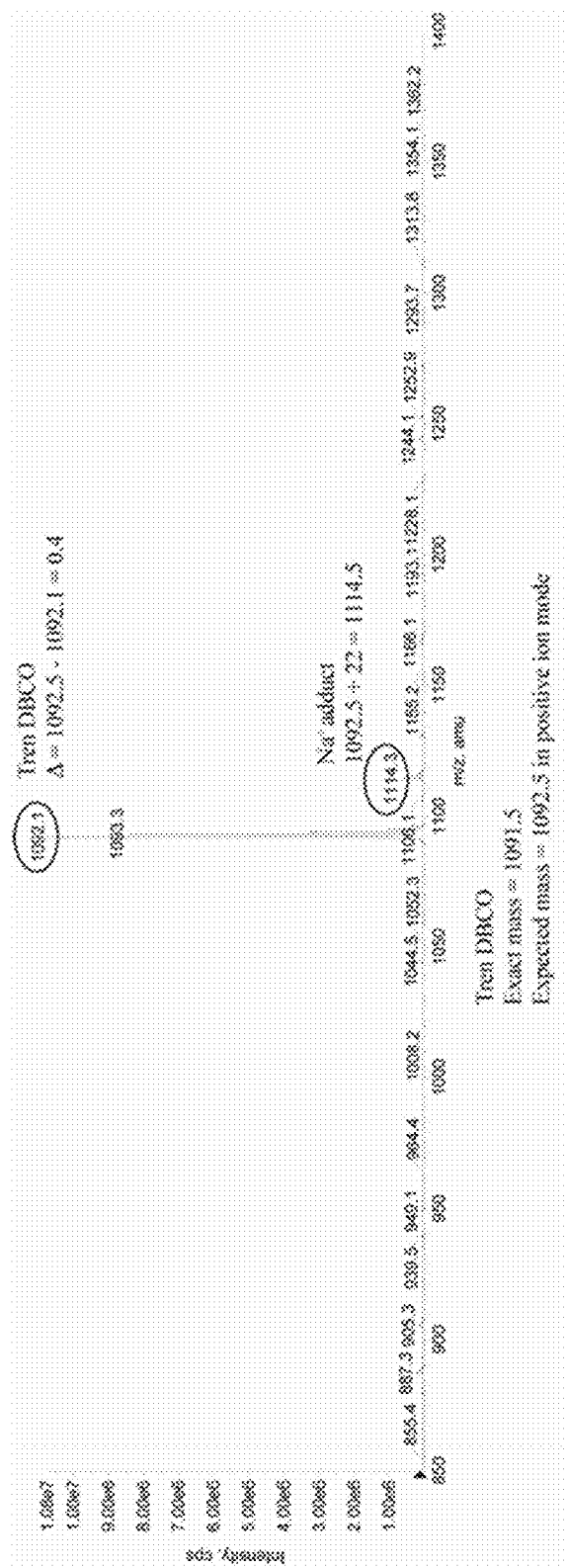
Figure 12E:
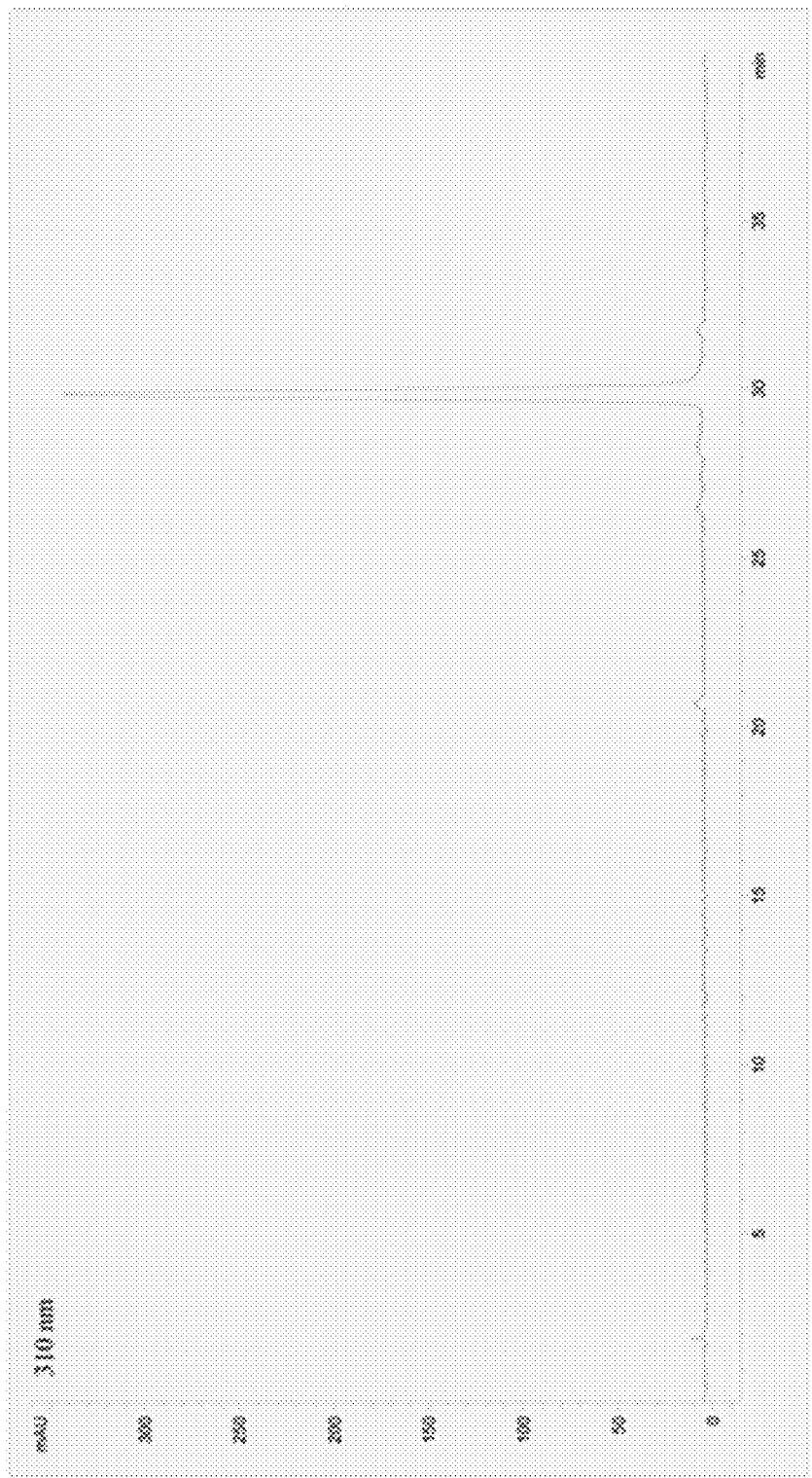

1-Ethyl-3-(3'-dimethylaminopropyl)carbodiimide hydrochloride (12.1 mg, 63.1 μmoles), hydroxybenzotriazole hydrate (9.5 mg, 62 μmoles) and DBCO acid (20.2 mg, 60.6 μmoles) were added to a 160 μL solution of DMF. The solution was shaken until it became clear. To this solution tris[2-(dimethylamino)ethyl]amine) (2 mg, 13.68 μmoles) was added and shaken for 24 hours. The product was purified by reversed phase HPLC (flow rate 2 mL/min, runtime 40 minutes), solvent A (0.1% TFA in water), solvent B (0.1% TFA in ACN), gradient 0% B to 100% B over 30 minutes, isocratic 100% B for next 10 minutes, C18 column with TMS endcapping (5 μm, 250×10 mm, Phenomenex): the crude reaction mixture was run multiple times and the fractions(or peak) at 30 minutes time were collected, combined, dried and analyzed using HPLC and mass spectrometry. Purity (99%, HPLC), TLC (EtOAc/MeOH, 50:50 v/v): Rf=0.61; UV/vis (methanol) λmax (ελ): 310 nm (36000 M−1 cm−1), reversed phase HPLC (flow rate 2 mL/min, runtime 40 minutes), solvent A (0.1% TFA in water), solvent B (0.1% TFA in ACN), gradient 0% B to 100% B over 25 minutes, isocratic 100% B for 5 minutes, C18 with TMS endcapping (5 µm, 250×10 mm, Phenomenex): retention time (min) 29.83: ESI-MS (m/z): [MH]+ calculated for [$C_{69}H_{69}N_7O_6$], 1092.5; found, 1092.1. See FIGS. 12E(a) and 12E(b) for HPLC and MS.

Compound 3: Insulin Polymers

Three stock solutions were prepared, compound 1 (5 mM) in DMSO, insulin monoazide (2 mM) and insulin diazide (2 mM) in 0.01 N HCl. Reaction 1 was initiated by adding insulin monoazide (1.5 µL, 3 nmoles) and insulin diazide (1.5 µL, 3 nmoles) to 65.4 µL 0.01 N HCl and subjected to sonication for 20 minutes, then to it added compound 1 (0.6 µL, 3 nmoles) and the reaction was allowed to go for 24 hours under sonication in 37° C. water bath in the dark. Reaction 2 was initiated by adding insulin monoazide (3 µL, 6 nmoles) and insulin diazide (3 µL, 6 nmoles) to 65.4 µL 0.01 N HCl, vortexed gently and then to it added compound 1 (1.2 µL, 6 nmoles). Reaction 3 was initiated by mixing insulin monoazide (1.5 µL, 3 nmoles) and insulin diazide (1.5 µL, 3 nmoles), vortexed gently and then to it added compound 1 (0.6 µL, 3 nmoles). The following stock solutions were used for further reactions, compound 1 (5 mM) in DMSO, insulin monoazide (2 mM) and insulin diazide (2 mM) in 20% acetic acid. Reaction 4 was initiated by adding insulin monoazide (1.5 µL, 3 nmoles) and insulin diazide (1.5 µL, 3 nmoles) to 65.4 µL 20% acetic acid, vortexed gently and then to it added compound 1 (0.6 µL, 3 nmoles). Reaction 5 was initiated by mixing insulin monoazide (1.5 µl, 3 nmoles) and insulin diazide (1.5 µL, 3 nmoles) gently and then to it added compound 1 (0.6 µL, 3 nmoles). All the reactions were carried out at 37° C. for 24 hours. After 24 hours, all the reaction mixtures were dried and reconstituted in 20 µL SDS loading solution (10 µL DMSO+10 µL SDS PAGE loading buffer), except reaction 2 which was reconstituted in 40 µL of the same solution.

For photolysis study, 25 µL from reaction 2 was taken in a microcentrifuge tube and irradiated for 10 minutes using a Blak-Ray lamp (Model XX-15 L, 30 W) placing the lamp 10 cm above the tube.

Figure 12F:
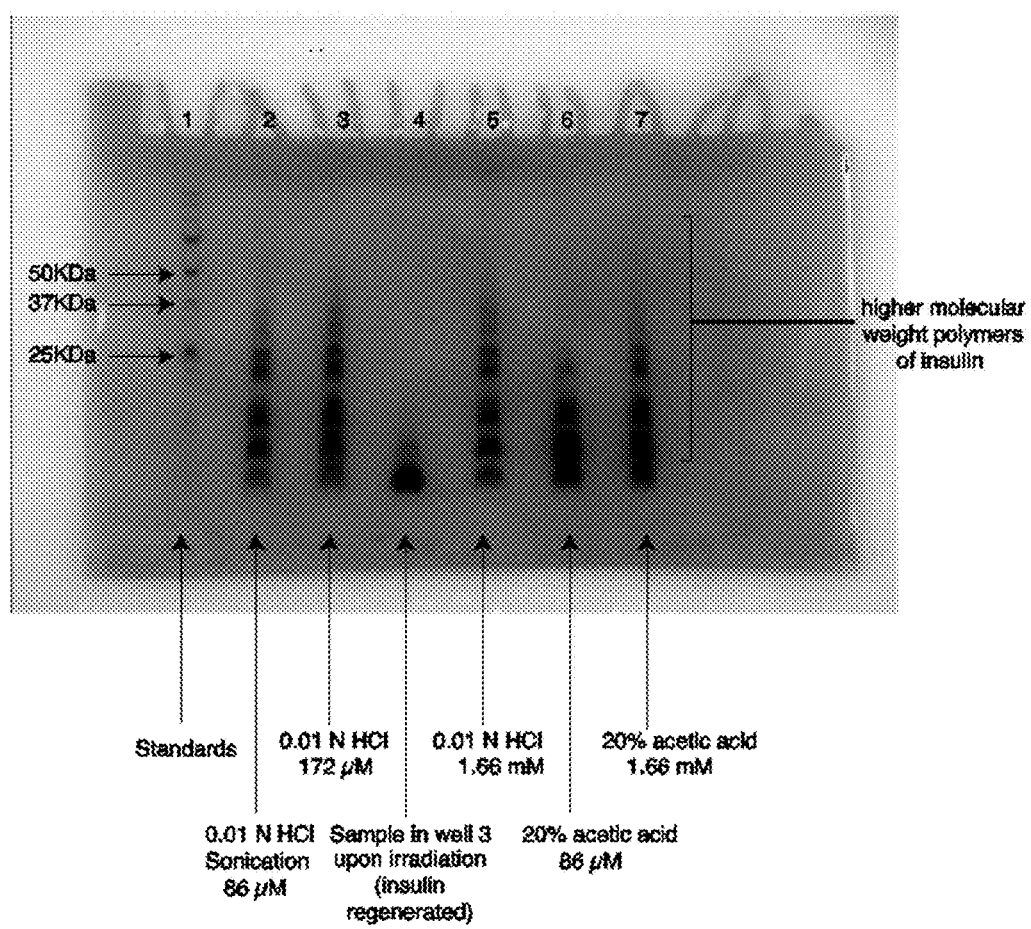

The electrophoresis was run on a criterion midi cell using Criterion TGX (any KDa) precast gel with unstained protein ladder, all purchased from Bio-rad. The sample loading buffer and running buffers were prepared as per the manufacture's guidelines. All the dried samples points were reconstituted in 10 µL solution (5 uL sample loading buffer+ 5 µL DMSO) and loaded onto the gels. The electrophoresis was run for 45 minutes at 160 V. It was stained with Coomassie Brilliant Blue G-250 solution for 2 hours and destained. Gel images were taken by using Gel Doc 2000 (Bio-rad). See FIG. 12F for gel results.

EXAMPLE 10

Meshwork (B) with Zinc

With the photocleavable drug-polymer conjugates and photocleavable drug conjugates, an additional way to increase drug (especially insulin density (and therefore depot lifetime, and photolysis efficiency) is to incorporate additional insulin molecules into the polymer using zinc. This is potentially a way of quickly increasing by many fold the amount of insulin present in any material.

Figure 13:
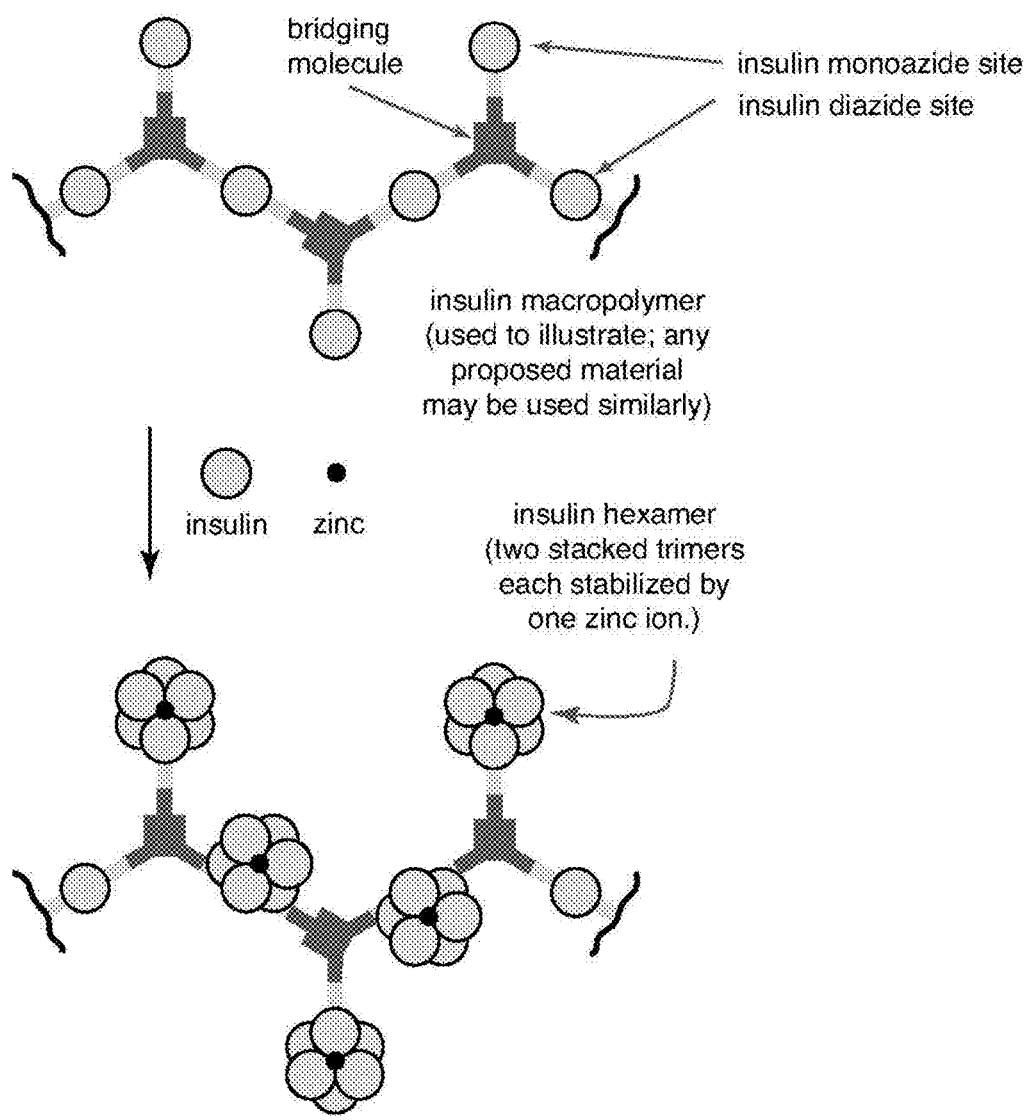
FIG. 13 is a scheme illustrating how hexameric insulin may be incorporated in to the photocleavable drug conjugates of the present invention using zinc.

Briefly, the natural tendency of insulin to form hexamers in the presence of zinc, driven in part by the complexation of the zinc with histidine side chains, is utilized. All of the previously described polymers can be converted into the zinc hexamer equivalent, through the treatment of excess insulin and zinc. This has the potential to significantly increase the amount of insulin incorporated into the material. Such a material will release six monomers per photolysis event, as opposed to a maximum of one per photolysis event in the previously described polymers. The application of zinc addition is illustrated (FIG. 13) through the addition of zinc and insulin to a specific meshwork product.

EXAMPLE 11

Use of an Alternative to Click Conditions

Figure 14:
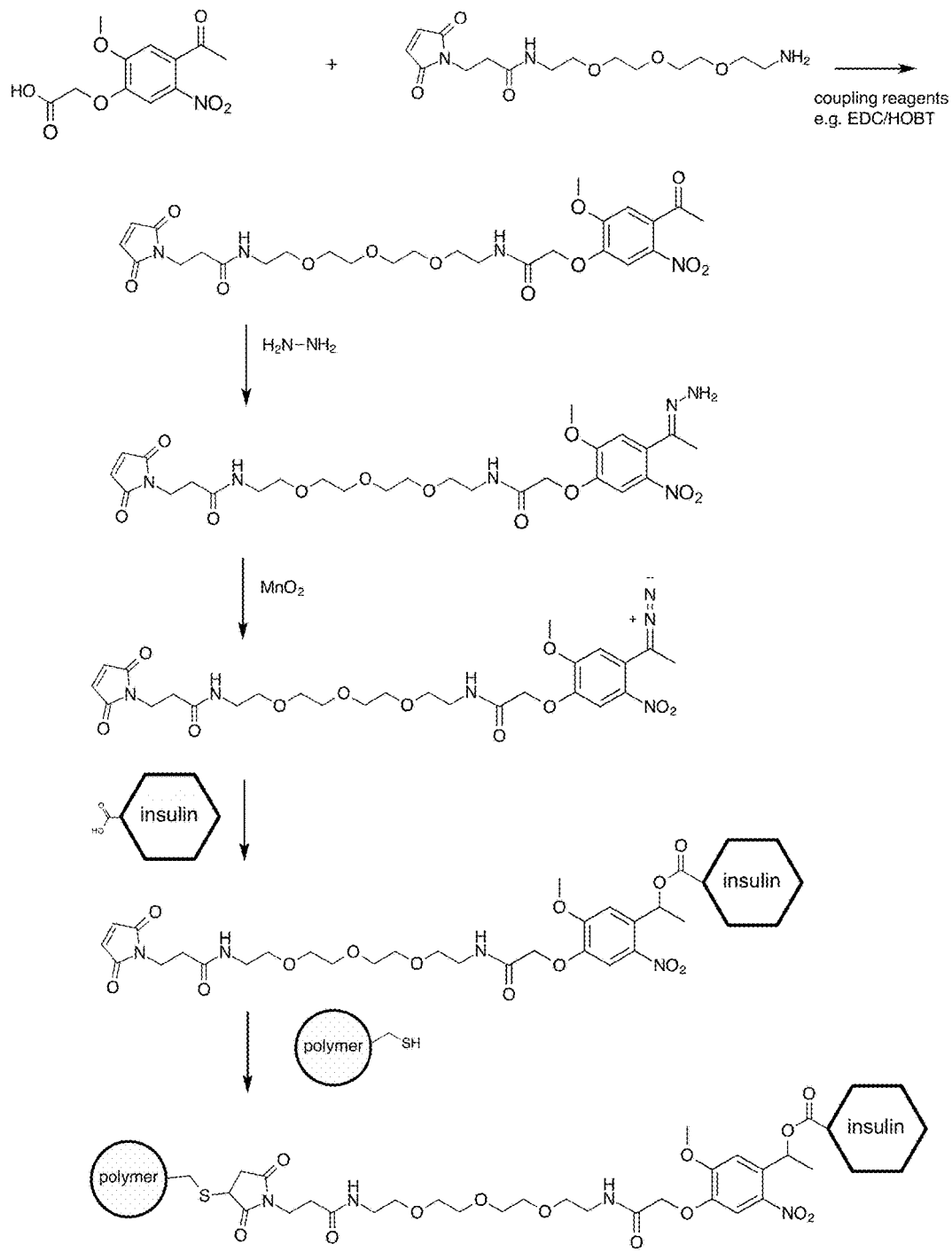
FIG. 14 is an exemplary synthesis for forming a photocleavable drug-polymer conjugate in which the drug is linked to the polymer via a photocleavable group using a maleimide/thiol coupling.

Many of the foregoing examples above utilize "click" chemistry conditions, to allow the coupling of two species, for example a resin and a modified insulin. In the depicted examples, a pair comprising an azide and an alkyne are linked using copper salts and appropriate reagents. While this is a powerful way of linking two species (for example the drug to the resin), there are many other ways of accomplishing this. Example 8 (FIG. 14) illustrates this, and shows how a different reactive pair (a maleimide and thiol) can behave similarly. This example parallels that shown in Example 4, but instead of an alkyne and azide pair that are ultimately linked via a triazole ring, a maleimide/thiol pair is used to make the final link.

A DMNPE-like photocleavable group is linked to a maleimide containing molecule using standard coupling reagents. The ketone group on the resultant molecule is converted to the hydrazone and then diazo using previously described methods. It can then react with functional groups on the insulin. This "insulin maleimide" can then be reacted with a polymer bound thiol group to make the final conjugate.

This illustrates that the previously illustrated examples that use "click" chemistry (including alkynes, azides and resultant triazoles) can be executed using other methods of bioorthogonal linking/coupling.

EXAMPLE 12

Use of an Alternative to DMNPE-Like Photocleavable Groups

While all of the previous examples use a DMNPE-like photocleavable group, it will be appreciated to those skilled in the art that this is just for illustration purposes. There is a vast array of potential photocleavable groups that will have different properties that confer different advantages. One of these properties is the wavelength of deprotection. In the case of DMNPE, this wavelength is approximately 360 nm. Longer wavelengths may allow for the depot to be more deeply located since longer wavelengths penetrate tissue more deeply. In addition, longer wavelengths may have reduced phototoxicity. One way to achieve longer wavelength deprotection is to use photocleavable groups that have the ability to be deprotected by two photons of infrared radiation. This process of absorbing two longer wavelength photons to initiate a process that normally would require one shorter wavelength photon is called "two photon excitation."

Figure 15:
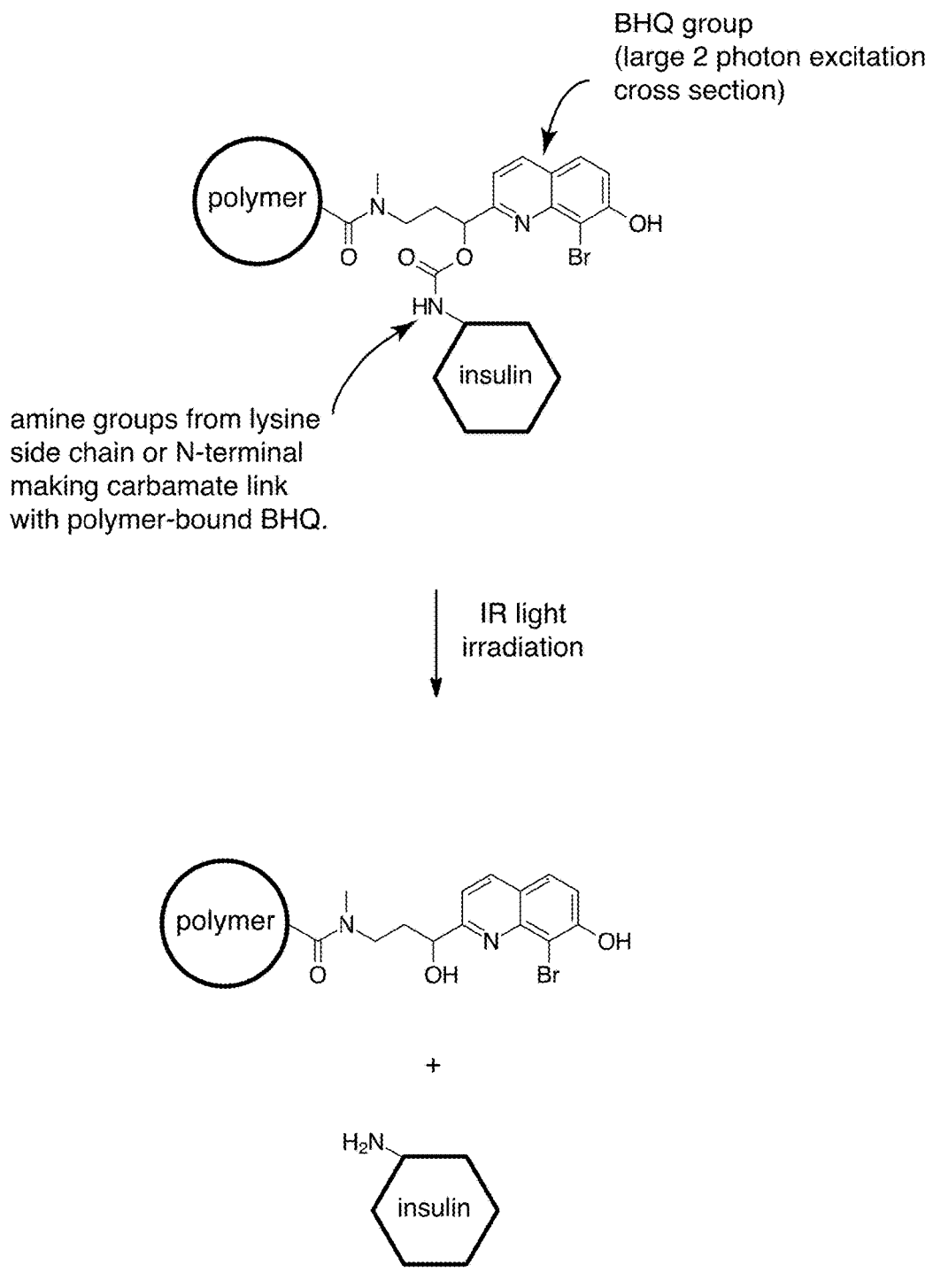
FIG. 15 is an exemplary synthesis for forming a photocleavable drug-polymer conjugate in which the drug is linked to the polymer via a photocleavable group having a bromohydroxyquinoline functionality.

In this Example 9 (FIG. 15), a photoactivated drug depot is created using polymer linked to insulin using a BHQ (8-bromo-7-hydroxyquinoline) derived linker. This group is known to have a significant ability to be cleaved using deeply penetration infrared radiation. In the example, the link to the insulin is made through a carbamate linkage with the insulin contributing the amine that forms the carbamate. Upon photolysis, native insulin is released.

EXAMPLE 13

Dendrimers

Various amine presenting polymers have been described herein, including poly-lysine, Chem-Matrix resin, oligomeric lysine, etc. Such polymers have amino groups that can be modified with other functional groups such as carboxyl groups to make the appropriate materials. These amino groups have been shown being modified by DBCO or DMNPE-carboxylic acid for example. There are a very wide variety of similar polymers that can be used in accordance with the present invention.

Figure 16A:
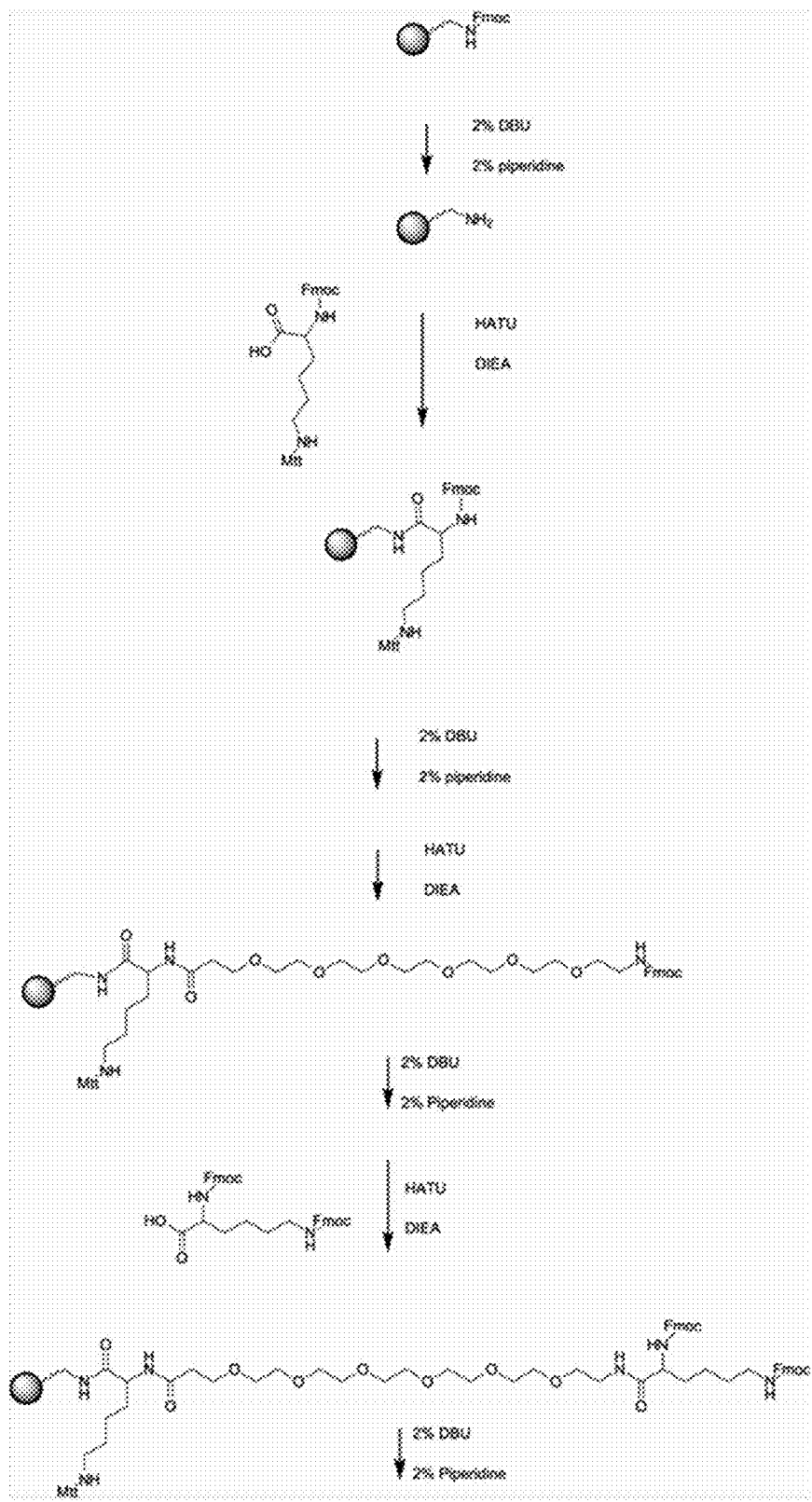
FIGS. 16A to 16C illustrates the synthesis of an amine-containing dendrimer useful in forming the photocleavable drug-polymer conjugates of the present invention.
Figure 16B:
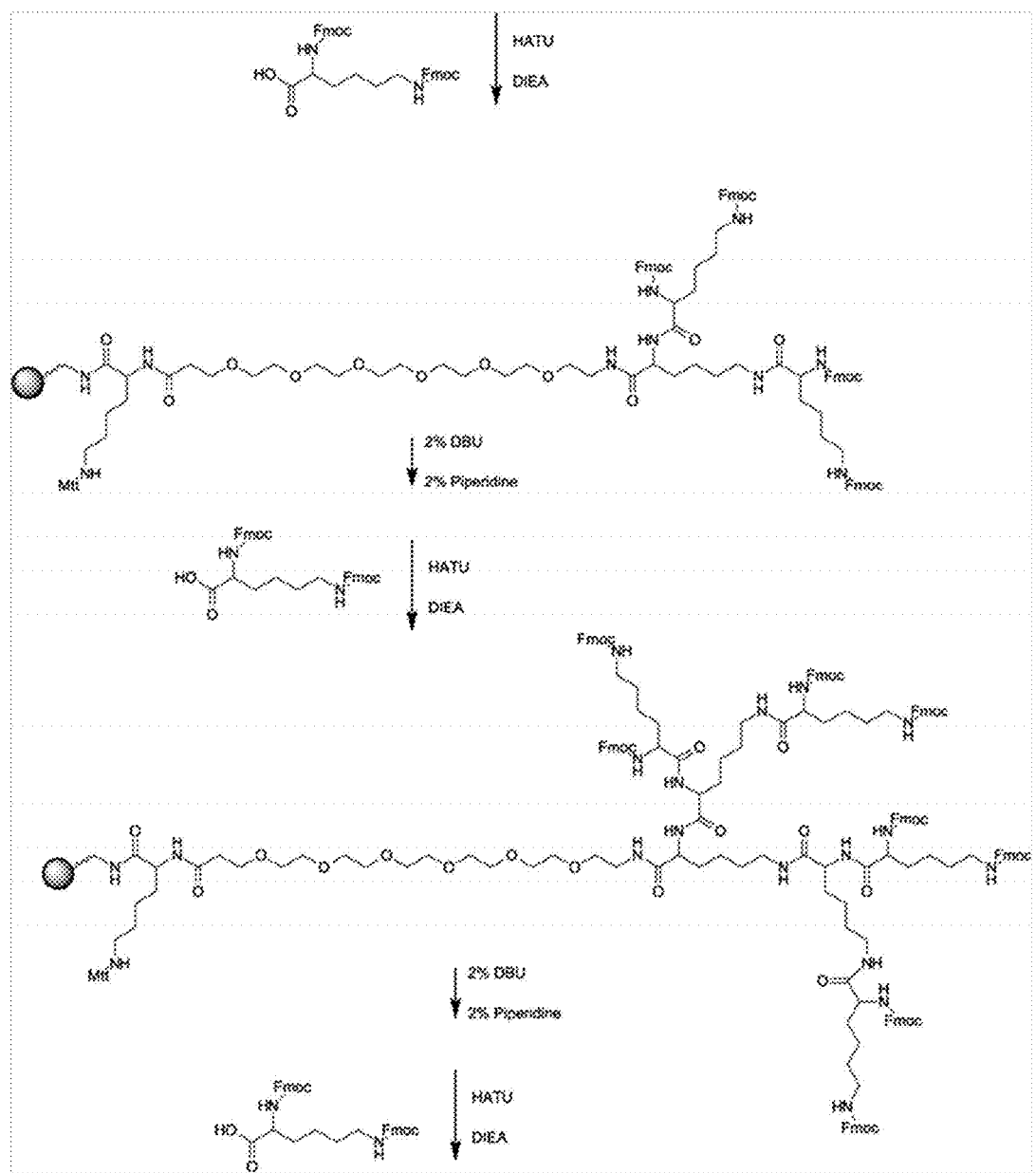
Figure 16C:
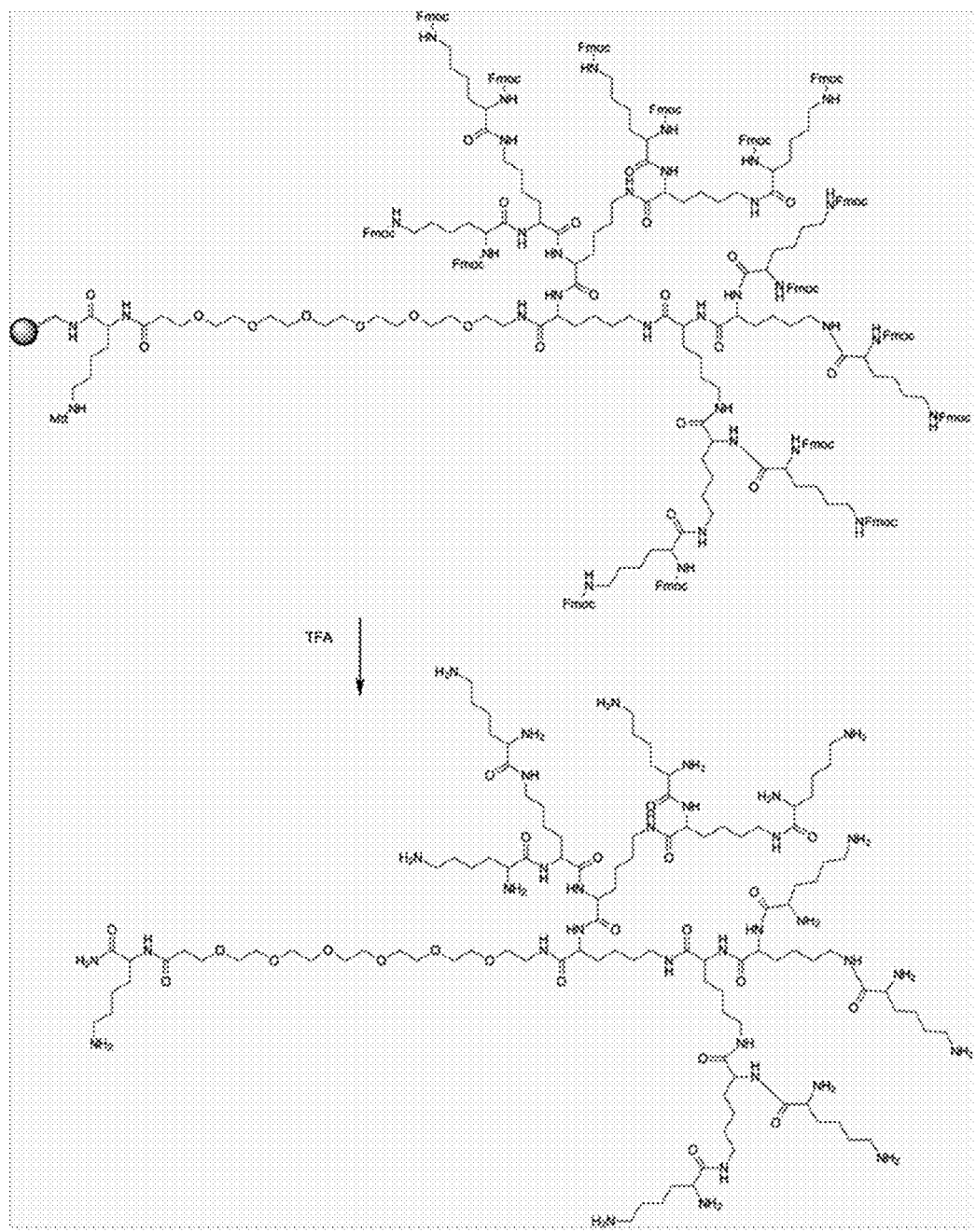

One class of possible polymers that can present equivalent functionality (such as amino groups) are dendrimers. An example dendrimer containing conjugate is shown in FIGS. 16A-16C. The synthesis of this conjugate is initiated by the incorporation of an MTT protected lysine onto a solid phase synthesis resin. To this, an fmoc protected PEG linker is condensed. Finally the full dendrimer is constructed by sequential additions of di-fmoc protected lysine amino acids, using condensation agents such as HBTU/HOBT. The overall size of the dendrimer is controlled by the number of rounds of addition. The resultant species can then be used directly in the identical way that other base resins have been described, namely by incorporation of key monomers such as DBCO and/or DMNPE carboxylic acid.

The following examples describes the preparation of materials that are leading towards the synthesis of the described materials.

EXAMPLE 14

Actual Linear Sequential (A1) Synthesis

Figure 17:
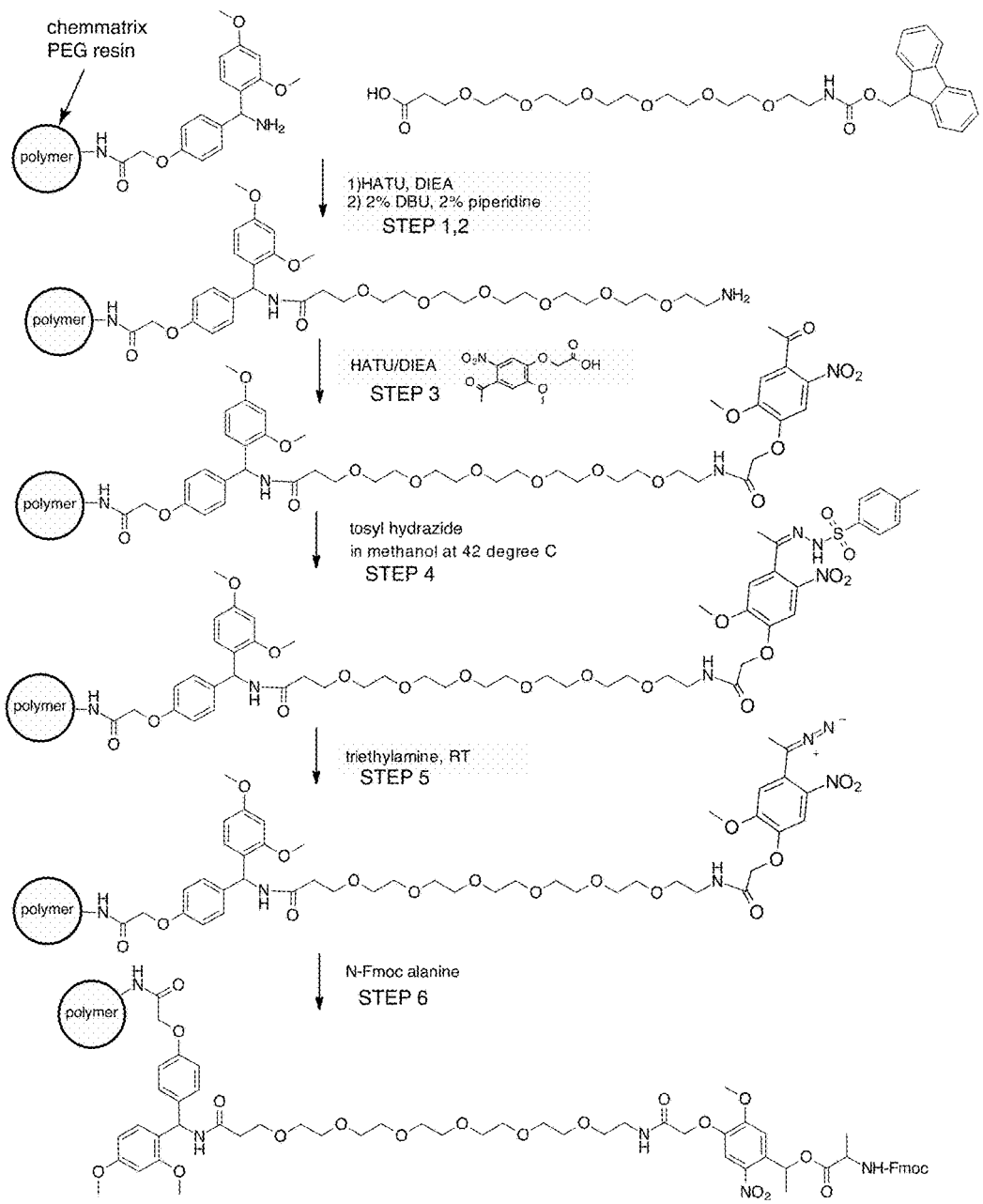
FIG. 17 shows the synthesis for forming a photocleavable drug-polymer conjugate using a linear sequential approach in which alanine (as an exemplary carboxyl-containing compound) is linked to the polymer via a photocleavable group.

Instead of coupling to insulin or other drug in step 6, a model carboxyl containing compound (alanine) is used (FIG. 17).

Step 1: Fmoc-NH-(PEG)5-COOH Linker coupling to chemmatrix resin 0.1111 g of Chemmatrix PEG resin (loading capacity 0.52 mmol/g) was weighed into a manual peptide reactor vessel. The resin was swollen in DMF for 30 minutes and the DMF drained. Fmoc PEG linker (0.2494 g, 433 µmoles), HATU (0.1647 g, 433 µmoles), and DIEA (151 µl, 866 µmoles) were weighed into an eppendorf tube and DMF added to a total volume of 800 µl. Activation of the carboxylic acid was done by agitating on a vortexer for 15 minutes. The activated linker was then added to the PEG resin bed (57.8 µmoles of available amine). The coupling reaction was allowed to proceed overnight. The coupling mixture was drained, the resin bed washed thrice with DMF and a second overnight coupling of the Fmoc linker with the same quantities was performed. At the end of the second coupling the resin bed was washed five times with DMF.

Step 2: Fmoc deprotections with 1,8-Diazabicycloundec-7-ene (DBU)

Deprotection of the resin was done with a 2% DBU, 2% Piperidine mixture. The benzofulvene piperidine adduct resulting from the deprotection was quantitated and gave a coupling yield of 74.8% (43.2 µmoles).

Step 3: Coupling of Nitroketo acid

Nitroketo acid 0.1166 g (433 µmoles), HATU (0.1647 g, 433 µmoles), and DIEA (151 µl, 866 µmoles) were weighed into an eppendorf tube and DMF added to a total volume of 800 µl. The carboxylic acid was activated for 15 minutes and the activated mixture added to the deprotected resin of step 2.

Step 4: Conversion of Ketone to Hydrazone

A quantity of resin containing 14 µmoles of the nitroketo acid was transferred to an eppendorf tube. It was washed five times with DMF, five times with methanol and drained. A solution of Tosylhydrazone (0.1064 g, 570 µmoles) in a total volume of 1 ml anhydrous methanol was added to the eppendorf tube and the entire contents transferred to a RB flask. A condenser unit was attached to the flask. The contents were stirred overnight with the aid of a magnetic stirrer while being heated at 40° C.

Step 5: Conversion of Hydrazone to Diazo

The beads from step 4 were collected and the reaction mixture removed. The beads were washed five times with anhydrous methanol. Thereafter, Triethylamine was added to the beads and stirred for 1 hour. The conversion of the hydrazone to the diazo was indicated by an immediate change in color of the beads from yellow to deep red. At the end of an hour the triethylamine was removed and the beads were washed five times with anhydrous DMSO.

Step 6: Formation of Esters of Fmoc-Alanine 0.0581 g of Fmoc-alanine was dissolved in 342 µL of DMSO. P-toluene sulfonic acid monohydrate (12 µmoles) was also added. The solution was added to the diazotized beads in an eppendorf tube. The tube was agitated gently by rotating end over end overnight.

Step 7: Cleavage of the Construct from the Resin

The reaction mixture was drained from the beads. They were then washed five times with methanol and five times with ether. The last wash of ether was removed and the beads dried thoroughly using a rotovap. Cleavage of the construct from the beads was accomplished by subjecting the beads for 1 hour to a TFA/water (95/5) mixture. The beads were separated from the cleavage solution and washed twice with TFA/water (95/5). The combined cleavage solution was evaporated to dryness and made up with DMF.

EXAMPLE 15

Actual Linear Convergent (A2) Synthesis

Figure 18:
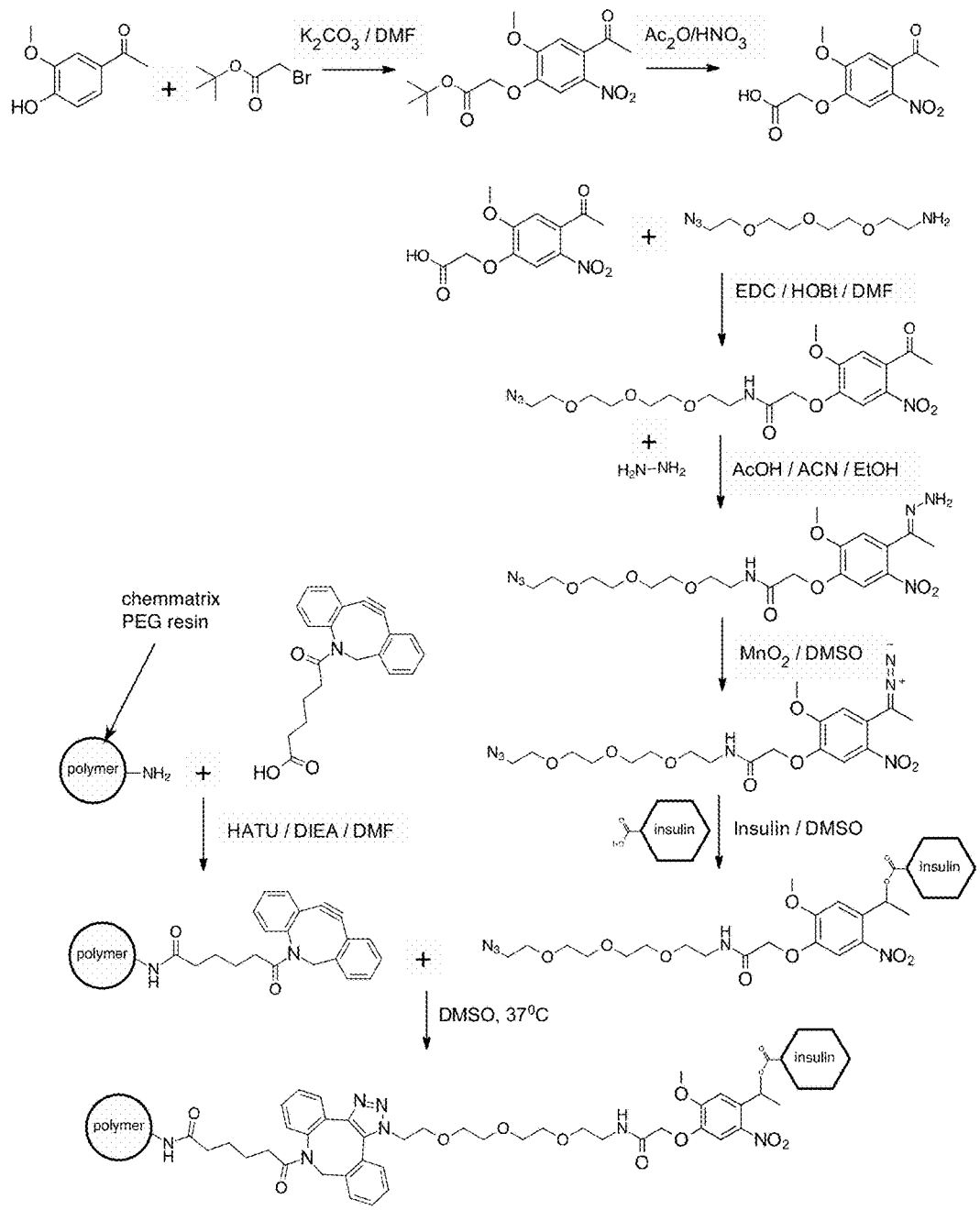
FIG. 18 shows the synthesis for forming a photocleavable drug-polymer conjugate using a linear convergent approach in which photocleavable group is linked to the polymer using a triazole bridge.

FIG. 18 is a schematic showing the actual linear convergent (A2) synthesis employed in this example.

Materials

Acetovanillone (or 1-(4-Hydroxy-3-methoxy-phenyl)-ethanone), t-butyl bromoacetate (or bromo-acetic acid tert-butyl ester), nitric acid, 11-azido-3,6,9-trioxaundecan-1-amine (or 2-{2-[2-(2-Azido-ethoxy)-ethoxy]-ethoxy}-ethylamine or AP-amine), magnesium sulfate, hydrazine, manganese dioxide, HATU and human recombinant insulin were purchased from Sigma Aldrich. DMF, DMSO, DCM, acetonitrile, methanol, ethanol, ethyl acetate, sodium chloride, potassium carbonate, trifluoroacetic acid, acetic anhydride, 1 N HCl, diethyl ether, sodium bicarbonate and Celite545 were purchased from Fisher Scientific. DBCO acid (Click Chemistry Tools), hydroxybenzotrizole hydrate (Peptide International), 1-ethyl-3-(3-dimethyl aminopropyl) carbodiimide hydrochloride (Calbiochem), ChemMatrix resin (Biotage), Centrifugal filter 5K NMWL membrane (Millipore).

Methods

Compound 1: DMNPE-ester or (4-Acetyl-2-methoxy-phenoxy)-acetic acid tert-butyl ester Compound 1 was synthesized by following the literature (Holmes, C. P. J. Org. Chem. 62 2370-2380 (1997)). Briefly, acetovanillone (2.63 g, 15.8 mmol), tert-butyl bromoacetate (2.56 mL, 17.3 mmol) and potassium carbonate (3.60 g, 26.0 mmol) were mixed in 18.75 mL of solvent N,N-dimethylformamide (DMF). This slurry was stirred at room temperature under nitrogen for 60 hours. Salts were dissolved by adding 100 mL of water and the resultant white precipitate was further purified by partitioning between ethyl acetate and saturated sodium chloride solution. Combined organic layer was washed with saturated sodium chloride solution, dried using magnesium sulfate and evaporated to yield shiny white powder of DMNPE-ester. Yield 4.35 g (98%), Purity (>99% from NMR), TLC (EtOAc/MeOH, 75:25 v/v): $R_f$=0.7; $^1$H NMR (400 MHz, DMSO-$d_6$): δ 7.53 ppm (d, J=8.4 Hz, 1H), 7.42 (s, 1H), 6.89 (d, J=8.8); $^{13}$C NMR (100 MHz, DMSO-$d_6$): δ 199.3, 165.8, 153.5, 147.8, 137.6, 132.1, 109.9, 108.7, 67.7, 56.6, 44.1, 30.0, 29.8, 23.3, 23.1, 22.8, 21.3; UV/vis (DMSO): $\lambda_{max}$ ($\varepsilon_\lambda$) in DMSO: 262 nm (8037 M$^{-1}$ cm$^{-1}$), 343 nm (4500 M$^{-1}$ cm$^{-1}$); MS (m/z): [MH]$^+$ calcd for $C_{15}H_{20}NO_5$, 281.1; found, 281.5; reversed phase HPLC-MS (flow rate 0.3 mL/min, runtime 30 minutes, injection volume 25 μL) solvent A (0.1% formic acid in $H_2O$), solvent B (0.1% formic acid in acetonitrile (ACN)), gradient 50% B to 100% B over 10 minutes, isocratic 100% B for 17 minutes, 100% B to 0% B over 3 minutes, $C_8$ Hypersil column (5 μm, 100×4.6 mm, Varian): retention time (min) 17.21; ESI-MS (m/z): [MH]$^+$ calcd for $C_{15}H_{20}NO_5$, 281.1; found, 281.5.

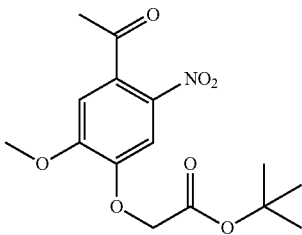 [SMILES: COc1cc(C(C)=O)c([N+](=O)[O-])cc1OCC(=O)OC(C)(C)C]

Compound 2: DMNPE-acid or (4-Acetyl-2-methoxy-5-nitro-phenoxy)-acetic acid

Compound 2 was synthesized by following the literature (Holmes, 1997). To an ice cold solution of nitric acid (4 mL) and acetic anhydride (2.7 mL), a solution of compound 1 (1.00 g, 3.6 mmol) in acetic anhydride (4 mL) was slowly added. The solution was stirred for 2 hours in ice and then for 4 hours at room temperature. The mixture was poured to ice cold water (25 mL) and kept at 4° C. for overnight. Precipitate was filtered, washed with ice cold water and dried in rotovap to obtain off-white product. Yield 407.0 mg (42%), Purity (99%, NMR); TLC (EtOAc/MeOH, 75:25 v/v): $R_f$=0.3; $^1$H NMR (400 MHz, DMSO-$d_6$): δ 7.53 ppm (s, 1H), 7.20 (s, 1H), 9 (d, J=8.8); $^{13}$C NMR (100 MHz, DMSO-$d_6$): δ 199.3, 165.8, 153.5, 147.8, 137.6, 132.1, 109.9, 108.7, 67.7, 56.6, 44.1, 30.0, 29.8, 23.3, 23.1, 22.8, 21.3; UV/vis (DMSO): $\lambda_{max}$ ($\varepsilon_\lambda$) in DMSO: 262 nm (8037 M$^{-1}$ cm$^{-1}$), 343 nm (4500 M$^{-1}$ cm$^{-1}$); MS (m/z): [MH]$^+$ calcd for $C_{11}H_{11}NO_7$, 270.1; found, 270.2; reversed phase HPLC-MS (flow rate 0.4 mL/min, runtime 30 minutes, injection volume 25 μL) solvent A (0.1% formic acid in $H_2O$), solvent B (0.1% formic acid in acetonitrile (ACN)), gradient 0% A to 100% B over 27 minutes, isocratic 100% B for 2 minutes, 100% B to 0% A over 1 minute, $C_8$ Hypersil column (5 μm, 100×4.6 mm, Varian): retention time (min) 13.94; ESI-MS (m/z): [MH]$^+$ calcd for $C_{11}H_{11}NO_7$, 270.1; found, 270.2.

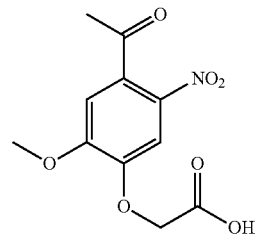 [SMILES: COc1cc(C(C)=O)c([N+](=O)[O-])cc1OCC(=O)O]

Compound 3: AP-DMNPE Amide or 2-(4-Acetyl-2-methoxy-5-nitro-phenoxy)-N-(2-{2-[2-(2-azido-ethoxy)-ethoxy]-ethoxy}-ethyl)-acetamide Compound 2 (50.2 mg, 187 μmol), 11-Azido-3,6,9-trioxaundecan-1-amine (37.7 μL, 190 μmol) and hydroxybenzotrizole hydrate (56.6 mg, 370 μmol) were dissolved in 675 μL of dimethylformamide (DMF). To this solution, 1-Ethyl-3-(3-dimethylaminopropyl)carbodiimide hydrochloride (61.34 mg, 320 μmol) was added and shaken for 23 hours. The product was purified by partitioning the reaction mixture between ethyl acetate (25 mL) and saturated sodium chloride (25 mL). The ethyl acetate layer was washed twice with saturated sodium chloride solution and the combined aqueous layers were washed once with ethyl acetate. The combined organic layers were washed with 1 N HCl, and saturated sodium bicarbonate solution. The organic layer was then dried with magnesium sulfate and evaporated to yield a viscous yellow residue. Yield 87.0 mg (99.4%), Purity (>99%, NMR), TLC (EtOAc/MeOH, 75:25 v/v): Rf=0.56; 1H NMR (400 MHz, DMSO-d6): δ 8.13 ppm (t, J=11.2 Hz, 1H), 7.61 (s, 1H), 7.26 (s, 1H), 4.69 (s, 2H), 3.96 (s, 3H), 3.59 (t, J=9.6 Hz, 2H), 3.56-3.50 (m, 6H), 3.45 (t, J=11.6 Hz, 2H), 3.38 (t, J=10.0 Hz, 2H), 3.29 (m, 2H), 2.53 (s, 3H), 2.50 (s, 2H); 13C NMR (100 MHz, DMSO-d6): δ 199.3, 166.7, 153.5, 147.6, 137.7, 132.2, 109.9, 109.0, 69.7, 69.6, 69.5, 69.1, 68.8, 67.7, 56.6, 49.8, 38.3, 30.0; UV/vis (DMSO): $\lambda_{max}$ ($\varepsilon_\lambda$): 262 nm (8037 M$^{-1}$ cm$^{-1}$), 343 nm (4500 M$^{-1}$ cm$^{-1}$); MS (m/z): [MH]$^+$ calcd for $C_{19}H_{27}N_5O_9$, 470.2; found, 470.3; reversed phase HPLC-MS (flow rate 0.4 mL/min, runtime 30 minutes, injection volume 25 μL) solvent A (0.1% formic acid in $H_2O$), solvent B (0.1% formic acid in acetonitrile (ACN)), gradient 0% B to 100% B over 27 minutes, isocratic 100% B for 2 minutes, 100% B to 0% B over 1 minute, $C_8$ Hypersil column (5 μm, 100×4.6 mm, Varian): retention time (min) 18.88; ESI-MS (m/z): [MH]$^+$ calcd for $C_{19}H_{27}N_5O_9$, 470.2; found, 470.2.

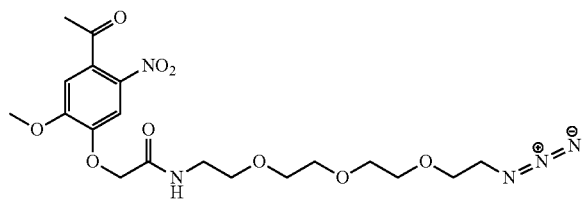 [SMILES: COc1cc(C(C)=O)c([N+](=O)[O-])cc1OCC(=O)NCCOCCOCCOCCN=[N+]=[N-]]

Compound 4: AP-DMNPE Hydrazone or N-(2-{2-[2-(2-Azido-ethoxy)-ethoxy]-ethoxy}-ethyl)-2-[4-(1-hydrazono-ethyl)-2-methoxy-5-nitro-phenoxy]-acetamide Compound 3 (29.8 mg, 63 μmol) was dissolved in 2.4 mL of a 1:1 mixture of acetonitrile and ethanol. Hydrazine monohydrate (40.6 μL, 839 μmol) and glacial acetic acid (20.3 μL, 355 μmol) were added to the solution and the mixture was heated for 5 hours at 90° C. in a glass reaction vial. The resulting yellow oily solution was evaporated to dryness, dissolved in dichloromethane (DCM; 2 mL) and then purified using silica gel flash column chromatography with 5%-10% methanol in DCM. Fractions were collected, dried, and analyzed by LC-MS. Appropriate fractions were combined and used for the next reaction. The crude contained a mixture of 2 isomers, E and Z. Yield 32.4 mg (98.2% yield). TLC (EtOAc/MeOH, 75:25 v/v): $R_f$=0.35 & 0.46; Yield 32.4 mg (98.2% yield), Purity (>90%, NMR). TLC (EtOAc/MeOH, 75:25 v/v): $R_f$=0.35 & 0.46; $^1$H NMR (400 MHz, DMSO-$d_6$, E or Z isomers, ratio of isomer 1/isomer 2=1:3): isomer 1 [δ 8.08 ppm (t, J=10.8 Hz, 1H), 7.46 (s, 1H), 7.00 (s, 1H), 6.42 (s, 2H), 4.62 (s, 2H), 3.92 (s, 3H), 3.59 (t, J=9.6 Hz, 2H), 3.56-3.50 (m, 8H), 3.46 (t, J=11.2 Hz, 2H), 3.31 (t, J=11.6 Hz, 2H), 3.39 (s, 3H), 1.93 (s, 2H)]; isomer 2 [δ 8.13 ppm (t, J=11.2 Hz, 1H), 7.71 (s, 1H), 7.25 (s, 1H), 6.71 (s, 2H), 4.56 (s, 2H), 3.87 (s, 3H), 3.59 (t, J=9.6 Hz, 2H), 3.56-3.50 (m, 8H), 3.46 (t, J=11.2 Hz, 2H), 3.31 (t, J=11.6 Hz, 2H), 3.39 (s, 3H), 2.08 (s, 2H)]; $^{13}$C NMR (100 MHz, DMSO-$d_6$): only isomer 1 peaks visible δ 167.1, 152.3, 145.7, 140.4, 139.9, 131.5, 112.2, 109.6, 69.8, 69.7, 69.6, 69.5, 69.2, 68.8, 56.2, 49.9, 39.0, 15.0; UV/vis (DMSO): $\lambda_{max}$ ($\varepsilon_\lambda$): 263 nm (7323 M$^{-1}$ cm$^{-1}$), 346 nm (4470 M$^{-1}$ cm$^{-1}$); reversed phase HPLC-MS (exact conditions as used for compound 3): retention time (min) 19.94, 20.67; ESI-MS (m/z): [MH]$^+$ calcd for $C_{19}H_{29}N_7O_8$, 484.2; found, 484.1.

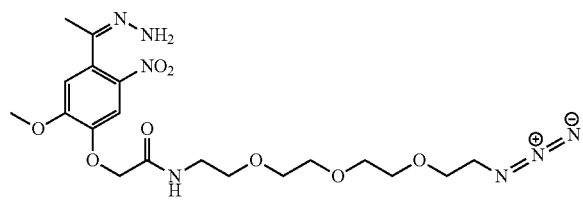 [SMILES: COc1cc(/C(C)=N\N)c([N+](=O)[O-])cc1OCC(=O)NCCOCCOCCOCCN=[N+]=[N-]]

Compound 5: AP-DMNPE diazo or N-(2-{2-[2-(2-Azido-ethoxy)-ethoxy]-ethoxy}-ethyl)-2-[4-(1-diazo-ethyl)-2-methoxy-5-nitro-phenoxy]-acetamide Manganese (IV) oxide (20 mg, 230 mop was added to a solution of compound 4 (4 mg, 8.28 μmol) in 50 μL of anhydrous dimethyl sulfoxide. This mixture was shaken gently for 45 minutes keeping it protected from light. The red-black mixture was centrifuged and the supernatant was filtered through Celite 545 using glass-wool/glass-pipette. This celite pad was washed with 150 μL of dimethyl sulfoxide. Compound 5 was freshly prepared each time to cage insulin (described later). Compound 5 was not isolated or further characterized, beyond its UV-visible spectrum. The UV-vis analysis showed peaks at 280, 346, and 450 nm.

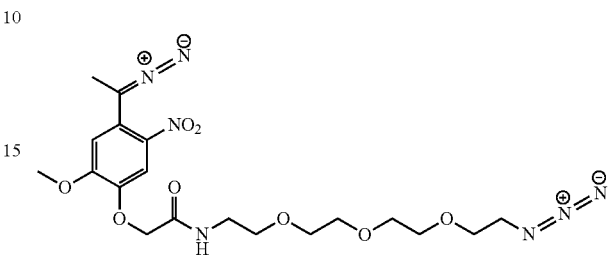

Compound 6: Insulin Azide

Freshly prepared compound 5 (1.9 mg, 4 μmol) in DMSO (100 μL) was added to a solution of human recombinant insulin (1.9 mg, 320 nmol) in DMSO (100 μL). The mixture was gently shaken for 21 hours, protected from light. Mixture was dried in freeze dryer to remove DMSO, reconstituted in 0.01 N HCl (200 μL), and then purified using Biomax—5 K NMWL membrane centrifugal filter & tube. By following manufacturer's protocol, caged insulin was purified from small molecular weight reagents using ultracentrifuge. In addition, concentrated solution of caged insulin in filter was washed twice with 0.01 N HCl and centrifuged. Caged insulin was recovered in 0.01 N HCl (400 μL), freeze dried, reconstituted in DMF (50 μL) and different levels of modified insulin was separated using reversed phase HPLC. Flow rate 0.4 mL/min, runtime 30 minutes, injection volume 45 μL solvent A (0.1% Trifluoroacetic acid in H$_2$O), solvent B (0.1% Trifluoroacetic acid in acetonitrile (ACN)), gradient 0% B to 100% B over 29 minutes, 100% B to 0% B over 1 minute, 5 minutes post run at 0% B. $C_{18}$ Hypersil column (5 μm, 100×4.6 mm, Varian): retention time of various modified insulin (min) Unmodified 15.4, mono-modified 15.9, Di-modified 16.4, higher-modified 17.1.

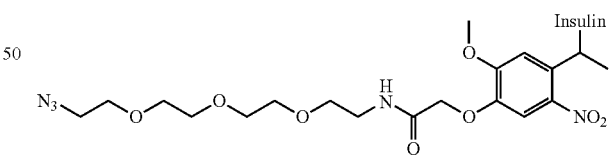

DBCO Conjugated Resin

ChemMatrix resin (10.0 mg, 5.5 ttmols of amino groups, 138 mM) or SpheriTide resin (10.0 mg, 10 μmols of amino groups, 250 mM) were used as solid matrix for coupling DBCO acid. Procedure for each type of resin is as follows. Resin was washed twice with DMF (500 μL). A solution of DBCO acid (2 mg, 6 μmols, 150 mM), HATU (2.3 mg, 6 μmols, 150 mM) and N,N-diisopropylethylamine (2.09 μL, 12 μmols, 300 mM) in DMF (34 μL) was shaken for 15 minutes. This activated solution was added to the swollen resin and was gently stirred for 22 hours. Resin was washed multiple times with DMF and DMSO before using for the next step reaction. Attachment of DBCO acid was tested by cleaving a small amount of the resin (0.5 mg). Resin was washed several times with DMF, methanol and ether, dried in the vacuum and then treated with 95% TFA (500 µL) for 2 hours. Cleaved product DBCO amide was recovered by drying off TFA under vacuum and was further analyzed by HPLC and MS.

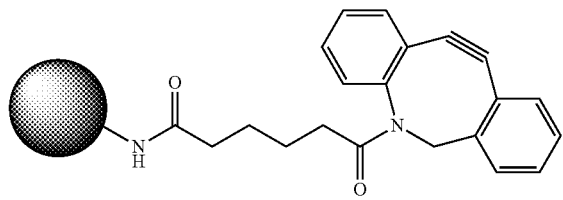 [SMILES: CNC(=O)CCCCC(=O)N1Cc2ccccc2C#Cc2ccccc21]

Insulin Conjugated Resin (Using Cu-Free Click Chemistry)

Spin filtered insulin azide (2.7 mg, 450 nmol) containing a mixture of uncaged insulin and insulin azide in the ratio of 2:1 was dissolved in DMSO to make up the volume to 15 µL. This insulin (1.8 mg, 300 nmol, 20 mM) and insulin azide (0.9 mg, 150 nmol, 10 mM) solution was added to the pre-swollen DBCO conjugated resin (3.1 mg, approx 1.4 µmols alkyne) and mixture was stirred for 33 hours at 37° C. protected from light. After reaction, resin was washed several times with DMSO and methanol. One half of the resin was washed several times with water and then used for photolysis studies. Other half of the resin was washed with ether, dried in vacuum and then cleaved the product with 95% TFA (500 µL) for 2 hours. Cleaved insulin-triazole product was obtained by evaporating TFA under vacuum and was further analyzed using HPLC and MS.

EXAMPLE 16

Photo Release Studies

Two samples were examined, a "test" sample and a "control" sample. The test sample contained 7.1 mg of ChemMatrix resin (28 7 mg wet weight) that had been modified with DBCO and then conjugated with 375 nmols insulin azide as generally described in the prior example. The control samples was prepared in an analogous fashion, except that an unmodified ChemMatrix resin was treated with 375 nmols of uncaged insulin (control). Both test and control samples were suspended in 100 µL of RNase free water in a flat-bottom glass tube. Each sample was shaken and centrifuged before irradiation. The glass tube was positioned directly on the surface of the UV point source for irradiation studies. The point source was a Nichia 365 nm 200 nW LED. The tube was irradiated for a given period of time. Then a sample was taken. The first 5 samples followed 1 minute irradiations. The next 3 samples followed 2 minute irradiations. The final two samples followed five minute irradiations. In between points of irradiation, sample was stored in the dark for 4 minutes. 25 µL of sample was taken first immediately after irradiation and same volume was taken after storing sample in the dark. Then volume was made up to 100 µL by addition of RNase free water before next round of irradiation.

Figure 19A:
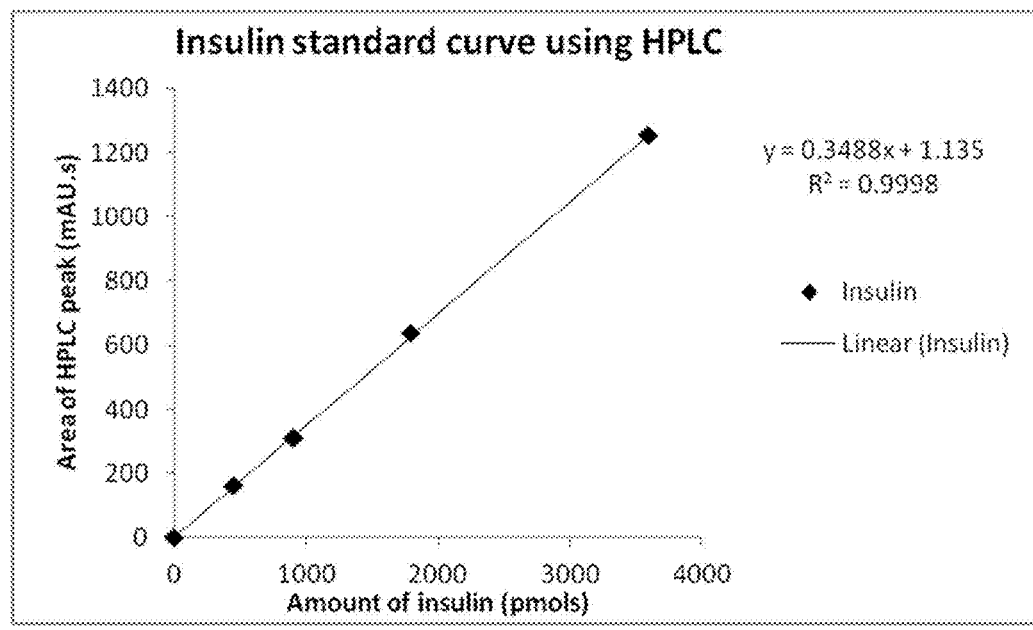
FIG. 19A is the standard curve for the HPLC analysis of the insulin.
Figure 19B:
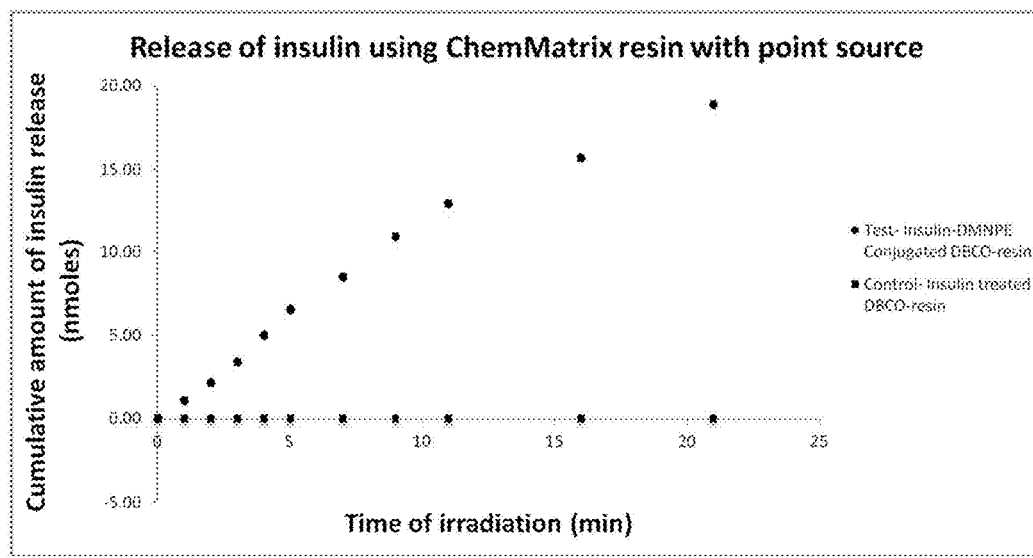
Figure 19C:
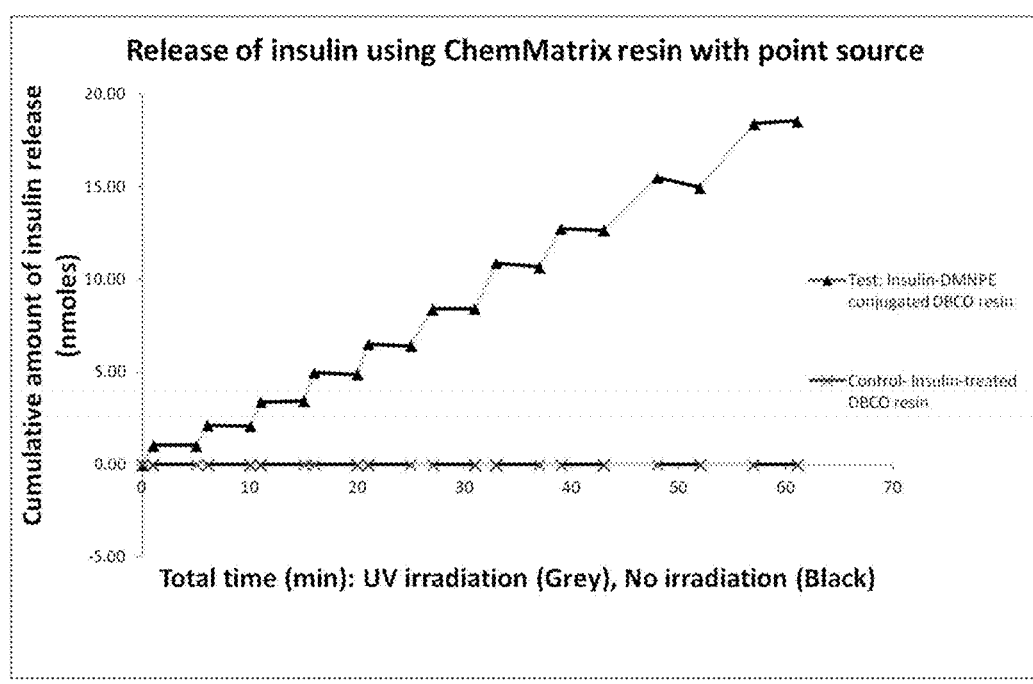
FIG. 19C shows the cumulative amount of insulin released as a function of total time of irradiation.

Each sample removed was diluted to 50 µL using RNase free water and then 45 µL was of the sample was injected into HPLC for analysis. A standard curve was generated using HPLC by injecting variable moles of unmodified insulin and analyzing peak area from the chromatogram at 280 nm, which is shown in FIG. 19A. The amount of moles of insulin released from photolysis was calculated using peak area from HPLC using a standard curve. The cumulative amount of insulin released vs. time of irradiation (FIG. 19B) or total time duration (FIG. 19C) was determined. Photo released insulin was further confirmed using mass spectrometry.

EXAMPLE 17

In-Vivo Testing of Light Activated Insulin Depot

In vivo testing of the light activated depot will initially be based on an animal model, such as a rat or mouse. A small volume of depot material will be injected subcutaneously under the skin of the model animal. The skin above this site will be shaved and a compact light source will be attached, for example an LED. The wavelength of light that is emitted will depend on the specific photocleavable group used in the depot. The light source will initially be off. At regular

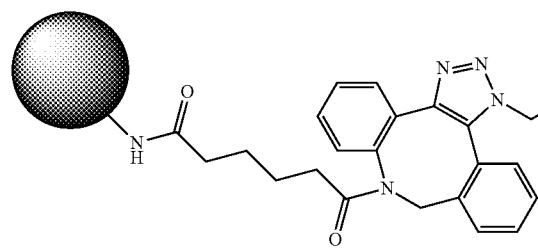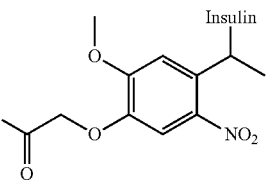

intervals, small amounts of blood will be collected from the animal. These will be analyzed for the presence of the drug (e.g., insulin) using, for example, an ELISA assay specific for the drug. After a period of time, the light source will be activated for a period of time. Regular blood collection will continue and the change in blood insulin levels examined, as a function of light irradiation of the site. Control animal(s) will have the same injection and light source attached, but the light path will be blocked by a mask or patch. This is to control for any effect of the light source that has nothing to do with light itself (i.e., heat, compression of attachment site, etc.). Significant differences in the blood insulin levels between irradiated and unirradiated animals will be observed. There are multiple parameters that may be varied, including the duration of irradiation, the intensity of the irradiation, the depth of the subcutaneous injection, and the duration of time during which blood sampling takes place. The light exposure—response may depend upon the light permeability of the overlying tissue and the amount of that tissue. The same setup can also be used to sample blood glucose levels as a function of the irradiation. It is anticipated that the photo-released insulin, being fully native and functional, will stimulate uptake of blood glucose by cells, and in so doing, reduce the overall blood concentration in a light dependent manner.

It will be appreciated that independent of the pathway to the final conjugate material, it can be implanted (typically injected cutaneously or subcutaneously) to form a depot. This depot can then be irradiated through the skin in response to physiological signals (e.g., blood sugar levels in the case of diabetes), to cleave the link of the resin with the insulin. The insulin can then diffuse into the general systemic circulation, where it can exert its therapeutic benefit.

From the foregoing, it will be seen that this invention is one well adapted to attain all ends and objectives herein above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:
1. A depot suitable for implantation into a patient comprising a photocleavable drug conjugate,
said photocleavable drug conjugate comprising a plurality of drug molecules crosslinked to other drug molecules with a plurality of crosslinkers;
wherein the drug molecules are selected from the group consisting of insulin, its analogs, its derivatives and combinations thereof;
wherein the crosslinkers comprise crosslinkers having 2 to 5 photocleavable groups linked to a central bridging molecule;
wherein the conjugate does not comprise a polymer chain that functions as a backbone; and
wherein the ratio of the insulin to the crosslinkers is from 80:20 to 95:5 based on molecular weight.
2. The depot of claim 1 wherein said photocleavable group is cleaved upon exposure to visible light.
3. The depot of claim 1 wherein said photocleavable group is cleaved upon exposure to ultraviolet light.
4. The depot of claim 1 wherein said photocleavable group has an ortho-nitro aromatic core scaffold.
5. The depot of claim 1 wherein said photocleavable group is selected from the group consisting of coumarins, acridines, nitroaromatics, and arylsulfonamides.
6. The depot of claim 1 wherein said insulin is native insulin.
7. The depot of claim 1 wherein said drug molecules comprise insulin in a hexameric form combined with zinc.
8. The depot of claim 1 wherein said drug molecules comprise drug molecules having a plurality of amine functionalities and the photocleavable group has a plurality of n-hydroxy succinamide ester functionalities, and wherein said crosslinking comprises forming a carbamate from said amine functionalities and said n-hydroxy succinamide ester functionalities.
9. The depot of claim 1 wherein said crosslinking occurs via triazole bridging between said drug molecules and said crosslinkers.
10. The depot of claim 9 wherein said photocleavable group has an azide functionality, and wherein said crosslinking occurs via an alkyne platform having two or more alkynes.
11. The depot of claim 10 wherein said insulin molecules are selected from the group consisting of an insulin monoazide, an insulin diazide, an insulin triazide, and combinations thereof.
12. The depot of claim 10 wherein said alkyne platform comprises two or more dibenzylcyclooctyne groups.
13. The depot of claim 10 wherein said alkyne platform is selected from the group consisting of:

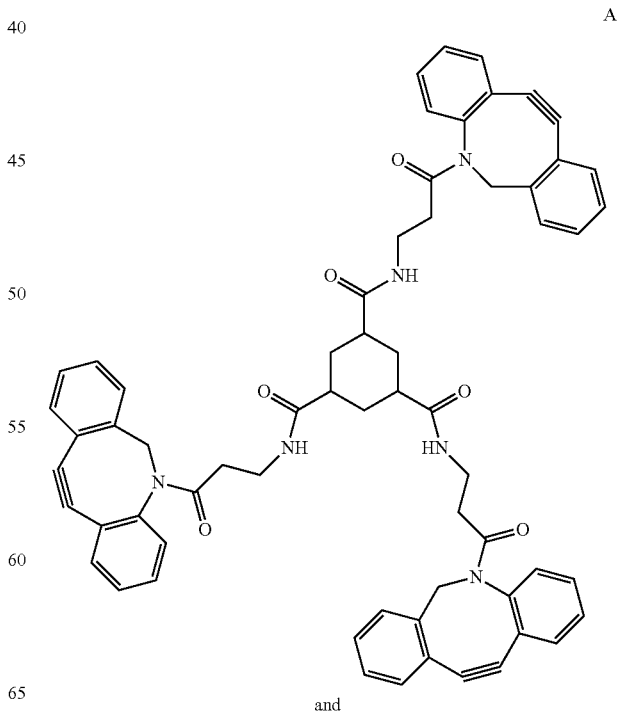

and

-continued

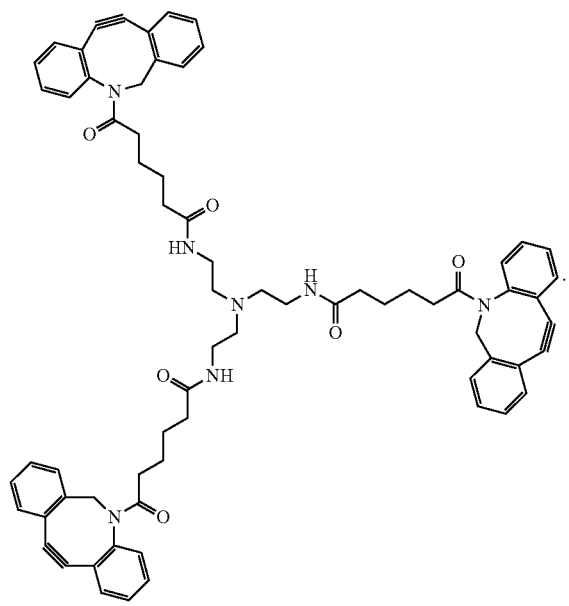

14. The depot of claim 10 wherein said alkyne platform defined according to:

B

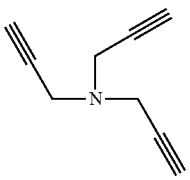

or

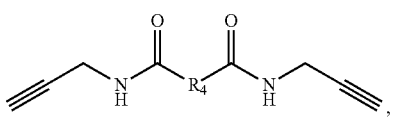

or mixtures thereof
wherein R4 is alkyl, ether.

15. The depot of claim 1, wherein the drug molecules comprise drug molecules wherein a single reactive group of the drug molecule is crosslinked.

16. The depot of claim 1, wherein the drug molecules comprise drug molecules having at least three reactive functional groups.

* * * * *